(12) United States Patent
Minton et al.

(10) Patent No.: US 9,803,208 B2
(45) Date of Patent: Oct. 31, 2017

(54) CONDITIONAL VECTORS AND USES THEREOF

(71) Applicant: The University of Nottingham, Nottingham (GB)

(72) Inventors: Nigel Peter Minton, Nottingham (GB); Ying Zhang, Nottingham (GB)

(73) Assignee: THE UNIVERSITY OF NOTTINGHAM, Nottingham (GB)

( * ) Notice: Subject to any disclaimer, the term of this patent is extended or adjusted under 35 U.S.C. 154(b) by 0 days.

(21) Appl. No.: 14/389,302

(22) PCT Filed: Mar. 28, 2013

(86) PCT No.: PCT/GB2013/050843
§ 371 (c)(1),
(2) Date: Sep. 29, 2014

(87) PCT Pub. No.: WO2013/144653
PCT Pub. Date: Oct. 3, 2013

(65) Prior Publication Data
US 2015/0056706 A1    Feb. 26, 2015

(30) Foreign Application Priority Data

Mar. 30, 2012    (GB) .................................. 1205795.6

(51) Int. Cl.
*C12N 15/63* (2006.01)
*C12N 15/74* (2006.01)

(52) U.S. Cl.
CPC .............. *C12N 15/74* (2013.01); *C12N 15/63* (2013.01); *C12N 2800/90* (2013.01); *C12N 2830/002* (2013.01)

(58) Field of Classification Search
None
See application file for complete search history.

(56) References Cited

U.S. PATENT DOCUMENTS

2011/0027835 A1*  2/2011  Heap ................... C12N 15/902
                                                                 435/91.5

OTHER PUBLICATIONS

Breton et al., Applied and Environmental Microbiology, 2006, vol. 72, pp. 327-333.*
Heap et al., Journal of Microbiological Methods, 2007, vol. 70, pp. 452-464.*
Le Breton et al., Applied and Environmental Microbiology, 2006, vol. 72 pp. 327-333.*
Dupuy et al., Molecular Microbiology, 2006, vol. 60, pp. 1044-1057.*
Madigan et al., Brock Biology of Microorganisms, 11th Ed., 2006, p. 289.*
Le Breton, Yoann et al., "In Vivo Random Mutagenesis of *Bacillus subtilis* by Use of TnYLB-1, a mariner-Based Transposon," Applied and Environmental Microbiology, (Jan. 2006), vol. 72, No. 1, pp. 327-333.
Wilson, Adam C. et al., "New transposon delivery plasmids for insertional mutagenesis in *Bacillus anthracis*," J. Microbiol Methods, (Dec. 2007), vol. 71, Issue 3, pp. 332-335.
Maier, Tamara M. et al., "In Vivo Himarl-Based Transposon Mutagenesis of *Francisella tularensis*," Applied and Environmental Microbiology, (Mar. 2006), vol. 72, No. 3, pp. 1878-1885.
Minton, Nigel et al., "Isolation and Partial Characterization of Three Cryptic Plasmids from Strains of *Clostridium butyricum*," Journal of General Microbiology, (1981), vol. 127, pp. 325-331.
Heap, John T. et al., "The ClosTron: A universal gene knock-out system for the genus *Clostridium*, Journal of Microbiological Methods," (2007), vol. 70, pp. 452-464.
International Search Report received in International Patent Application No. PCT/GB2013/050843 dated Jul. 25, 2013, 4 pages.

* cited by examiner

*Primary Examiner* — Mindy G Brown
(74) *Attorney, Agent, or Firm* — James F. Ewing; Foley & Lardner LLP

(57) ABSTRACT

The present invention now provides a conditional vector comprising DNA encoding for: (i) an inducible expression cassette comprising an inducible promoter operably linked to a plasmid replication region; and (ii) a selectable marker.

15 Claims, 62 Drawing Sheets

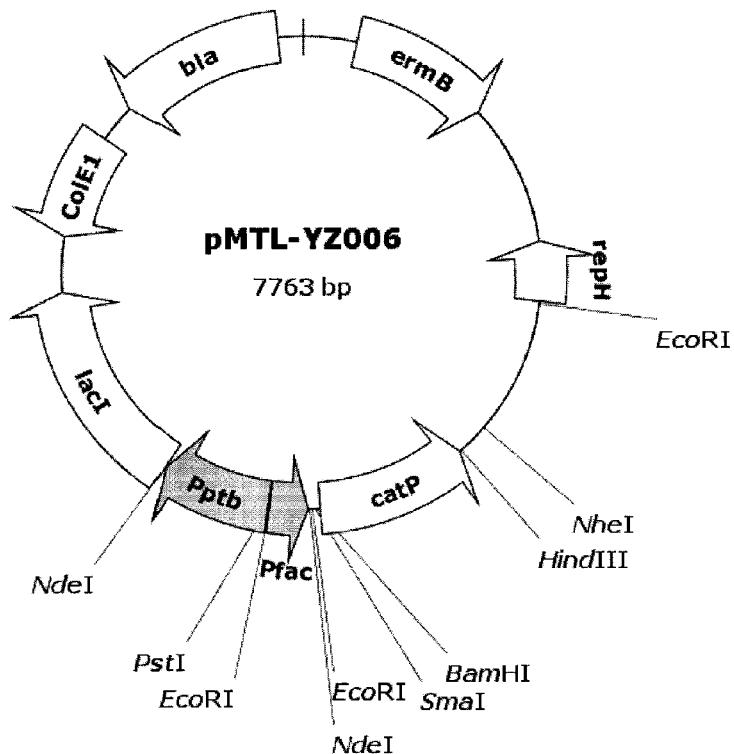

Figure 4:
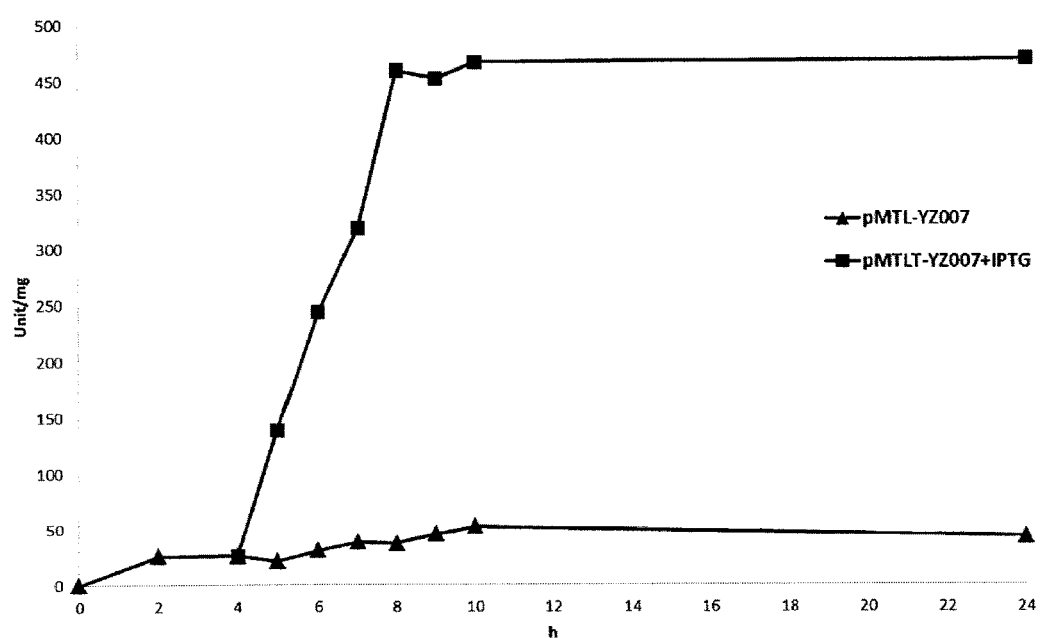

Figure 1.

ACTGCCGGGCCTCTTGCGGGATCAAAAGAAAAACGAAATGATACACCAATCA
GTGCAAAAAAAGATATAATGGGAGATAAGACGGTTCGTGTTCGTGCTGACTT
GCACCATATCATAAAAATCGAAACAGCAAAGAATGGCGGAAACGTAAAAGA
AGTTATGGAAATAAGACTTAGAAGCAAACTTAAGAGTGTGTTGATAGTGCAG
TATCTTAAAATTTTGTATAATAGGAATTGAAGTTAAATTAGATGCTAAAAATT
TGTAATTAAGAAGGAGTGATTACATGAACAAAAATATAAAATATTCTCAAAA
CTTTTTAACGAGTGAAAAAGTACTCAACCAAATAATAAAACAATTGAATTTAA
AAGAAACCGATACCGTTTACGAAATTGGAACAGGTAAAGGGCATTTAACGAC
GAAACTGGCTAAAATAAGTAAACAGGTAACGTCTATTGAATTAGACAGTCAT
CTATTCAACTTATCGTCAGAAAAATTAAAACTGAATACTCGTGTCACTTTAAT
TCACCAAGATATTCTACAGTTTCAATTCCCTAACAAACAGAGGTATAAAATTG
TTGGGAGTATTCCTTACCATTTAAGCACACAAATTATTAAAAAAGTGGTTTTT
GAAAGCCATGCGTCTGACATCTATCTGATTGTTGAAGAAGGATTCTACAAGCG

Figure 1 (continued)

TACCTTGGATATTCACCGAACACTAGGGTTGCTCTTGCACACTCAAGTCTCGA
TTCAGCAATTGCTTAAGCTGCCAGCGGAATGCTTTCATCCTAAACCAAAAGTA
AACAGTGTCTTAATAAAACTTACCCGCCATACCACAGATGTTCCAGATAAATA
TTGGAAGCTATATACGTACTTTGTTTCAAAATGGGTCAATCGAGAATATCGTC
AACTGTTTACTAAAAATCAGTTTCATCAAGCAATGAAACACGCCAAAGTAAA
CAATTTAAGTACCGTTACTTATGAGCAAGTATTGTCTATTTTTAATAGTTATCT
ATTATTTAACGGGAGGAAATAATTCTATGAGTCGCTTTGTAAATTTGGAAAG
TTACACGTTACTAAAGGGAATGTAGATAAATTATTAGGTATACTACTGACAGC
TTCCAAGGAGCTAAAGAGGTCCCTAGCGCCTACGGGGAATTTGATCGTCCATT
CCGACAGCATCGCCAGTCACTATGGCGTGCTGCTAGAGCTTATAATCCATAAC
AATCATCCTTTCTGTGACACTGTCAGACACTTATCACATTAAGTATATACTATT
ATTAAACTATTCTATATACTTAATTTATTTTAATAGAAAAACATAATATCATA
ATAACTTCAAAATTAAACTTTATTTATGATTTCATACTTGACTTTGATTTTAGA
AAGGATATACTTTTTAGCAGATTTGGAAACGGCTTTGGACGTAGTTTGCCCAT
AGATGAACAAACAAACTACATCCAAAAATTATACTTTTCCCTTCATTGGTATC
CGTATTTTTACATCTTAATAGCGTATGTATTACAACACACCTAAACAACGACC
TTACGGTCTGCTACTGCATATCCTAGCTTGATTGTTTAGTTGCCTCAACTATGC
TTAACCCTACCCCGAACTCTTTTTTATTGTGGGTTTTCGTCGTGAAGTCCCAC
CGACACATAATCATAACATAAGATGTATTATGAAAATGCGAGTGACTATCCTT
TTGTATCGGCTCACTACACCACAGATATATTTTTAGTGCATACTGTGTCGGC
ACTCTCAATATTAAATTAATAAATAAATTATTTTTTCTTTTTACTCTTCTTTAC
ATGAGCTTTTTTAAAGCTCCTTGCATAATATTTAATGCATGTACGTTCTTTTTT
CTGTTCTTCCTCTGTAAAACATCTCATTTTTATGGCACACCATCCATATCGGTT
CATCTTTGAACAATTAATACATTGGACTTTCCCTTTATGTAAACATCTTGACTC
ATTGTATTTACTGCAATAGGTTGCTACTGTTTTATCATGAATCATCAACGAAT
GTATTTTGCATATTTCAGTATCTTTAATAAACTCTTTGCAATTTTTACAAGTTT
TCATATACGCCCTTCTTTTCATAAATTAATTTATGAATTCTATGTATTCCAAGG
AGCTTTTTAAAGCTCCCCCTTTCGTACTACTTAGCTACAAGCACTATAAAAGT
CATAATGTTTACTGCTAAAGTCAATAATGATATTGCTAATACCTTGTTATTTGA
TAAGATACTGCTTTCCTCTGTCACTTTGCTCACCCCCTTTCATTTTCATAAATT
AATTATGAAAAATAAATATACTTCTAATTTTATCAAATAAAAAGCCTTTG
CGTACTGCTTCCAATACACAAGGCTATAAACTTCTAAATCTTACTTATTGCA
ATTTACATTTATATCTGTTAAGATAATCTCATAAATTGAATATATATAGTTAAT
GTTTCTCTTGTATGTCGGTACATTTGAAATATTGCTATAGATAGAGTTCTCTAA

Figure 1 (continued)

CGGCTTGATGTGTTGGTAGCACATTTAAGTTTTGGCTTATATACTAAGTTGGT
AGCTTAATATATAAGAGCTGAGGACTTATTTTTTTATTAAATTTTTCAACTTGT
CTATATTTTAACCCGTAATTGAATACATAACAAGTATTTTTTTTGTATTCAAT
TAAACATTCATAAATGAGTATAATTAATCATACTAAATTCTATAATTTTCTTTT
CTGTAAATTTCTTTCTATTCAGCACTGTTATGCCTTTTGACTATCACTTAATAA
AAAATAAGAAATGAATTGTCAATTGTTCAAAAAAATAATGGCTGCTGCATCTC
TTCGCTAGCGCCATTCGCCATTCAGGCTGCGCAACTGTTGGGAAGGGCGATCG
GTGCGGGCCTCTTCGCTATTACGCCAGCTGGCGAAAGGGGGATGTGCTGCAA
GGCGATTAAGTTGGGTAACGCCAGGGTTTTCCCAGTCACGACGTTGTAAAACG
ACGGCCAGTGCCAAGCTTGCATGCCATGGTACCCATCGGCGAGGCTAGTTACC
CTTAAGTTATTGGTATGACTGGTTTTAAGCGCAAAAAAGTTGCTTTTTCGTA
CCTATTAAGTTATCGTTAGAAAACCGACTGTAAAAGTACAGTCGGCATTATC
TCATATTATAAAAGCCAGTCATTAGGCCTATCTGACAATTCCTGAATAGAGTT
CATAAACAATCCTGCATGATAACCATCACAAACAGAATGATGTACCTGTAAA
GATAGCGGTAAATATATTGAATTACCTTTATTAATGAATTTTCCTGCTGTAAT
AATGGGTAGAAGGTAATTACTATTATTATTGATATTTAAGTTAAACCCAGTAA
ATGAAGTCCATGGAATAATAGAAAGAGAAAAGCATTTTCAGGTATAGGTGT
TTTGGGAAACAATTTCCCCGAACCATTATATTTCTCTACATCAGAAAGGTATA
AATCATAAAACTCTTTGAAGTCATTCTTTACAGGAGTCCAAATACCAGAGAAT
GTTTTAGATACACCATCAAAAATTGTATAAAGTGGCTCTAACTTATCCCAATA
ACCTAACTCTCCGTCGCTATTGTAACCAGTTCTAAAAGCTGTATTTGAGTTTAT
CACCCTTGTCACTAAGAAAATAAATGCAGGGTAAAATTTATATCCTTCTTGTT
TTATGTTTCGGTATAAAACACTAATATCAATTTCTGTGGTTATACTAAAAGTC
GTTTGTTGGTTCAAATAATGATTAAATATCTCTTTTCTCTTCCAATTGTCTAAA
TCAATTTTATTAAAGTTCATTTGATATGCCTCCTAAATGGGGATCCCCGGGTA
CCGAGCTCGAATTCGTAATCATGGTCATATGAAATACACCTCCTTAAAATTTT
AATCATAAGTTGGAATTGTGAGCGGATAACAATTCCAACCATAACTTATTGTA
TCATGTTTTTAAACTTTTTAAAAGTGTAATTTATATTACAGTAAATCCTAAATC
TTCTATTGCTTCTATAACTTTATCTATATTTAAGAATATGCATCATATACTAT
CTCGATCCGGGGAATTCTCTGCAGATAATTCAGGGAATTAAAAGAATGTTTAC
CTGATTATGTTGTAGAGGCTCTTAAAGAAGGAATTATAAATTTTGATAAAAAG
ATAAAAGGGTATGCAAGAGAAGATGCAATTTTAACGGGAATTGAGACAAGAA
CATCAGCACCAGTTAGATTGAATAGAAATGCTTCACTTGAAAGTATAAATGTA
TGCGGACTTTATCCAACTGGAGAAGGGGCAGGATTTGCAGGTGGTATAATAT

Figure 1 (continued)

CAGCGGCTGTTGATGGGATAAAGGTTGCCGAACATATAATTGAAAAATTCGA
TTTACCAAAATAAGATTATAAGTAACATGAATAGAATTAGTATAATCTTTTCA
GAAGATGAGGAAGATATATTATATTACGTTCGTGTTGTGAAATCTTATAAAAA
TGAATATATAAAATTAATAATATAATAAAAATAATATTCTGAAAATTCAACAT
TTCCAATATTTTTTGTTACAATAAGGTATAAAGAAATATTCATAGCATTGATT
GATATAAATTTAACAAACAATTAAATTAATCATATATAAAAGTTAAAAATTAT
TAAAGTAGAGGTGCAACATATGAAACCAGTAACGTTATACGATGTCGCAGAG
TATGCCGGTGTCTCTTATCAGACCGTTTCCGCGTGGTGAACCAGGCCAGCCA
CGTTTCTGCGAAAACGCGGGAAAAAGTGGAAGCGGCGATGGCGGAGCTGAAT
TACATTCCCAACCGCGTGGCACAACAACTGGCGGGCAAACAGTCGTTGCTGA
TTGGCGTTGCCACCTCCAGTCTGGCCCTGCACGCGCCGTCGCAAATTGTCGCG
GCGATTAAATCTCGCGCCGATCAACTGGGTGCCAGCGTGGTGGTGTCGATGGT
AGAACGAAGCGGCGTCGAAGCCTGTAAAGCGGCGGTGCACAATCTTCTCGCG
CAACGCGTCAGTGGGCTGATCATTAACTATCCGCTGGATGACCAGGATGCCAT
TGCTGTGGAAGCTGCCTGCACTAATGTTCCGGCGTTATTTCTTGATGTCTCTGA
CCAGACACCCATCAACAGTATTATTTTCTCCCATGAAGACGGTACGCGACTGG
GCGTGGAGCATCTGGTCGCATTGGGTCACCAGCAAATCGCGCTGTTAGCGGG
CCCATTAAGTTCTGTCTCGGCGCGTCTGCGTCTGGCTGGCTGGCATAAATATC
TCACTCGCAATCAAATTCAGCCGATAGCGGAACGGGAAGGCGACTGGAGTGC
CATGTCCGGTTTTCAACAAACCATGCAAATGCTGAATGAGGGCATCGTTCCCA
CTGCGATGCTGGTTGCCAACGATCAGATGGCGCTGGGCGCAATGCGCGCCATT
ACCGAGTCCGGGCTGCGCGTTGGTGCGGATATCTCGGTAGTGGGATACGACG
ATACCGAAGACAGCTCATGTTATATCCCGCCGTCAACCACCATCAAACAGGAT
TTTCGCCTGCTGGGGCAAACCAGCGTGGACCGCTTGCTGCAACTCTCTCAGGG
CCAGGCGGTGAAGGGCAATCAGCTGTTGCCCGTCTCACTGGTGAAAAGAAAA
ACCACCCTGGCGCCCAATACGCAAACCGCCTCTCCCCGCGCGTTGGCCGATTC
ATTAATGCAGCTGGCACGACAGGTTTCCCGACTGGAAAGCGGGCAGTGAGCG
CAACGCAATTAATGTGAGTTAGGAATTATCCCGTGACAGGTCATTCAGACTGG
CTAATGCACCCAGTAAGGCAGCGGTATCATCAACAGGCTTACCCGTCTTACTG
CTTCCGCTTCCTCGCTCACTGACTCGCTGCGCTCGGTCGTTCGGCTGCGGCGA
GCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGACGAG
CATCACAAAAATCGACGCTCAAGTCAGAGGTGGCGAAACCCGACAGGACTAT

Figure 1 (continued)

AAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGC
GCTTTCTCAATGCTCACGCTGTAGGTATCTCAGTTCGGTGTAGGTCGTTCGCTC
CAAGCTGGGCTGTGTGCACGAACCCCCCGTTCAGCCCGACCGCTGCGCCTTAT
CCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTA
CAGAGTTCTTGAAGTGGTGGCCTAACTACGGCTACACTAGAAGGACAGTATTT
GGTATCTGCGCTCTGCTGAAGCCAGTTACCTTCGGAAAAGAGTTGGTAGCTC
TTGATCCGGCAAACAAACCACCGCTGGTAGCGGTGGTTTTTTTGTTTGCAAGC
AGCAGATTACGCGCAGAAAAAAGGATCTCAAGAAGATCCTTTGATCTTTTCT
ACGGGGTCTGACGCTCAGTGGAACGAAAACTCACGTTAAGGGATTTTGGTCA
TGAGATTATCAAAAAGGATCTTCACCTAGATCCTTTTAAATTAAAAATGAAGT
TTTAAATCAATCTAAAGTATATATGAGTAAACTTGGTCTGACAGTTACCAATG
CTTAATCAGTGAGGCACCTATCTCAGCGATCTGTCTATTTCGTTCATCCATAGT
TGCCTGACTCCCCGTCGTGTAGATAACTACGATACGGGAGGGCTTACCATCTG
GCCCCAGTGCTGCAATGATACCGCGAGACCCACGCTCACCGGCTCCAGATTTA
TCAGCAATAAACCAGCCAGCCGGAAGGGCCGAGCGCAGAAGTGGTCCTGCAA
CTTTATCCGCCTCCATCCAGTCTATTAATTGTTGCCGGGAAGCTAGAGTAAGT
AGTTCGCCAGTTAATAGTTTGCGCAACGTTGTTGCCATTGCTACAGGCATCGT
GGTGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCTTC
GGTCCTCCGATCGTTGTCAGAAGTAAGTTGGCCGCAGTGTTATCACTCATGGT
TATGGCAGCACTGCATAATTCTCTTACTGTCATGCCATCCGTAAGATGCTTTTC
TGTGACTGGTGAGTACTCAACCAAGTCATTCTGAGAATAGTGTATGCGGCGAC
CGAGTTGCTCTTGCCCGGCGTCAATACGGGATAATACCGCGCCACATAGCAG
AACTTTAAAAGTGCTCATCATTGGAAAACGTTCTTCGGGGCGAAAACTCTCAA
GGATCTTACCGCTGTTGAGATCCAGTTCGATGTAACCCACTCGTGCACCCAAC
TGATCTTCAGCATCTTTTACTTTCACCAGCGTTTCTGGGTGAGCAAAAACAGG
AAGGCAAAATGCCGCAAAAAGGGAATAAGGGCGACACGGAAATGTTGAAT
ACTCATACTCTTCCTTTTCAATATTATTGAAGCATTTATCAGGGTTATTGTCT
CATGAGCGGATACATATTTGAATGTATTTAGAAAAATAAACAAATAGGGGTT
CCGCGCACATTTCCCCGAAAAGTGCCACCTG

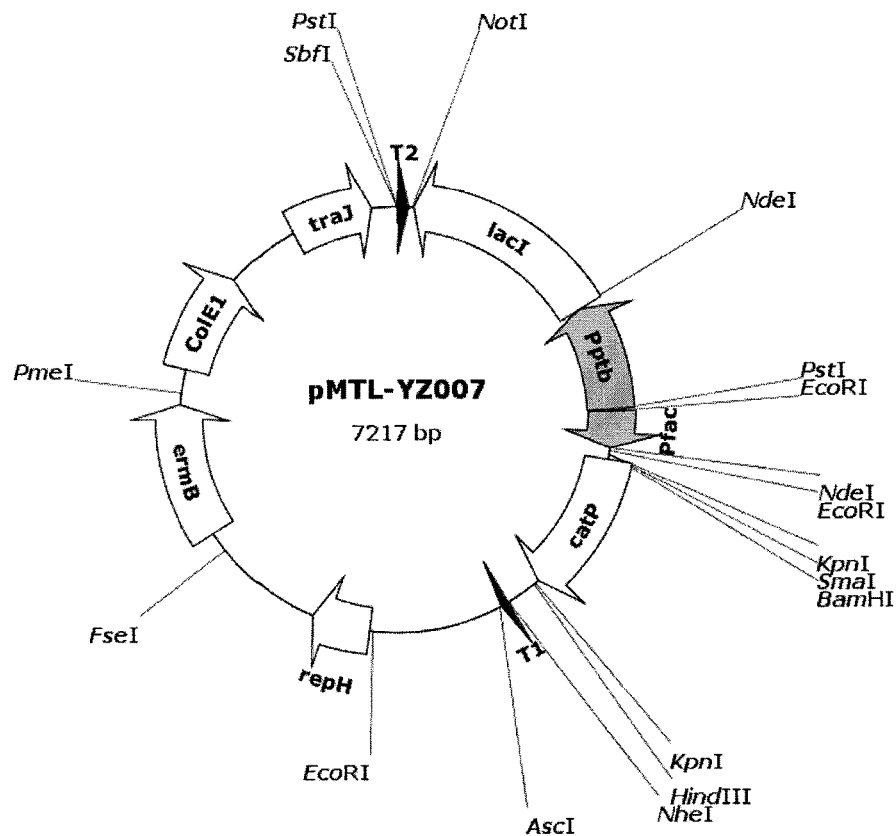

Figure 2.
CCTGCAGGATAAAAAAATTGTAGATAAATTTTATAAAATAGTTTTATCTACAA
TTTTTTTATCAGGAAACAGCTATGACCGCGGCCGCGCTCACTGCCCGCTTTCC
AGTCGGGAAACCTGTCGTGCCAGCTGCATTAATGAATCGGCCAACGCGCGGG
GAGAGGCGGTTTGCGTATTGGGCGCCAGGGTGGTTTTTCTTTTCACCAGTGAG
ACGGGCAACAGCTGATTGCCCTTCACCGCCTGGCCCTGAGAGAGTTGCAGCA
AGCGGTCCACGCTGGTTTGCCCCAGCAGGCGAAAATCCTGTTTGATGGTGGTT
AACGGCGGGATATAACATGAGCTGTCTTCGGTATCGTCGTATCCCACTACCGA
GATATCCGCACCAACGCGCAGCCCGGACTCGGTAATGGCGCGCATTGCGCCC
AGCGCCATCTGATCGTTGGCAACCAGCATCGCAGTGGGAACGATGCCCTCATT
CAGCATTTGCATGGTTTGTTGAAAACCGGACATGGCACTCCAGTCGCCTTCCC
GTTCCGCTATCGGCTGAATTTGATTGCGAGTGAGATATTTATGCCAGCCAGCC
AGACGCAGACGCGCCGAGACAGAACTTAATGGGCCCGCTAACAGCGCGATTT
GCTGGTGACCCAATGCGACCAGATGCTCCACGCCCAGTCGCGTACCGTCTTCA

Figure 2 (continued)

TGGGAGAAAATAATACTGTTGATGGGTGTCTGGTCAGAGACATCAAGAAATA
ACGCCGGAACATTAGTGCAGGCAGCTTCCACAGCAATGGCATCCTGGTCATCC
AGCGGATAGTTAATGATCAGCCCACTGACGCGTTGCGCGAGAAGATTGTGCA
CCGCCGYTTTACAGGCTTCGACGCCGCTTCGTTCTACCATCGACACCACCACG
CTGGCACCCAGTTGATCGGCGCGAGATTTAATCGCCGCGACAATTTGCGACGG
CGCGTGCAGGGCCAGACTGGAGGTGGCAACGCCAATCAGCAACGACTGTTTG
CCCGCCAGTTGTTGTGCCACGCGGTTGGGAATGTAATTCAGCTCCGCCATCGC
CGCTTCCACTTTTTCCCGCGTTTTCGCAGAAACGTGGCTGGCCTGGTTCACCAC
GCGGGAAACGGTCTGATAAGAGACACCGGCATACTCTGCGACATCGTATAAC
GTTACTGGTTTCATATGTTGCACCTCTACTTTAATAATTTTTAACTTTTATATA
TGATTAATTTAATTGTTTGTTAAATTTATATCAATCAATGCTATGAATATTTCT
TTATACCTTATTGTAACAAAAAATATTGGAAATGTTGAATTTTCAGAATATT
ATTTTTATTATATTATTAATTTTATATATTCATTTTTATAAGATTTCACAACAC
GAACGTAATATAATATATCTTCCTCATCTTCTGAAAAGATTATACTAATTCTAT
TCATGTTACTTATAATCTTATTTTGGTAAATCGAATTTTTCAATTATATGTTCG
GCAACCTTTATCCCATCAACAGCCGCTGATATTATACCACCTGCAAATCCTGC
CCCTTCTCCAGTTGGATAAAGTCCGCATACATTTATACTTTCAAGTGAAGCAT
TTCTATTCAATCTAACTGGTGCTGATGTTCTTGTCTCAATTCCCGTTAAAATTG
CATCTTCTCTTGCATACCCTTTTATCTTTTATCAAAATTTATAATTCCTTCTTT
AAGAGCCTCTACAACATAATCAGGTAAACATTCTTTTAATTCCCTGAATTATC
TGCAGAGAATTCCCCGGATCGAGATAGTATATGATGCATATTCTTTAAATATA
GATAAAGTTATAGAAGCAATAGAAGATTTAGGATTTACTGTAATATAAATTAC
ACTTTTAAAAAGTTTAAAAACATGATACAATAAGTTATGGTTGGAATTGTTAT
CCGCTCACAATTCCAACTTATGATTAAAATTTTAAGGAGGTGTATTTCATATG
ACCATGATTACGAATTCGAGCTCGGTACCCGGGGATCCCCATTTAGGAGGCAT
ATCAAATGAACTTTAATAAAATTGATTTAGACAATTGGAAGAGAAAGAGAT
ATTTAATCATTATTTGAACCAACAAACGACTTTTAGTATAACCACAGAAATTG
ATATTAGTGTTTTATACCGAAACATAAAACAAGAAGGATATAAATTTTACCCT
GCATTTATTTTCTTAGTGACAAGGGTGATAAACTCAAATACAGCTTTTAGAAC
TGGTTACAATAGCGACGGAGAGTTAGGTTATTGGGATAAGTTAGAGCCACTTT
ATACAATTTTTGATGGTGTATCTAAAACATTCTCTGGTATTTGGACTCCTGTAA
AGAATGACTTCAAAGAGTTTTATGATTTATACCTTTCTGATGTAGAGAAATAT
AATGGTTCGGGGAAATTGTTTCCCAAAACACCTATACCTGAAAATGCTTTTTC
TCTTTCTATTATTCCATGGACTTCATTTACTGGGTTTAACTTAAATATCAATAA

Figure 2 (continued)

TAATAGTAATTACCTTCTACCCATTATTACAGCAGGAAAATTCATTAATAAAG
GTAATTCAATATATTTACCGCTATCTTTACAGGTACATCATTCTGTTTGTGATG
GTTATCATGCAGGATTGTTTATGAACTCTATTCAGGAATTGTCAGATAGGCCT
AATGACTGGCTTTTATAATATGAGATAATGCCGACTGTACTTTTTACAGTCGG
TTTTCTAACGATACATTAATAGGTACGAAAAAGCAACTTTTTTGCGCTTAAA
ACCAGTCATACCAATAACTTAAGGGTAACTAGCCTCGCCGATGGGTACCATG
GCATGCAAGCTTGGCACTGGCCGTCGTTTTACAACGTCGTGACTGGGAAAACC
CTGGCGTTACCCAACTTAATCGCCTTGCAGCACATCCCCCTTTCGCCAGCTGG
CGTAATAGCGAAGAGGCCCGCACCGATCGCCCTTCCCAACAGTTGCGCAGCC
TGAATGGCGAATGGCGCTAGCATAAAAATAAGAAGCCTGCATTTGCAGGCTT
CTTATTTTTATGGCGCGCCGCCATTATTTTTTGAACAATTGACAATTCATTTC
TTATTTTTTATTAAGTGATAGTCAAAAGGCATAACAGTGCTGAATAGAAAGAA
ATTTACAGAAAAGAAAATTATAGAATTTAGTATGATTAATTATACTCATTTAT
GAATGTTTAATTGAATACAAAAAAAATACTTGTTATGTATTCAATTACGGGT
TAAAATATAGACAAGTTGAAAAATTTAATAAAAAAATAAGTCCTCAGCTCTT
ATATATTAAGCTACCAACTTAGTATATAAGCCAAAACTTAAATGTGCTACCAA
CACATCAAGCCGTTAGAGAACTCTATCTATAGCAATATTTCAAATGTACCGAC
ATACAAGAGAAACATTAACTATATATATTCAATTTATGAGATTATCTTAACAG
ATATAAATGTAAATTGCAATAAGTAAGATTTAGAAGTTTATAGCCTTTGTGTA
TTGGAAGCAGTACGCAAAGGCTTTTTATTTGATAAAAATTAGAAGTATATTT
ATTTTTTCATAATTAATTTATGAAAATGAAAGGGGGTGAGCAAAGTGACAGA
GGAAAGCAGTATCTTATCAAATAACAAGGTATTAGCAATATCATTATTGACTT
TAGCAGTAAACATTATGACTTTTATAGTGCTTGTAGCTAAGTAGTACGAAAGG
GGGAGCTTTAAAAAGCTCCTTGGAATACATAGAATTCATAAATTAATTTATGA
AAAGAAGGGCGTATATGAAACTTGTAAAAATTGCAAAGAGTTTATTAAAGA
TACTGAAATATGCAAAATACATTCGTTGATGATTCATGATAAAACAGTAGCAA
CCTATTGCAGTAAATACAATGAGTCAAGATGTTTACATAAAGGGAAAGTCCA
ATGTATTAATTGTTCAAAGATGAACCGATATGGATGGTGTGCCATAAAAATGA
GATGTTTTACAGAGGAAGAACAGAAAAAGAACGTACATGCATTAAATATTA
TGCAAGGAGCTTTAAAAAAGCTCATGTAAAGAAGAGTAAAAAGAAAAAATA
ATTTATTTATTAATTTAATATTGAGAGTGCCGACACAGTATGCACTAAAAAAT
ATATCTGTGGTGTAGTGAGCCGATACAAAAGGATAGTCACTCGCATTTTCATA
ATACATCTTATGTTATGATTATGTGTCGGTGGGACTTCACGACGAAAACCCAC
AATAAAAAAGAGTTCGGGGTAGGGTTAAGCATAGTTGAGGCAACTAAACAA

Figure 2 (continued)

TCAAGCTAGGATATGCAGTAGCAGACCGTAAGGTCGTTGTTTAGGTGTGTTGT
AATACATACGCTATTAAGATGTAAAAATACGGATACCAATGAAGGGAAAAGT
ATAATTTTTGGATGTAGTTTGTTTGTTCATCTATGGGCAAACTACGTCCAAAG
CCGTTTCCAAATCTGCTAAAAGTATATCCTTTCTAAAATCAAAGTCAAGTAT
GAAATCATAAATAAAGTTTAATTTTGAAGTTATTATGATATTATGTTTTTCTAT
TAAAATAAATTAAGTATATAGAATAGTTTAATAATAGTATATACTTAATGTGA
TAAGTGTCTGACAGTGTCACAGAAGGATGATTGTTATGGATTATAAGCGGCC
GGCCGAAGCAAACTTAAGAGTGTGTTGATAGTGCAGTATCTTAAAATTTTGTA
TAATAGGAATTGAAGTTAAATTAGATGCTAAAAATTTGTAATTAAGAAGGAG
TGATTACATGAACAAAAATATAAAATATTCTCAAAACTTTTTAACGAGTGAAA
AAGTACTCAACCAAATAATAAAACAATTGAATTTAAAAGAAACCGATACCGT
TTACGAAATTGGAACAGGTAAAGGGCATTTAACGACGAAACTGGCTAAAATA
AGTAAACAGGTAACGTCTATTGAATTAGACAGTCATCTATTCAACTTATCGTC
AGAAAAATTAAAACTGAATACTCGTGTCACTTTAATTCACCAAGATATTCTAC
AGTTTCAATTCCCTAACAAACAGAGGTATAAAATTGTTGGGAGTATTCCTTAC
CATTTAAGCACACAAATTATTAAAAAAGTGGTTTTTGAAAGCCATGCGTCTGA
CATCTATCTGATTGTTGAAGAAGGATTCTACAAGCGTACCTTGGATATTCACC
GAACACTAGGGTTGCTCTTGCACACTCAAGTCTCGATTCAGCAATTGCTTAAG
CTGCCAGCGGAATGCTTTCATCCTAAACCAAAAGTAAACAGTGTCTTAATAAA
ACTTACCCGCCATACCACAGATGTTCCAGATAAATATTGGAAGCTATATACGT
ACTTTGTTTCAAAATGGGTCAATCGAGAATATCGTCAACTGTTTACTAAAAAT
CAGTTTCATCAAGCAATGAAACACGCCAAAGTAAACAATTTAAGTACCGTTA
CTTATGAGCAAGTATTGTCTATTTTAATAGTTATCTATTATTTAACGGGAGGA
AATAATTCTATGAGTCGCTTTTGTAAATTTGGAAAGTTACACGTTACTAAAGG
GAATGTGTTTAAACTCCTTTTTGATAATCTCATGACCAAAATCCCTTAACGTG
AGTTTCGTTCCACTGAGCGTCAGACCCCGTAGAAAGATCAAAGGATCTTCT
TGAGATCCTTTTTTTCTGCGCGTAATCTGCTGCTTGCAAACAAAAAAACCACC
GCTACCAGCGGTGGTTTGTTTGCCGGATCAAGAGCTACCAACTCTTTTTCCGA
AGGTAACTGGCTTCAGCAGAGCGCAGATACCAAATACTGTTCTTCTAGTGTAG
CCGTAGTTAGGCCACCACTTCAAGAACTCTGTAGCACCGCCTACATACCTCGC
TCTGCTAATCCTGTTACCAGTGGCTGCTGCCAGTGGCGATAAGTCGTGTCTTA
CCGGGTTGGACTCAAGACGATAGTTACCGGATAAGGCGCAGCGGTCGGGCTG
AACGGGGGGTTCGTGCACACAGCCCAGCTTGGAGCGAACGACCTACACCGAA
CTGAGATACCTACAGCGTGAGCTATGAGAAAGCGCCACGCTTCCCGAAGGGA

Figure 2 (continued)

GAAAGGCGGACAGGTATCCGGTAAGCGGCAGGGTCGGAACAGGAGAGCGCA
CGAGGGAGCTTCCAGGGGGAAACGCCTGGTATCTTTATAGTCCTGTCGGGTTT
CGCCACCTCTGACTTGAGCGTCGATTTTTGTGATGCTCGTCAGGGGGGCGGAG
CCTATGGAAAAACGCCAGCAACGCGGCCTTTTTACGGTTCCTGGCCTTTTGCT
GGCCTTTTGCTCACATGTTCTTTCCTGCGTTATCCCCTGATTCTGTGGATAACC
GTATTACCGCCTTTGAGTGAGCTGATACCGCTCGCCGCAGCCGAACGACCGAG
CGCAGCGAGTCAGTGAGCGAGGAAGCGGAAGAGCGCCCAATACGCAGGGCC
CCCTGCTTCGGGGTCATTATAGCGATTTTTTCGGTATATCCATCCTTTTTCGCA
CGATATACAGGATTTTGCCAAAGGGTTCGTGTAGACTTTCCTTGGTGTATCCA
ACGGCGTCAGCCGGGCAGGATAGGTGAAGTAGGCCCACCCGCGAGCGGGTGT
TCCTTCTTCACTGTCCCTTATTCGCACCTGGCGGTGCTCAACGGGAATCCTGCT
CTGCGAGGCTGGCCGGCTACCGCCGGCGTAACAGATGAGGGCAAGCGGATGG
CTGATGAAACCAAGCCAACCAGGAAGGGCAGCCCACCTATCAAGGTGTACTG
CCTTCCAGACGAACGAAGAGCGATTGAGGAAAAGGCGGCGGCGGCCGGCATG
AGCCTGTCGGCCTACCTGCTGGCCGTCGGCCAGGGCTACAAAATCACGGGCG
TCGTGGACTATGAGCACGTCCGCGAGCTGGCCCGCATCAATGGCGACCTGGG
CCGCCTGGGCGGCCTGCTGAAACTCTGGCTCACCGACGACCCGCGCACGGCG
CGGTTCGGTGATGCCACGATCCTCGCCCTGCTGGCGAAGATCGAAGAGAAGC
AGGACGAGCTTGGCAAGGTCATGATGGGCGTGGTCCGCCCGAGGGCAGAGCC
ATGACTTTTTTAGCCGCTAAAACGGCCGGGGGTGCGCGTGATTGCCAAGCAC
GTCCCCATGCGCTCCATCAAGAAGAGCGACTTCGCGGAGCTGGTGAAGTACA
TCACCGACGAGCAAGGCAAGACCGATCGGGCCC

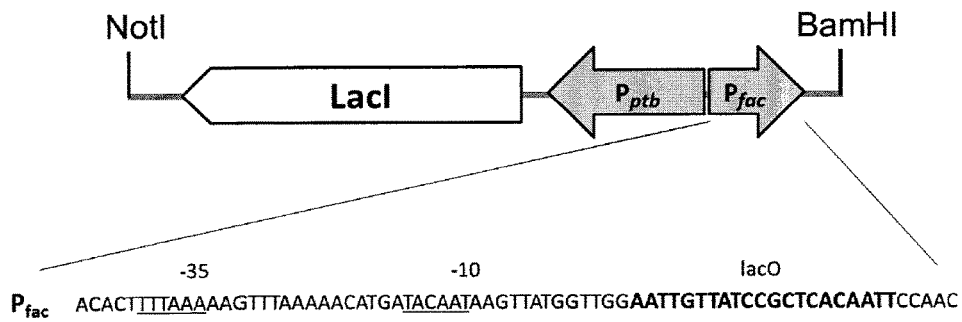

P_fac  ACACT<u>TTTAAA</u>AAGTTTAAAAACATGA<u>TACAAT</u>AAGTTATGGTTGGAATTGTTATCCGCTCACAATTCCAAC

Figure 3.

<u>GCGGCCGC</u>GCTCACTGCCCGCTTTCCAGTCGGGAAACCTGTCGTGCCAGCTGC
ATTAATGAATCGGCCAACGCGCGGGGAGAGGCGGTTTGCGTATTGGGCGCCA
GGGTGGTTTTTCTTTTCACCAGTGAGACGGGCAACAGCTGATTGCCCTTCACC
GCCTGGCCCTGAGAGAGTTGCAGCAAGCGGTCCACGCTGGTTTGCCCCAGCA
GGCGAAAATCCTGTTTGATGGTGGTTAACGGCGGGATATAACATGAGCTGTCT
TCGGTATCGTCGTATCCCACTACCGAGATATCCGCACCAACGCGCAGCCCGGA
CTCGGTAATGGCGCGCATTGCGCCCAGCGCCATCTGATCGTTGGCAACCAGCA
TCGCAGTGGGAACGATGCCCTCATTCAGCATTTGCATGGTTTGTTGAAAACCG
GACATGGCACTCCAGTCGCCTTCCCGTTCCGCTATCGGCTGAATTTGATTGCG
AGTGAGATATTTATGCCAGCCAGCCAGACGCAGACGCGCCGAGACAGAACTT
AATGGGCCCGCTAACAGCGCGATTTGCTGGTGACCCAATGCGACCAGATGCT
CCACGCCCAGTCGCGTACCGTCTTCATGGGAGAAAATAATACTGTTGATGGGT
GTCTGGTCAGAGACATCAAGAAATAACGCCGGAACATTAGTGCAGGCAGCTT
CCACAGCAATGGCATCCTGGTCATCCAGCGGATAGTTAATGATCAGCCCACTG
ACGCGTTGCGCGAGAAGATTGTGCACCGCCGYTTTACAGGCTTCGACGCCGCT
TCGTTCTACCATCGACACCACCACGCTGGCACCCAGTTGATCGGCGCGAGATT
TAATCGCCGCGACAATTTGCGACGGCGCGTGCAGGGCCAGACTGGAGGTGGC
AACGCCAATCAGCAACGACTGTTTGCCCGCCAGTTGTTGTGCCACGCGGTTGG
GAATGTAATTCAGCTCCGCCATCGCCGCTTCCACTTTTTCCCGCGTTTTCGCAG
AAACGTGGCTGGCCTGGTTCACCACGCGGGAAACGGTCTGATAAGAGACACC
GGCATACTCTGCGACATCGTATAACGTTACTGGTTTCATATGTTGCACCTCTA

Figure 3 (continued)

CTTTAATAATTTTAACTTTTATATATGATTAATTTAATTGTTTGTTAAATTTAT
ATCAATCAATGCTATGAATATTTCTTTATACCTTATTGTAACAAAAAAATATT
GGAAATGTTGAATTTTCAGAATATTATTTTTATTATATTATTAATTTTATATAT
TCATTTTTATAAGATTTCACAACACGAACGTAATATAATATATCTTCCTCATCT
TCTGAAAAGATTATACTAATTCTATTCATGTTACTTATAATCTTATTTTGGTAA
ATCGAATTTTTCAATTATATGTTCGGCAACCTTTATCCCATCAACAGCCGCTG
ATATTATACCACCTGCAAATCCTGCCCCTTCTCCAGTTGGATAAAGTCCGCAT
ACATTTATACTTTCAAGTGAAGCATTTCTATTCAATCTAACTGGTGCTGATGTT
CTTGTCTCAATTCCCGTTAAAATTGCATCTTCTCTTGCATACCCTTTTATCTTTT
TATCAAAATTTATAATTCCTTCTTTAAGAGCCTCTACAACATAATCAGGTAAA
CATTCTTTTAATTCCCTGAATTATCTGCAGAGAATTCCCCGGATCGAGATAGT
ATATGATGCATATTCTTTAAATATAGATAAAGTTATAGAAGCAATAGAAGATT
TAGGATTTACTGTAATATAAATTACACTTTTAAAAAGTTTAAAAACATGATAC
AATAAGTTATGGTTGGAATTGTTATCCGCTCACAATTCCAACTTATGATTAAA
ATTTTAAGGAGGTGTATTTCATATGACCATGATTACGAATTCGAGCTCGGTAC
CCGG<u>GGATCC</u>

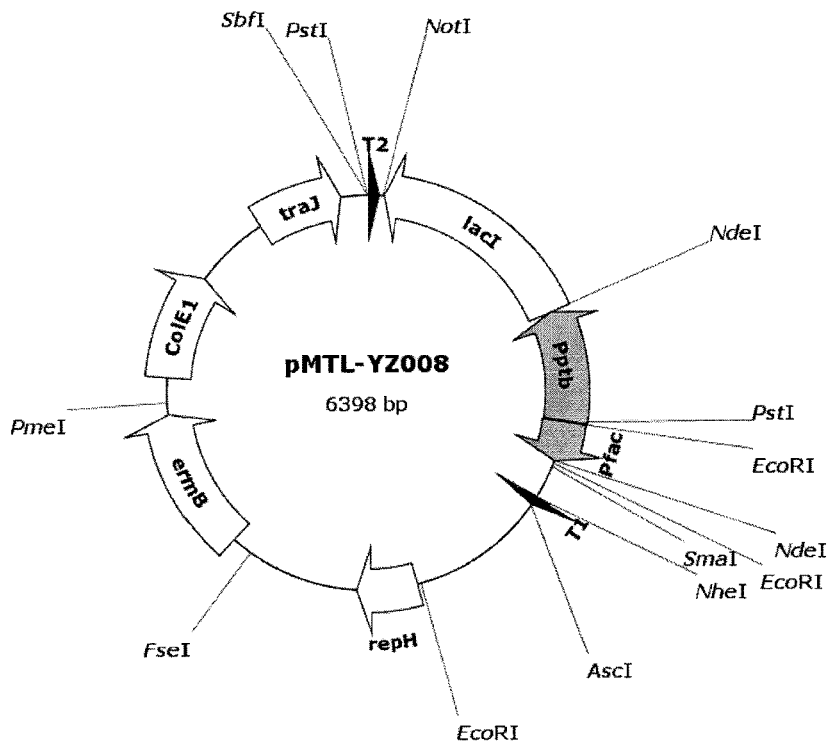

Figure 5.
CCTGCAGGATAAAAAAATTGTAGATAAATTTTATAAAATAGTTTTATCTACAA
TTTTTTTATCAGGAAACAGCTATGACCGCGGCCGCGCTCACTGCCCGCTTTCC
AGTCGGGAAACCTGTCGTGCCAGCTGCATTAATGAATCGGCCAACGCGCGGG
GAGAGGCGGTTTGCGTATTGGGCGCCAGGGTGGTTTTTCTTTTCACCAGTGAG
ACGGGCAACAGCTGATTGCCCTTCACCGCCTGGCCCTGAGAGAGTTGCAGCA
AGCGGTCCACGCTGGTTTGCCCCAGCAGGCGAAAATCCTGTTTGATGGTGGTT
AACGGCGGGATATAACATGAGCTGTCTTCGGTATCGTCGTATCCCACTACCGA
GATATCCGCACCAACGCGCAGCCCGGACTCGGTAATGGCGCGCATTGCGCCC
AGCGCCATCTGATCGTTGGCAACCAGCATCGCAGTGGGAACGATGCCCTCATT
CAGCATTTGCATGGTTTGTTGAAAACCGGACATGGCACTCCAGTCGCCTTCCC
GTTCCGCTATCGGCTGAATTTGATTGCGAGTGAGATATTTATGCCAGCCAGCC
AGACGCAGACGCGCCGAGACAGAACTTAATGGGCCCGCTAACAGCGCGATTT
GCTGGTGACCCAATGCGACCAGATGCTCCACGCCCAGTCGCGTACCGTCTTCA
TGGGAGAAAATAATACTGTTGATGGGTGTCTGGTCAGAGACATCAAGAAATA
ACGCCGGAACATTAGTGCAGGCAGCTTCCACAGCAATGGCATCCTGGTCATCC

Figure 5 (continued)

AGCGGATAGTTAATGATCAGCCCACTGACGCGTTGCGCGAGAAGATTGTGCA
CCGCCGYTTTACAGGCTTCGACGCCGCTTCGTTCTACCATCGACACCACCACG
CTGGCACCCAGTTGATCGGCGCGAGATTTAATCGCCGCGACAATTTGCGACGG
CGCGTGCAGGGCCAGACTGGAGGTGGCAACGCCAATCAGCAACGACTGTTTG
CCCGCCAGTTGTTGTGCCACGCGGTTGGGAATGTAATTCAGCTCCGCCATCGC
CGCTTCCACTTTTTCCCGCGTTTTCGCAGAAACGTGGCTGGCCTGGTTCACCAC
GCGGGAAACGGTCTGATAAGAGACACCGGCATACTCTGCGACATCGTATAAC
GTTACTGGTTTCATATGTTGCACCTCTACTTTAATAATTTTAACTTTTATATA
TGATTAATTTAATTGTTTGTTAAATTTATATCAATCAATGCTATGAATATTTCT
TTATACCTTATTGTAACAAAAAATATTGGAAATGTTGAATTTTCAGAATATT
ATTTTTATTATATTATTAATTTTATATATTCATTTTTATAAGATTTCACAACAC
GAACGTAATATAATATATCTTCCTCATCTTCTGAAAAGATTATACTAATTCTAT
TCATGTTACTTATAATCTTATTTTGGTAAATCGAATTTTTCAATTATATGTTCG
GCAACCTTTATCCCATCAACAGCCGCTGATATTATACCACCTGCAAATCCTGC
CCCTTCTCCAGTTGGATAAAGTCCGCATACATTTATACTTTCAAGTGAAGCAT
TTCTATTCAATCTAACTGGTGCTGATGTTCTTGTCTCAATTCCCGTTAAAATTG
CATCTTCTCTTGCATACCCTTTTATCTTTTATCAAAATTTATAATTCCTTCTTT
AAGAGCCTCTACAACATAATCAGGTAAACATTCTTTTAATTCCCTGAATTATC
TGCAGAGAATTCCCCGGATCGAGATAGTATATGATGCATATTCTTTAAATATA
GATAAAGTTATAGAAGCAATAGAAGATTTAGGATTTACTGTAATATAAATTAC
ACTTTTAAAAAGTTTAAAAACATGATACAATAAGTTATGGTTGGAATTGTTAT
CCGCTCACAATTCCAACTTATGATTAAAATTTTAAGGAGGTGTATTTCATATG
ACCATGATTACGAATTCGAGCTCGGTACCCGGGGATCAGCTTGGCACTGGCCG
TCGTTTTACAACGTCGTGACTGGGAAAACCCTGGCGTTACCCAACTTAATCGC
CTTGCAGCACATCCCCCTTTCGCCAGCTGGCGTAATAGCGAAGAGGCCCGCAC
CGATCGCCCTTCCCAACAGTTGCGCAGCCTGAATGGCGAATGGCGCTAGCATA
AAAATAAGAAGCCTGCATTTGCAGGCTTCTTATTTTATGGCGCGCCGCCATT
ATTTTTTTGAACAATTGACAATTCATTTCTTATTTTTATTAAGTGATAGTCAA
AAGGCATAACAGTGCTGAATAGAAAGAAATTTACAGAAAGAAAATTATAGA
ATTTAGTATGATTAATTATACTCATTTATGAATGTTTAATTGAATACAAAAAA
AAATACTTGTTATGTATTCAATTACGGGTTAAAATATAGACAAGTTGAAAAAT
TTAATAAAAAAATAAGTCCTCAGCTCTTATATATTAAGCTACCAACTTAGTAT
ATAAGCCAAAACTTAAATGTGCTACCAACACATCAAGCCGTTAGAGAACTCT
ATCTATAGCAATATTTCAAATGTACCGACATACAAGAGAAACATTAACTATAT

Figure 5 (continued)

ATATTCAATTTATGAGATTATCTTAACAGATATAAATGTAAATTGCAATAAGT
AAGATTTAGAAGTTTATAGCCTTTGTGTATTGGAAGCAGTACGCAAAGGCTTT
TTTATTTGATAAAAATTAGAAGTATATTTATTTTTTCATAATTAATTTATGAAA
ATGAAAGGGGGTGAGCAAAGTGACAGAGGAAAGCAGTATCTTATCAAATAAC
AAGGTATTAGCAATATCATTATTGACTTTAGCAGTAAACATTATGACTTTTAT
AGTGCTTGTAGCTAAGTAGTACGAAAGGGGGAGCTTTAAAAAGCTCCTTGGA
ATACATAGAATTCATAAATTAATTTATGAAAGAAGGGCGTATATGAAAACT
TGTAAAAATTGCAAAGAGTTTATTAAAGATACTGAAATATGCAAAATACATTC
GTTGATGATTCATGATAAACAGTAGCAACCTATTGCAGTAAATACAATGAGT
CAAGATGTTTACATAAAGGGAAAGTCCAATGTATTAATTGTTCAAAGATGAA
CCGATATGGATGGTGTGCCATAAAAATGAGATGTTTACAGAGGAAGAACAG
AAAAAAGAACGTACATGCATTAAATATTATGCAAGGAGCTTTAAAAAAGCTC
ATGTAAAGAAGAGTAAAAAGAAAAAATAATTTATTTATTAATTTAATATTGA
GAGTGCCGACACAGTATGCACTAAAAAATATATCTGTGGTGTAGTGAGCCGA
TACAAAAGGATAGTCACTCGCATTTTCATAATACATCTTATGTTATGATTATG
TGTCGGTGGGACTTCACGACGAAAACCCACAATAAAAAAGAGTTCGGGGTA
GGGTTAAGCATAGTTGAGGCAACTAAACAATCAAGCTAGGATATGCAGTAGC
AGACCGTAAGGTCGTTGTTTAGGTGTGTTGTAATACATACGCTATTAAGATGT
AAAAATACGGATACCAATGAAGGGAAAAGTATAATTTTTGGATGTAGTTTGTT
TGTTCATCTATGGGCAAACTACGTCCAAAGCCGTTTCCAAATCTGCTAAAAAG
TATATCCTTTCTAAAATCAAAGTCAAGTATGAAATCATAAATAAAGTTTAATT
TTGAAGTTATTATGATATTATGTTTTTCTATTAAAATAAATTAAGTATATAGAA
TAGTTTAATAATAGTATATACTTAATGTGATAAGTGTCTGACAGTGTCACAGA
AAGGATGATTGTTATGGATTATAAGCGGCCGGCCGAAGCAAACTTAAGAGTG
TGTTGATAGTGCAGTATCTTAAAATTTTGTATAATAGGAATTGAAGTTAAATT
AGATGCTAAAAATTTGTAATTAAGAAGGAGTGATTACATGAACAAAAATATA
AAATATTCTCAAAACTTTTAACGAGTGAAAAAGTACTCAACCAAATAATAA
AACAATTGAATTTAAAAGAAACCGATACCGTTTACGAAATTGGAACAGGTAA
AGGGCATTTAACGACGAAACTGGCTAAAATAAGTAAACAGGTAACGTCTATT
GAATTAGACAGTCATCTATTCAACTTATCGTCAGAAAAATTAAAACTGAATAC
TCGTGTCACTTTAATTCACCAAGATATTCTACAGTTTCAATTCCCTAACAAAC
AGAGGTATAAAATTGTTGGGAGTATTCCTTACCATTTAAGCACACAAATTATT
AAAAAAGTGGTTTTTGAAAGCCATGCGTCTGACATCTATCTGATTGTTGAAGA
AGGATTCTACAAGCGTACCTTGGATATTCACCGAACACTAGGGTTGCTCTTGC

Figure 5 (continued)

ACACTCAAGTCTCGATTCAGCAATTGCTTAAGCTGCCAGCGGAATGCTTTCAT
CCTAAACCAAAAGTAAACAGTGTCTTAATAAAACTTACCCGCCATACCACAG
ATGTTCCAGATAAATATTGGAAGCTATATACGTACTTTGTTTCAAAATGGGTC
AATCGAGAATATCGTCAACTGTTTACTAAAAATCAGTTTCATCAAGCAATGAA
ACACGCCAAAGTAAACAATTTAAGTACCGTTACTTATGAGCAAGTATTGTCTA
TTTTTAATAGTTATCTATTATTTAACGGGAGGAAATAATTCTATGAGTCGCTTT
TGTAAATTTGGAAAGTTACACGTTACTAAAGGGAATGTGTTTAAACTCCTTTT
TGATAATCTCATGACCAAAATCCCTTAACGTGAGTTTTCGTTCCACTGAGCGT
CAGACCCCGTAGAAAGATCAAAGGATCTTCTTGAGATCCTTTTTTTCTGCGC
GTAATCTGCTGCTTGCAAACAAAAAACCACCGCTACCAGCGGTGGTTTGTTT
GCCGGATCAAGAGCTACCAACTCTTTTTCCGAAGGTAACTGGCTTCAGCAGAG
CGCAGATACCAAATACTGTTCTTCTAGTGTAGCCGTAGTTAGGCCACCACTTC
AAGAACTCTGTAGCACCGCCTACATACCTCGCTCTGCTAATCCTGTTACCAGT
GGCTGCTGCCAGTGGCGATAAGTCGTGTCTTACCGGGTTGGACTCAAGACGAT
AGTTACCGGATAAGGCGCAGCGGTCGGGCTGAACGGGGGGTTCGTGCACACA
GCCCAGCTTGGAGCGAACGACCTACACCGAACTGAGATACCTACAGCGTGAG
CTATGAGAAAGCGCCACGCTTCCCGAAGGGAGAAAGGCGGACAGGTATCCGG
TAAGCGGCAGGGTCGGAACAGGAGAGCGCACGAGGGAGCTTCCAGGGGGAA
ACGCCTGGTATCTTTATAGTCCTGTCGGGTTTCGCCACCTCTGACTTGAGCGTC
GATTTTGTGATGCTCGTCAGGGGGGCGGAGCCTATGGAAAAACGCCAGCAA
CGCGGCCTTTTACGGTTCCTGGCCTTTTGCTGGCCTTTTGCTCACATGTTCTT
TCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAG
GAAGCGGAAGAGCGCCCAATACGCAGGGCCCCCTGCTTCGGGGTCATTATAG
CGATTTTTTCGGTATATCCATCCTTTTCGCACGATATACAGGATTTTGCCAAA
GGGTTCGTGTAGACTTTCCTTGGTGTATCCAACGGCGTCAGCCGGGCAGGATA
GGTGAAGTAGGCCCACCCGCGAGCGGGTGTTCCTTCTTCACTGTCCCTTATTC
GCACCTGGCGGTGCTCAACGGGAATCCTGCTCTGCGAGGCTGGCCGGCTACC
GCCGGCGTAACAGATGAGGGCAAGCGGATGGCTGATGAAACCAAGCCAACCA
GGAAGGGCAGCCCACCTATCAAGGTGTACTGCCTTCCAGACGAACGAAGAGC
GATTGAGGAAAGGCGGCGGCGGCCGGCATGAGCCTGTCGGCCTACCTGCTG
GCCGTCGGCCAGGGCTACAAAATCACGGGCGTCGTGGACTATGAGCACGTCC
GCGAGCTGGCCCGCATCAATGGCGACCTGGGCCGCCTGGGCGGCCTGCTGAA
ACTCTGGCTCACCGACGACCCGCGCACGGCGCGGTTCGGTGATGCCACGATCC

Figure 5 (continued)

TCGCCCTGCTGGCGAAGATCGAAGAGAAGCAGGACGAGCTTGGCAAGGTCAT
GATGGGCGTGGTCCGCCCGAGGGCAGAGCCATGACTTTTTAGCCGCTAAAA
CGGCCGGGGGGTGCGCGTGATTGCCAAGCACGTCCCCATGCGCTCCATCAAG
AAGAGCGACTTCGCGGAGCTGGTGAAGTACATCACCGACGAGCAAGGCAAGA
CCGATCGGGCCC

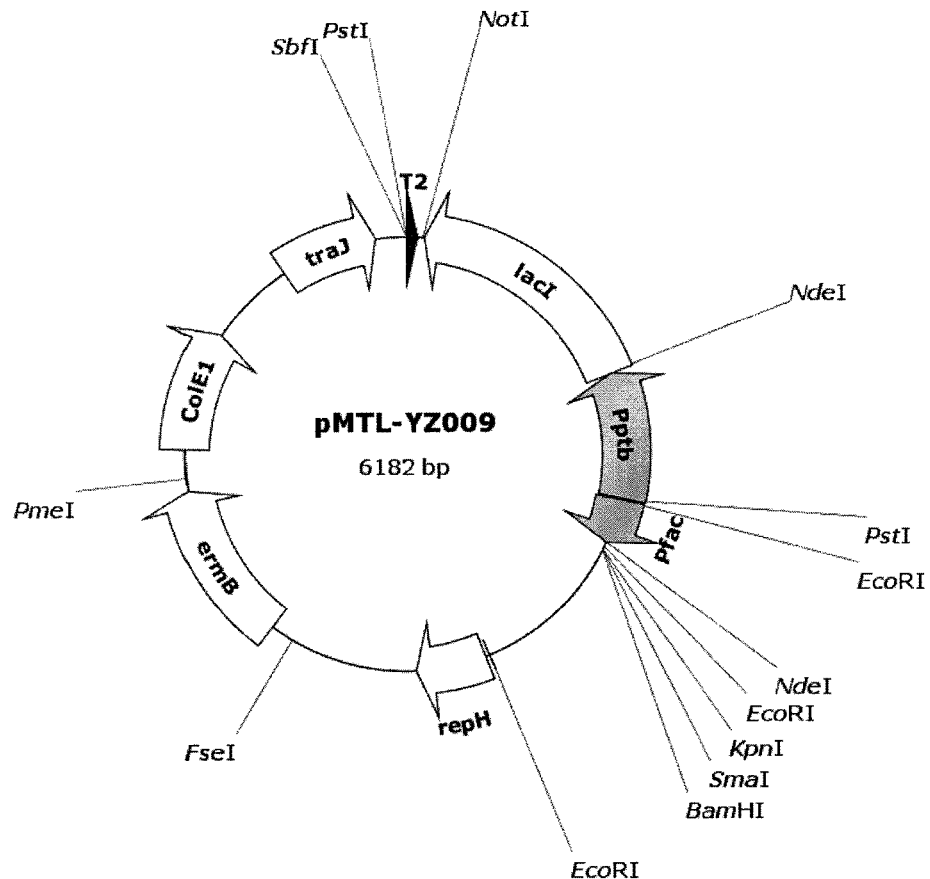

Figure 6.
CCTGCAGGATAAAAAAATTGTAGATAAATTTTATAAAATAGTTTTATCTACAA
TTTTTTTATCAGGAAACAGCTATGACCGCGGCCGCGCTCACTGCCCGCTTTCC
AGTCGGGAAACCTGTCGTGCCAGCTGCATTAATGAATCGGCCAACGCGCGGG
GAGAGGCGGTTTGCGTATTGGGCGCCAGGGTGGTTTTTCTTTTCACCAGTGAG
ACGGGCAACAGCTGATTGCCCTTCACCGCCTGGCCCTGAGAGAGTTGCAGCA
AGCGGTCCACGCTGGTTTGCCCCAGCAGGCGAAAATCCTGTTTGATGGTGGTT
AACGGCGGGATATAACATGAGCTGTCTTCGGTATCGTCGTATCCCACTACCGA
GATATCCGCACCAACGCGCAGCCCGGACTCGGTAATGGCGCGCATTGCGCCC
AGCGCCATCTGATCGTTGGCAACCAGCATCGCAGTGGGAACGATGCCCTCATT
CAGCATTTGCATGGTTTGTTGAAAACCGGACATGGCACTCCAGTCGCCTTCCC
GTTCCGCTATCGGCTGAATTTGATTGCGAGTGAGATATTTATGCCAGCCAGCC

Figure 6 (continued)

AGACGCAGACGCGCCGAGACAGAACTTAATGGGCCCGCTAACAGCGCGATTT
GCTGGTGACCCAATGCGACCAGATGCTCCACGCCCAGTCGCGTACCGTCTTCA
TGGGAGAAAATAATACTGTTGATGGGTGTCTGGTCAGAGACATCAAGAAATA
ACGCCGGAACATTAGTGCAGGCAGCTTCCACAGCAATGGCATCCTGGTCATCC
AGCGGATAGTTAATGATCAGCCCACTGACGCGTTGCGCGAGAAGATTGTGCA
CCGCCGYTTTACAGGCTTCGACGCCGCTTCGTTCTACCATCGACACCACCACG
CTGGCACCCAGTTGATCGGCGCGAGATTTAATCGCCGCGACAATTTGCGACGG
CGCGTGCAGGGCCAGACTGGAGGTGGCAACGCCAATCAGCAACGACTGTTTG
CCCGCCAGTTGTTGTGCCACGCGGTTGGGAATGTAATTCAGCTCCGCCATCGC
CGCTTCCACTTTTTCCCGCGTTTTCGCAGAAACGTGGCTGGCCTGGTTCACCAC
GCGGGAAACGGTCTGATAAGAGACACCGGCATACTCTGCGACATCGTATAAC
GTTACTGGTTTCATATGTTGCACCTCTACTTTAATAATTTTAACTTTTATATA
TGATTAATTTAATTGTTTGTTAAATTTATATCAATCAATGCTATGAATATTTCT
TTATACCTTATTGTAACAAAAAATATTGGAAATGTTGAATTTTCAGAATATT
ATTTTTATTATATTATTAATTTTATATATTCATTTTTATAAGATTTCACAACAC
GAACGTAATATAATATATCTTCCTCATCTTCTGAAAAGATTATACTAATTCTAT
TCATGTTACTTATAATCTTATTTTGGTAAATCGAATTTTTCAATTATATGTTCG
GCAACCTTTATCCCATCAACAGCCGCTGATATTATACCACCTGCAAATCCTGC
CCCTTCTCCAGTTGGATAAAGTCCGCATACATTTATACTTTCAAGTGAAGCAT
TTCTATTCAATCTAACTGGTGCTGATGTTCTTGTCTCAATTCCCGTTAAAATTG
CATCTTCTCTTGCATACCCTTTTATCTTTTATCAAAATTTATAATTCCTTCTTT
AAGAGCCTCTACAACATAATCAGGTAAACATTCTTTTAATTCCCTGAATTATC
TGCAGAGAATTCCCCGGATCGAGATAGTATATGATGCATATTCTTTAAATATA
GATAAAGTTATAGAAGCAATAGAAGATTTAGGATTTACTGTAATATAAATTAC
ACTTTTAAAAGTTTAAAAACATGATACAATAAGTTATGGTTGGAATTGTTAT
CCGCTCACAATTCCAACTTATGATTAAAATTTTAAGGAGGTGTATTTCATATG
ACCATGATTACGAATTCGAGCTCGGTACCCGGGGATCCGCGCCGCCATTATTT
TTTTGAACAATTGACAATTCATTTCTTATTTTTATTAAGTGATAGTCAAAAGG
CATAACAGTGCTGAATAGAAAGAAATTTACAGAAAGAAAATTATAGAATTT
AGTATGATTAATTATACTCATTTATGAATGTTTAATTGAATACAAAAAAAAT
ACTTGTTATGTATTCAATTACGGGTTAAAATATAGACAAGTTGAAAAATTTAA
TAAAAAATAAGTCCTCAGCTCTTATATATTAAGCTACCAACTTAGTATATAA
GCCAAAACTTAAATGTGCTACCAACACATCAAGCCGTTAGAGAACTCTATCTA
TAGCAATATTTCAAATGTACCGACATACAAGAGAAACATTAACTATATATT

Figure 6 (continued)

CAATTTATGAGATTATCTTAACAGATATAAATGTAAATTGCAATAAGTAAGAT
TTAGAAGTTTATAGCCTTTGTGTATTGGAAGCAGTACGCAAAGGCTTTTTTAT
TTGATAAAAATTAGAAGTATATTTATTTTTCATAATTAATTTATGAAAATGA
AAGGGGGTGAGCAAAGTGACAGAGGAAAGCAGTATCTTATCAAATAACAAG
GTATTAGCAATATCATTATTGACTTTAGCAGTAAACATTATGACTTTTATAGT
GCTTGTAGCTAAGTAGTACGAAAGGGGGAGCTTTAAAAAGCTCCTTGGAATA
CATAGAATTCATAAATTAATTTATGAAAAGAAGGGCGTATATGAAAACTTGT
AAAAATTGCAAAGAGTTTATTAAAGATACTGAAATATGCAAAATACATTCGTT
GATGATTCATGATAAACAGTAGCAACCTATTGCAGTAAATACAATGAGTCA
AGATGTTTACATAAAGGGAAAGTCCAATGTATTAATTGTTCAAAGATGAACC
GATATGGATGGTGTGCCATAAAAATGAGATGTTTTACAGAGGAAGAACAGAA
AAAAGAACGTACATGCATTAAATATTATGCAAGGAGCTTTAAAAAAGCTCAT
GTAAAGAAGAGTAAAAAGAAAAAATAATTTATTTATTAATTTAATATTGAGA
GTGCCGACACAGTATGCACTAAAAAATATATCTGTGGTGTAGTGAGCCGATA
CAAAAGGATAGTCACTCGCATTTTCATAATACATCTTATGTTATGATTATGTG
TCGGTGGGACTTCACGACGAAAACCCACAATAAAAAAAGAGTTCGGGGTAGG
GTTAAGCATAGTTGAGGCAACTAAACAATCAAGCTAGGATATGCAGTAGCAG
ACCGTAAGGTCGTTGTTTAGGTGTGTTGTAATACATACGCTATTAAGATGTAA
AAATACGGATACCAATGAAGGGAAAAGTATAATTTTTGGATGTAGTTTGTTTG
TTCATCTATGGGCAAACTACGTCCAAAGCCGTTTCCAAATCTGCTAAAAAGTA
TATCCTTTCTAAAATCAAAGTCAAGTATGAAATCATAAATAAAGTTTAATTTT
GAAGTTATTATGATATTATGTTTTTCTATTAAAATAAATTAAGTATATAGAAT
AGTTTAATAATAGTATATACTTAATGTGATAAGTGTCTGACAGTGTCACAGAA
AGGATGATTGTTATGGATTATAAGCGGCCGGCCGAAGCAAACTTAAGAGTGT
GTTGATAGTGCAGTATCTTAAAATTTTGTATAATAGGAATTGAAGTTAAATTA
GATGCTAAAAATTTGTAATTAAGAAGGAGTGATTACATGAACAAAAATATAA
AATATTCTCAAAACTTTTTAACGAGTGAAAAAGTACTCAACCAAATAATAAA
ACAATTGAATTTAAAAGAAACCGATACCGTTTACGAAATTGGAACAGGTAAA
GGGCATTTAACGACGAAACTGGCTAAAATAAGTAAACAGGTAACGTCTATTG
AATTAGACAGTCATCTATTCAACTTATCGTCAGAAAAATTAAAACTGAATACT
CGTGTCACTTTAATTCACCAAGATATTCTACAGTTTCAATTCCCTAACAAACA
GAGGTATAAAATTGTTGGGAGTATTCCTTACCATTTAAGCACACAAATTATTA
AAAAGTGGTTTTTGAAAGCCATGCGTCTGACATCTATCTGATTGTTGAAGAA

Figure 6 (continued)

GGATTCTACAAGCGTACCTTGGATATTCACCGAACACTAGGGTTGCTCTTGCA
CACTCAAGTCTCGATTCAGCAATTGCTTAAGCTGCCAGCGGAATGCTTTCATC
CTAAACCAAAAGTAAACAGTGTCTTAATAAAACTTACCCGCCATACCACAGA
TGTTCCAGATAAATATTGGAAGCTATATACGTACTTTGTTTCAAAATGGGTCA
ATCGAGAATATCGTCAACTGTTTACTAAAAATCAGTTTCATCAAGCAATGAAA
CACGCCAAAGTAAACAATTTAAGTACCGTTACTTATGAGCAAGTATTGTCTAT
TTTTAATAGTTATCTATTATTTAACGGGAGGAAATAATTCTATGAGTCGCTTTT
GTAAATTTGGAAAGTTACACGTTACTAAAGGGAATGTGTTTAAACTCCTTTTT
GATAATCTCATGACCAAAATCCCTTAACGTGAGTTTTCGTTCCACTGAGCGTC
AGACCCCGTAGAAAGATCAAAGGATCTTCTTGAGATCCTTTTTTTCTGCGCG
TAATCTGCTGCTTGCAAACAAAAAAACCACCGCTACCAGCGGTGGTTTGTTTG
CCGGATCAAGAGCTACCAACTCTTTTTCCGAAGGTAACTGGCTTCAGCAGAGC
GCAGATACCAAATACTGTTCTTCTAGTGTAGCCGTAGTTAGGCCACCACTTCA
AGAACTCTGTAGCACCGCCTACATACCTCGCTCTGCTAATCCTGTTACCAGTG
GCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAG
CCCAGCTTGGAGCGAACGACCTACACCGAACTGAGATACCTACAGCGTGAGC
TATGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAA
CGCCTGGTATCTTTATAGTCCTGTCGGGTTTCGCCACCTCTGACTTGAGCGTCG
ATTTTTGTGATGCTCGTCAGGGGGGCGGAGCCTATGGAAAAACGCCAGCAAC
GCGGCCTTTTTACGGTTCCTGGCCTTTTGCTGGCCTTTTGCTCACATGTTCTTT
CCTGCGTTATCCCCTGATTCTGTGGATAACCGTATTACCGCCTTTGAGTGAGCT
GATACCGCTCGCCGCAGCCGAACGACCGAGCGCAGCGAGTCAGTGAGCGAGG
AAGCGGAAGAGCGCCCAATACGCAGGGCCCCTGCTTCGGGGTCATTATAGC
GATTTTTTCGGTATATCCATCCTTTTCGCACGATATACAGGATTTTGCCAAAG
GGTTCGTGTAGACTTTCCTTGGTGTATCCAACGGCGTCAGCCGGGCAGGATAG
GTGAAGTAGGCCCACCCGCGAGCGGGTGTTCCTTCTTCACTGTCCCTTATTCG
CACCTGGCGGTGCTCAACGGGAATCCTGCTCTGCGAGGCTGGCCGGCTACCGC
CGGCGTAACAGATGAGGGCAAGCGGATGGCTGATGAAACCAAGCCAACCAG
GAAGGGCAGCCCACCTATCAAGGTGTACTGCCTTCCAGACGAACGAAGAGCG
ATTGAGGAAAGGCGGCGGCGGCCGGCATGAGCCTGTCGGCCTACCTGCTGG
CCGTCGGCCAGGGCTACAAAATCACGGGCGTCGTGGACTATGAGCACGTCCG
CGAGCTGGCCCGCATCAATGGCGACCTGGGCCGCCTGGGCGGCCTGCTGAAA

Figure 6 (continued)
CTCTGGCTCACCGACGACCCGCGCACGGCGCGGTTCGGTGATGCCACGATCCT
CGCCCTGCTGGCGAAGATCGAAGAGAAGCAGGACGAGCTTGGCAAGGTCATG
ATGGGCGTGGTCCGCCCGAGGGCAGAGCCATGACTTTTTAGCCGCTAAAAC
GGCCGGGGGGTGCGCGTGATTGCCAAGCACGTCCCCATGCGCTCCATCAAGA
AGAGCGACTTCGCGGAGCTGGTGAAGTACATCACCGACGAGCAAGGCAAGAC
CGATCGGGCCC

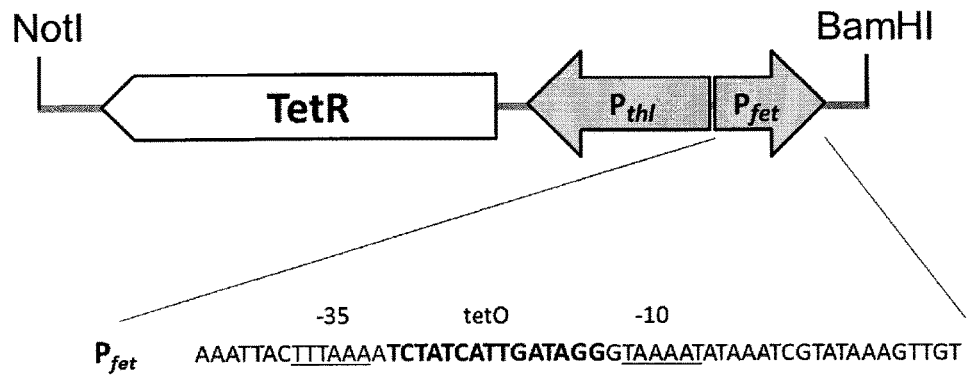

Figure 9.

GCGGCCGCGGCGCCAAGCTTAGAAAAATATAAATAAGAAGTAGCTTTAAGAG
AATTAAATTATTAAGAAAAGCAAAGGTGTTTAAAAAATAAATTTTTAAACAC
CTTTGCTTTTCTTAAATTATAAATAAGATAAAAAAGAATCCTGAATAAAATAA
AAAGGGGTGTCTCAAAATTTTATTTTGAGACGACCCCTTTTTATTCTATATGTC
GATGCTATAGCTGAGATCGTGGAATTCTTGTTAGCTACCAGATTCACATTTAA
GTTGTTTCTCTAAACCACAGATTATCAATTCAAGTCCAAAAAGAAATGCTGGT
TCTGCGCCTTGATGATCAAATAACTCTATTGCTTGTCTTAACAATGGAGGCAT
TGAATCTGTTGTTGGTGTTTCTCTTTCCTCTTTTGCAACTTGATGTTCTTGATCC
TCCAATACGCAACCTAAAGTAAAATGTCCTACAGCACTTAGTGCGTATAAGGC
ATTTTCTAAACTAAAACCCTGTTGACATAAGAATGCTAATTGATTTCTAATG
TTTCATATTGTTTTTCAGTTGGTCTAGTTCCTAAATGTACTTTAGCCCCATCTC
TATGTGATAATAGAGCACAACGAAAAGATTTAGCGTTATTCCTAAGAAAATCT
TGCCATGATTCACCTTCTAAAGGACAAAAGTGAGTGTGATGTCTATCTAACAT
TTCAATAGCTAAGGCGTCAAGTAAAGCTCTCTTATTCTTCACATGCCAATACA
ACGTAGGTTGTTCTACTCCAAGTTTCTGAGCTAACTTTCTTGTAGTTAGTCCTT
CTATTCCAACTTCATTTAGTAATTCCAATGCACTATTGATAACTTTACTTTTAT
CAAGTCTAGACATCATTTAATATCCTCCTCTTCAATATATTTAAGTCGACTGAT
CGGATCC

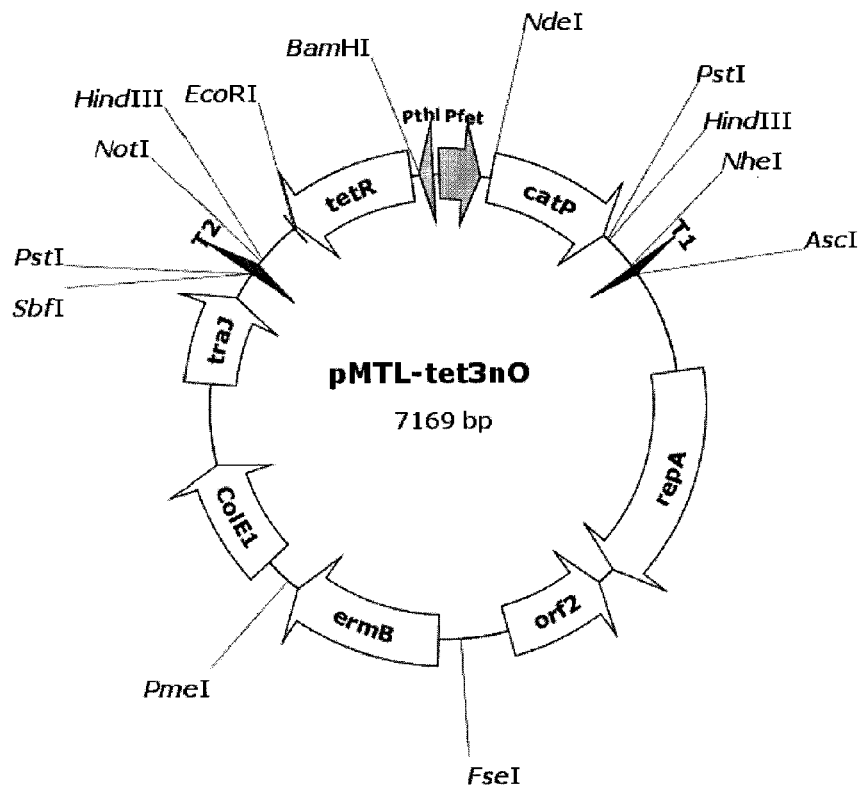

Figure 10.
AAGTAAGGAAAAAAAAGAAGTAAGTGTTATATATGATGATTATTTTGTAGAT
GTAGATAGGATAATAGAATCCATAGAAAATATAGGTTATACAGTTATATAAA
AATTACTTTAAAATCTATCATTGATAGGGTAAAATATAAATCGTATAAAGTTG
TGTAATTTTTAAGGAGGTGTGTTACAGACGTCCGCGAGAGACCTTAAATATAT
TGAAGAGGAGGAAATACATATGGTATTTGAAAAAATTGATAAAAATAGTTGG
AACAGAAAAGAGTATTTTGACCACTACTTTGCAAGTGTACCTTGTACCTACAG
CATGACCGTTAAAGTGGATATCACACAAATAAAGGAAAAGGGAATGAAACTA
TATCCTGCAATGCTTTATTATATTGCAATGATTGTAAACCGCCATTCAGAGTTT
AGGACGGCAATCAATCAAGATGGTGAATTGGGGATATATGATGAGATGATAC
CAAGCTATACAATATTTCACAATGATACTGAAACATTTTCCAGCCTTTGGACT
GAGTGTAAGTCTGACTTTAAATCATTTTTAGCAGATTATGAAAGTGATACGCA Figure 10 (continued)

ACGGTATGGAAACAATCATAGAATGGAAGGAAAGCCAAATGCTCCGGAAAAC
ATTTTTAATGTATCTATGATACCGTGGTCAACCTTCGATGGCTTTAATCTGAAT
TTGCAGAAAGGATATGATTATTTGATTCCTATTTTTACTATGGGGAAATATTA
TAAAGAAGATAACAAAATTATACTTCCTTTGGCAATTCAAGTTCATCACGCAG
TATGTGACGGATTTCACATTTGCCGTTTTGTAAACGAATTGCAGGAATTGATA
AATAGTTAAACGCGTCCATGGAGATCTCGAGGCCTGCAGACATGCAAGCTTG
GCACTGGCCGTCGTTTTACAACGTCGTGACTGGGAAAACCCTGGCGTTACCCA
ACTTAATCGCCTTGCAGCACATCCCCCTTTCGCCAGCTGGCGTAATAGCGAAG
AGGCCCGCACCGATCGCCCTTCCCAACAGTTGCGCAGCCTGAATGGCGAATG
GCGCTAGCATAAAAATAAGAAGCCTGCATTTGCAGGCTTCTTATTTTATGGC
GCGCCGTTCTGAATCCTTAGCTAATGGTTCAACAGGTAACTATGACGAAGATA
GCACCCTGGATAAGTCTGTAATGGATTCTAAGGCATTTAATGAAGACGTGTAT
ATAAAATGTGCTAATGAAAAGAAAATGCGTTAAAAGAGCCTAAAATGAGTT
CAAATGGTTTTGAAATTGATTGGTAGTTTAATTTAATATATTTTTCTATTGGC
TATCTCGATACCTATAGAATCTTCTGTTCACTTTTGTTTTGAAATATAAAAAG
GGGCTTTTTAGCCCCTTTTTTTAAAACTCCGGAGGAGTTTCTTCATTCTTGAT
ACTATACGTAACTATTTTCGATTTGACTTCATTGTCAATTAAGCTAGTAAAATC
AATGGTTAAAAAACAAAAACTTGCATTTTTCTACCTAGTAATTTATAATTTT
AAGTGTCGAGTTTAAAAGTATAATTTACCAGGAAAGGAGCAAGTTTTTAATA
AGGAAAAATTTTTCCTTTTAAAATTCTATTTCGTTATATGACTAATTATAATCA
AAAAAATGAAAATAAACAAGAGGTAAAAACTGCTTTAGAGAAATGTACTGAT
AAAAAAAGAAAAAATCCTAGATTTACGTCATACATAGCACCTTTAACTACTA
AGAAAAATATTGAAAGGACTTCCACTTGTGGAGATTATTTGTTTATGTTGAGT
GATGCAGACTTAGAACATTTTAAATTACATAAAGGTAATTTTTGCGGTAATAG
ATTTTGTCCAATGTGTAGTTGGCGACTTGCTTGTAAGGATAGTTTAGAAATAT
CTATTCTTATGGAGCATTTAAGAAAAGAAGAAAATAAAGAGTTTATATTTTA
ACTCTTACAACTCCAAATGTAAAAAGTTATGATCTTAATTATTCTATTAAACA
ATATAATAAATCTTTTAAAAAATTAATGGAGCGTAAGGAAGTTAAGGATATA
ACTAAAGGTTATATAAGAAAATTAGAAGTAACTTACCAAAAGGAAAATACA
TAACAAAGGATTTATGGAAATAAAAAAGATTATTATCAAAAAAAGGACT
TGAAATTGGTGATTTAGAACCTAATTTTGATACTTATAATCCTCATTTTCATGT
AGTTATTGCAGTTAATAAAAGTTATTTACAGATAAAATTATTATATAAATC
GAGAAAGATGGTTGGAATTATGGAAGTTTGCTACTAAGGATGATTCTATAACT
CAAGTTGATGTTAGAAAAGCAAAAATTAATGATTATAAAGAGGTTTACGAAC

Figure 10 (continued)

TTGCGAAATATTCAGCTAAAGACACTGATTATTTAATATCGAGGCCAGTATTT
GAAATTTTTATAAAGCATTAAAAGGCAAGCAGGTATTAGTTTTTAGTGGATT
TTTTAAAGATGCACACAAATTGTACAAGCAAGGAAAACTTGATGTTTATAAA
AAGAAAGATGAAATTAAATATGTCTATATAGTTTATTATAATTGGTGCAAAAA
ACAATATGAAAAACTAGAATAAGGGAACTTACGGAAGATGAAAAGAAGA
ATTAAATCAAGATTTAATAGATGAAATAGAAATAGATTAAAGTGTAACTATA
CTTTATATATATGATTAAAAAATAAAAACAACAGCCTATTAGGTTGTTG
TTTTTATTTTCTTTATTAATTTTTTAATTTTTAGTTTTTAGTTCTTTTTAAAA
TAAGTTTCAGCCTCTTTTTCAATATTTTTAAAGAAGGAGTATTTGCATGAATT
GCCTTTTTCTAACAGACTTAGGAAATATTTAACAGTATCTTCTTGCGCCGGT
GATTTTGGAACTTCATAACTTACTAATTTATAATTATTATTTTCTTTTTTAATTG
TAACAGTTGCAAAAGAAGCTGAACCTGTTCCTTCAACTAGTTTATCATCTTCA
ATATAATATTCTTGACCTATATAGTATAAATATATTTTATTATATTTTTACTT
TTTTCTGAATCTATTATTTTATAATCATAAAAAGTTTTACCACCAAAAGAAGG
TTGTACTCCTTCTGGTCCAACATATTTTTTACTATATTATCTAAATAATTTTTG
GGAACTGGTGTTGTAATTTGATTAATCGAACAACCAGTTATACTTAAAGGAAT
TATAACTATAAAAATATATAGGATTATCTTTTTAAATTTCATTATTGGCCTCCT
TTTTATTAAATTTATGTTACCATAAAAAGGACATAACGGGAATATGTAGAATA
TTTTTAATGTAGACAAAATTTTACATAAATATAAAGAAAGGAAGTGTTTGTTT
AAATTTTATAGCAAACTATCAAAAATTAGGGGGATAAAAATTTATGAAAAAA
AGGTTTTCGATGTTATTTTTATGTTTAACTTTAATAGTTTGTGGTTTATTTACA
AATTCGGCCGGCCGAAGCAAACTTAAGAGTGTGTTGATAGTGCAGTATCTTAA
AATTTTGTATAATAGGAATTGAAGTTAAATTAGATGCTAAAAATTTGTAATTA
AGAAGGAGTGATTACATGAACAAAAATATAAAATATTCTCAAAACTTTTTAA
CGAGTGAAAAAGTACTCAACCAAATAATAAAACAATTGAATTTAAAAGAAAC
CGATACCGTTTACGAAATTGGAACAGGTAAAGGGCATTTAACGACGAAACTG
GCTAAAATAAGTAAACAGGTAACGTCTATTGAATTAGACAGTCATCTATTCAA
CTTATCGTCAGAAAAATTAAAACTGAATACTCGTGTCACTTTAATTCACCAAG
ATATTCTACAGTTTCAATTCCCTAACAAACAGAGGTATAAAATTGTTGGGAGT
ATTCCTTACCATTTAAGCACACAAATTATTAAAAAGTGGTTTTTGAAAGCCA
TGCGTCTGACATCTATCTGATTGTTGAAGAAGGATTCTACAAGCGTACCTTGG
ATATTCACCGAACACTAGGGTTGCTCTTGCACACTCAAGTCTCGATTCAGCAA
TTGCTTAAGCTGCCAGCGGAATGCTTTCATCCTAAACCAAAAGTAAACAGTGT
CTTAATAAAACTTACCCGCCATACCACAGATGTTCCAGATAAATATTGGAAGC

Figure 10 (continued)

TATATACGTACTTTGTTTCAAAATGGGTCAATCGAGAATATCGTCAACTGTTT
ACTAAAAATCAGTTTCATCAAGCAATGAAACACGCCAAAGTAAACAATTTAA
GTACCGTTACTTATGAGCAAGTATTGTCTATTTTAATAGTTATCTATTATTTA
ACGGGAGGAAATAATTCTATGAGTCGCTTTTGTAAATTTGGAAAGTTACACGT
TACTAAAGGGAATGTGTTTAAACTCCTTTTTGATAATCTCATGACCAAAATCC
CTTAACGTGAGTTTTCGTTCCACTGAGCGTCAGACCCCGTAGAAAGATCAAA
GGATCTTCTTGAGATCCTTTTTTTCTGCGCGTAATCTGCTGCTTGCAAACAAAA
AAACCACCGCTACCAGCGGTGGTTTGTTTGCCGGATCAAGAGCTACCAACTCT
TTTTCCGAAGGTAACTGGCTTCAGCAGAGCGCAGATACCAAATACTGTTCTTC
TAGTGTAGCCGTAGTTAGGCCACCACTTCAAGAACTCTGTAGCACCGCCTACA
TACCTCGCTCTGCTAATCCTGTTACCAGTGGCTGCTGCCAGTGGCGATAAGTC
GTGTCTTACCGGGTTGGACTCAAGACGATAGTTACCGGATAAGGCGCAGCGG
TCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCC
CGAAGGGAGAAAGGCGGACAGGTATCCGGTAAGCGGCAGGGTCGGAACAGG
AGAGCGCACGAGGGAGCTTCCAGGGGGAAACGCCTGGTATCTTTATAGTCCT
GTCGGGTTTCGCCACCTCTGACTTGAGCGTCGATTTTGTGATGCTCGTCAGG
GGGGCGGAGCCTATGGAAAAACGCCAGCAACGCGGCCTTTTACGGTTCCTG
GCCTTTTGCTGGCCTTTTGCTCACATGTTCTTTCCTGCGTTATCCCCTGATTCTG
TGGATAACCGTATTACCGCCTTTGAGTGAGCTGATACCGCTCGCCGCAGCCGA
ACGACCGAGCGCAGCGAGTCAGTGAGCGAGGAAGCGGAAGAGCGCCCAATA
CGCAGGGCCCCTGCTTCGGGGTCATTATAGCGATTTTTCGGTATATCCATC
CTTTTTCGCACGATATACAGGATTTTGCCAAAGGGTTCGTGTAGACTTTCCTTG
GTGTATCCAACGGCGTCAGCCGGGCAGGATAGGTGAAGTAGGCCCACCCGCG
AGCGGGTGTTCCTTCTTCACTGTCCCTTATTCGCACCTGGCGGTGCTCAACGG
GAATCCTGCTCTGCGAGGCTGGCCGGCTACCGCCGGCGTAACAGATGAGGGC
AAGCGGATGGCTGATGAAACCAAGCCAACCAGGAAGGGCAGCCCACCTATCA
AGGTGTACTGCCTTCCAGACGAACGAAGAGCGATTGAGGAAAAGGCGGCGGC
GGCCGGCATGAGCCTGTCGGCCTACCTGCTGGCCGTCGGCCAGGGCTACAAA
ATCACGGGCGTCGTGGACTATGAGCACGTCCGCGAGCTGGCCCGCATCAATG
GCGACCTGGGCCGCCTGGGCGGCCTGCTGAAACTCTGGCTCACCGACGACCC
GCGCACGGCGCGGTTCGGTGATGCCACGATCCTCGCCCTGCTGGCGAAGATC
GAAGAGAAGCAGGACGAGCTTGGCAAGGTCATGATGGGCGTGGTCCGCCCGA
GGGCAGAGCCATGACTTTTTAGCCGCTAAAACGGCCGGGGGGTGCGCGTGA

Figure 10 (continued)

TTGCCAAGCACGTCCCCATGCGCTCCATCAAGAAGAGCGACTTCGCGGAGCT
GGTGAAGTACATCACCGACGAGCAAGGCAAGACCGATCGGGCCCCCTGCAGG
ATAAAAAAATTGTAGATAAATTTTATAAAATAGTTTTATCTACAATTTTTTAT
CAGGAAACAGCTATGACCGCGGCCGCGGCGCCAAGCTTAGAAAAATATAAAT
AAGAAGTAGCTTTAAGAGAATTAAATTATTAAGAAAAGCAAGGTGTTTAAA
AAATAAATTTTTAAACACCTTTGCTTTTCTTAAATTATAAATAAGATAAAAA
GAATCCTGAATAAAATAAAAAGGGGTGTCTCAAAATTTTATTTTGAGACGACC
CCTTTTTATTCTATATGTCGATGCTATAGCTGAGATCGTGGAATTCTTGTTAGC
TACCAGATTCACATTTAAGTTGTTTCTCTAAACCACAGATTATCAATTCAAGT
CCAAAAAGAAATGCTGGTTCTGCGCCTTGATGATCAAATAACTCTATTGCTTG
TCTTAACAATGGAGGCATTGAATCTGTTGTTGGTGTTTCTCTTTCCTCTTTTGC
AACTTGATGTTCTTGATCCTCCAATACGCAACCTAAAGTAAAATGTCCTACAG
CACTTAGTGCGTATAAGGCATTTTCTAAACTAAAACCCTGTTGACATAAGAAT
GCTAATTGATTTCTAATGTTTCATATTGTTTTCAGTTGGTCTAGTTCCTAAA
TGTACTTTAGCCCCATCTCTATGTGATAATAGAGCACAACGAAAAGATTTAGC
GTTATTCCTAAGAAAATCTTGCCATGATTCACCTTCTAAAGGACAAAAGTGAG
TGTGATGTCTATCTAACATTTCAATAGCTAAGGCGTCAAGTAAAGCTCTCTTA
TTCTTCACATGCCAATACAACGTAGGTTGTTCTACTCCAAGTTTCTGAGCTAA
CTTTCTTGTAGTTAGTCCTTCTATTCCAACTTCATTTAGTAATTCCAATGCACT
ATTGATAACTTTACTTTTATCAAGTCTAGACATCATTTAATATCCTCCTCTTCA
ATATATTTAAGTCGACTGATCGGATCCAATTTATACGTTTTCTCTAACAACTTA
ATTATACCCACTATTATTATTTTTATCAATATAGAGCTCCCATGGCGGCCGGTC
GATATCGATGTGTAGTAGCCTGTGAAAT

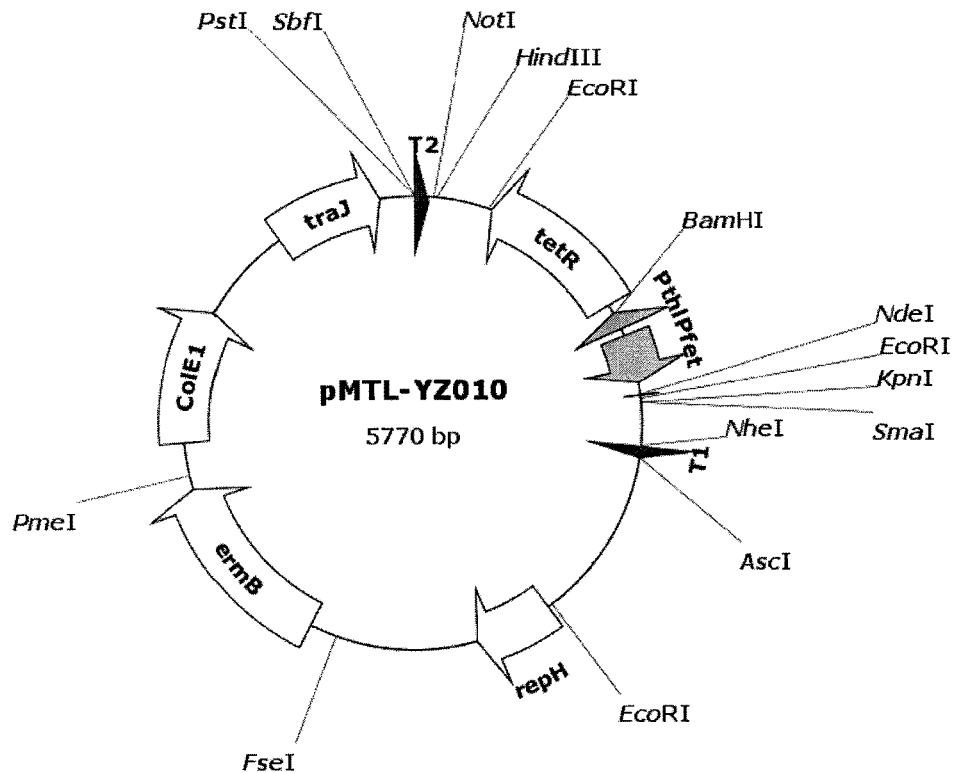

Figure 12.
CCTGCAGGATAAAAAAATTGTAGATAAATTTTATAAAATAGTTTTATCTACAA
TTTTTTTATCAGGAAACAGCTATGACCGCGGCCGCGGCGCCAAGCTTAGAAAA
ATATAAATAAGAAGTAGCTTTAAGAGAATTAAATTATTAAGAAAAGCAAAGG
TGTTTAAAAAATAAATTTTTAAACACCTTTGCTTTTCTTAAATTATAAATAAGA
TAAAAAAGAATCCTGAATAAAATAAAAAGGGGTGTCTCAAAATTTTATTTTG
AGACGACCCCTTTTTATTCTATATGTCGATGCTATAGCTGAGATCGTGGAATT
CTTGTTAGCTACCAGATTCACATTTAAGTTGTTTCTCTAAACCACAGATTATCA
ATTCAAGTCCAAAAAGAAATGCTGGTTCTGCGCCTTGATGATCAAATAACTCT
ATTGCTTGTCTTAACAATGGAGGCATTGAATCTGTTGTTGGTGTTTCTCTTTCC
TCTTTTGCAACTTGATGTTCTTGATCCTCCAATACGCAACCTAAAGTAAAATG
TCCTACAGCACTTAGTGCGTATAAGGCATTTTCTAAACTAAAACCCTGTTGAC
ATAAGAATGCTAATTGATTTTCTAATGTTTCATATTGTTTTTCAGTTGGTCTAG
TTCCTAAATGTACTTTAGCCCCATCTCTATGTGATAATAGAGCACAACGAAAA
GATTTAGCGTTATTCCTAAGAAAATCTTGCCATGATTCACCTTCTAAAGGACA
AAAGTGAGTGTGATGTCTATCTAACATTTCAATAGCTAAGGCGTCAAGTAAAG

Figure 12 (continued)

CTCTCTTATTCTTCACATGCCAATACAACGTAGGTTGTTCTACTCCAAGTTTCT
GAGCTAACTTTCTTGTAGTTAGTCCTTCTATTCCAACTTCATTTAGTAATTCCA
ATGCACTATTGATAACTTTACTTTTATCAAGTCTAGACATCATTTAATATCCTC
CTCTTCAATATATTTAAGTCGACTGATCGGATCCAATTTATACGTTTTCTCTAA
CAACTTAATTATACCCACTATTATTATTTTTATCAATATAGAGCTCCCATGGCG
GCCGGTCGATATCGATGTGTAGTAGCCTGTGAAATAAGTAAGGAAAAAAAG
AAGTAAGTGTTATATATGATGATTATTTTGTAGATGTAGATAGGATAATAGAA
TCCATAGAAAATATAGGTTATACAGTTATATAAAAATTACTTTAAAATCTATC
ATTGATAGGGTAAAATATAAATCGTATAAGTTGTGTAATTTTTAAGGAGGTG
TGTTACAGACGTCCGCGAGAGACCTTAAATATATTGAAGAGGAGGAAATACA
TATGACCATGATTACGAATTCGAGCTCGGTACCCGGGGATCAGCTTGGCACTG
GCCGTCGTTTTACAACGTCGTGACTGGGAAAACCCTGGCGTTACCCAACTTAA
TCGCCTTGCAGCACATCCCCCTTTCGCCAGCTGGCGTAATAGCGAAGAGGCCC
GCACCGATCGCCCTTCCCAACAGTTGCGCAGCCTGAATGGCGAATGGCGCTA
GCATAAAAATAAGAAGCCTGCATTTGCAGGCTTCTTATTTTATGGCGCGCCG
CCATTATTTTTTTGAACAATTGACAATTCATTTCTTATTTTTATTAAGTGATA
GTCAAAAGGCATAACAGTGCTGAATAGAAAGAAATTTACAGAAAAGAAAATT
ATAGAATTTAGTATGATTAATTATACTCATTTATGAATGTTTAATTGAATACA
AAAAAAAATACTTGTTATGTATTCAATTACGGGTTAAAATATAGACAAGTTGA
AAAATTTAATAAAAAAATAAGTCCTCAGCTCTTATATATTAAGCTACCAACTT
AGTATATAAGCCAAAACTTAAATGTGCTACCAACACATCAAGCCGTTAGAGA
ACTCTATCTATAGCAATATTTCAAATGTACCGACATACAAGAGAAACATTAAC
TATATATATTCAATTTATGAGATTATCTTAACAGATATAAATGTAAATTGCAA
TAAGTAAGATTTAGAAGTTTATAGCCTTTGTGTATTGGAAGCAGTACGCAAAG
GCTTTTTTATTTGATAAAAATTAGAAGTATATTTATTTTTTCATAATTAATTTA
TGAAAATGAAAGGGGGTGAGCAAAGTGACAGAGGAAAGCAGTATCTTATCAA
ATAACAAGGTATTAGCAATATCATTATTGACTTTAGCAGTAAACATTATGACT
TTTATAGTGCTTGTAGCTAAGTAGTACGAAAGGGGGAGCTTTAAAAAGCTCCT
TGGAATACATAGAATTCATAAATTAATTTATGAAAAGAAGGGCGTATATGAA
AACTTGTAAAAATTGCAAAGAGTTTATTAAAGATACTGAAATATGCAAAATA
CATTCGTTGATGATTCATGATAAAACAGTAGCAACCTATTGCAGTAAATACAA
TGAGTCAAGATGTTTACATAAAGGGAAAGTCCAATGTATTAATTGTTCAAAGA
TGAACCGATATGGATGGTGTGCCATAAAAATGAGATGTTTTACAGAGGAAGA
ACAGAAAAAGAACGTACATGCATTAAATATTATGCAAGGAGCTTTAAAAAA

Figure 12 (continued)

GCTCATGTAAAGAAGAGTAAAAGAAAAAATAATTTATTTATTAATTTAATAT
TGAGAGTGCCGACACAGTATGCACTAAAAAATATATCTGTGGTGTAGTGAGC
CGATACAAAAGGATAGTCACTCGCATTTTCATAATACATCTTATGTTATGATT
ATGTGTCGGTGGGACTTCACGACGAAAACCCACAATAAAAAAAGAGTTCGGG
GTAGGGTTAAGCATAGTTGAGGCAACTAAACAATCAAGCTAGGATATGCAGT
AGCAGACCGTAAGGTCGTTGTTTAGGTGTGTTGTAATACATACGCTATTAAGA
TGTAAAAATACGGATACCAATGAAGGGAAAGTATAATTTTTGGATGTAGTTT
GTTTGTTCATCTATGGGCAAACTACGTCCAAAGCCGTTTCCAAATCTGCTAAA
AAGTATATCCTTTCTAAAATCAAAGTCAAGTATGAAATCATAAATAAAGTTTA
ATTTTGAAGTTATTATGATATTATGTTTTTCTATTAAAATAAATTAAGTATATA
GAATAGTTTAATAATAGTATATACTTAATGTGATAAGTGTCTGACAGTGTCAC
AGAAAGGATGATTGTTATGGATTATAAGCGGCCGGCCGAAGCAAACTTAAGA
GTGTGTTGATAGTGCAGTATCTTAAAATTTTGTATAATAGGAATTGAAGTTAA
ATTAGATGCTAAAAATTTGTAATTAAGAAGGAGTGATTACATGAACAAAAAT
ATAAAATATTCTCAAAACTTTTTAACGAGTGAAAAAGTACTCAACCAAATAAT
AAAACAATTGAATTTAAAAGAAACCGATACCGTTTACGAAATTGGAACAGGT
AAAGGGCATTTAACGACGAAACTGGCTAAAATAAGTAAACAGGTAACGTCTA
TTGAATTAGACAGTCATCTATTCAACTTATCGTCAGAAAAATTAAAACTGAAT
ACTCGTGTCACTTTAATTCACCAAGATATTCTACAGTTTCAATTCCCTAACAA
ACAGAGGTATAAAATTGTTGGGAGTATTCCTTACCATTTAAGCACACAAATTA
TTAAAAAAGTGGTTTTTGAAAGCCATGCGTCTGACATCTATCTGATTGTTGAA
GAAGGATTCTACAAGCGTACCTTGGATATTCACCGAACACTAGGGTTGCTCTT
GCACACTCAAGTCTCGATTCAGCAATTGCTTAAGCTGCCAGCGGAATGCTTTC
ATCCTAAACCAAAAGTAAACAGTGTCTTAATAAAACTTACCCGCCATACCACA
GATGTTCCAGATAAATATTGGAAGCTATATACGTACTTTGTTTCAAAATGGGT
CAATCGAGAATATCGTCAACTGTTTACTAAAAATCAGTTTCATCAAGCAATGA
AACACGCCAAAGTAAACAATTTAAGTACCGTTACTTATGAGCAAGTATTGTCT
ATTTTTAATAGTTATCTATTATTTAACGGGAGGAAATAATTCTATGAGTCGCTT
TTGTAAATTTGGAAAGTTACACGTTACTAAAGGGAATGTGTTTAAACTCCTTT
TTGATAATCTCATGACCAAAATCCCTTAACGTGAGTTTTCGTTCCACTGAGCG
TCAGACCCCGTAGAAAAGATCAAAGGATCTTCTTGAGATCCTTTTTTTCTGCG
CGTAATCTGCTGCTTGCAAACAAAAAAACCACCGCTACCAGCGGTGGTTTGTT
TGCCGGATCAAGAGCTACCAACTCTTTTTCCGAAGGTAACTGGCTTCAGCAGA
GCGCAGATACCAAATACTGTTCTTCTAGTGTAGCCGTAGTTAGGCCACCACTT

Figure 12 (continued)

CAAGAACTCTGTAGCACCGCCTACATACCTCGCTCTGCTAATCCTGTTACCAG
TGGCTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCACAC
AGCCCAGCTTGGAGCGAACGACCTACACCGAACTGAGATACCTACAGCGTGA
GCTATGAGAAAGCGCCACGCTTCCCGAAGGGAGAAAGGCGGACAGGTATCCG
GTAAGCGGCAGGGTCGGAACAGGAGAGCGCACGAGGGAGCTTCCAGGGGGA
AACGCCTGGTATCTTTATAGTCCTGTCGGGTTTCGCCACCTCTGACTTGAGCGT
CGATTTTTGTGATGCTCGTCAGGGGGCGGAGCCTATGGAAAAACGCCAGCA
ACGCGGCCTTTTTACGGTTCCTGGCCTTTTGCTGGCCTTTTGCTCACATGTTCT
TTCCTGCGTTATCCCCTGATTCTGTGGATAACCGTATTACCGCCTTTGAGTGAG
CTGATACCGCTCGCCGCAGCCGAACGACCGAGCGCAGCGAGTCAGTGAGCGA
GGAAGCGGAAGAGCGCCCAATACGCAGGGCCCCTGCTTCGGGGTCATTATA
GCGATTTTTCGGTATATCCATCCTTTTCGCACGATATACAGGATTTTGCCAA
AGGGTTCGTGTAGACTTTCCTTGGTGTATCCAACGGCGTCAGCCGGGCAGGAT
AGGTGAAGTAGGCCCACCCGCGAGCGGGTGTTCCTTCTTCACTGTCCCTTATT
CGCACCTGGCGGTGCTCAACGGGAATCCTGCTCTGCGAGGCTGGCCGGCTACC
GCCGGCGTAACAGATGAGGGCAAGCGGATGGCTGATGAAACCAAGCCAACCA
GGAAGGGCAGCCCACCTATCAAGGTGTACTGCCTTCCAGACGAACGAAGAGC
GATTGAGGAAAAGGCGGCGGCGGCCGGCATGAGCCTGTCGGCCTACCTGCTG
GCCGTCGGCCAGGGCTACAAAATCACGGGCGTCGTGGACTATGAGCACGTCC
GCGAGCTGGCCCGCATCAATGGCGACCTGGGCCGCCTGGGCGGCCTGCTGAA
ACTCTGGCTCACCGACGACCCGCGCACGGCGCGGTTCGGTGATGCCACGATCC
TCGCCCTGCTGGCGAAGATCGAAGAGAAGCAGGACGAGCTTGGCAAGGTCAT
GATGGGCGTGGTCCGCCCGAGGGCAGAGCCATGACTTTTTTAGCCGCTAAAA
CGGCCGGGGGGTGCGCGTGATTGCCAAGCACGTCCCCATGCGCTCCATCAAG
AAGAGCGACTTCGCGGAGCTGGTGAAGTACATCACCGACGAGCAAGGCAAGA
CCGATCGGGCCC

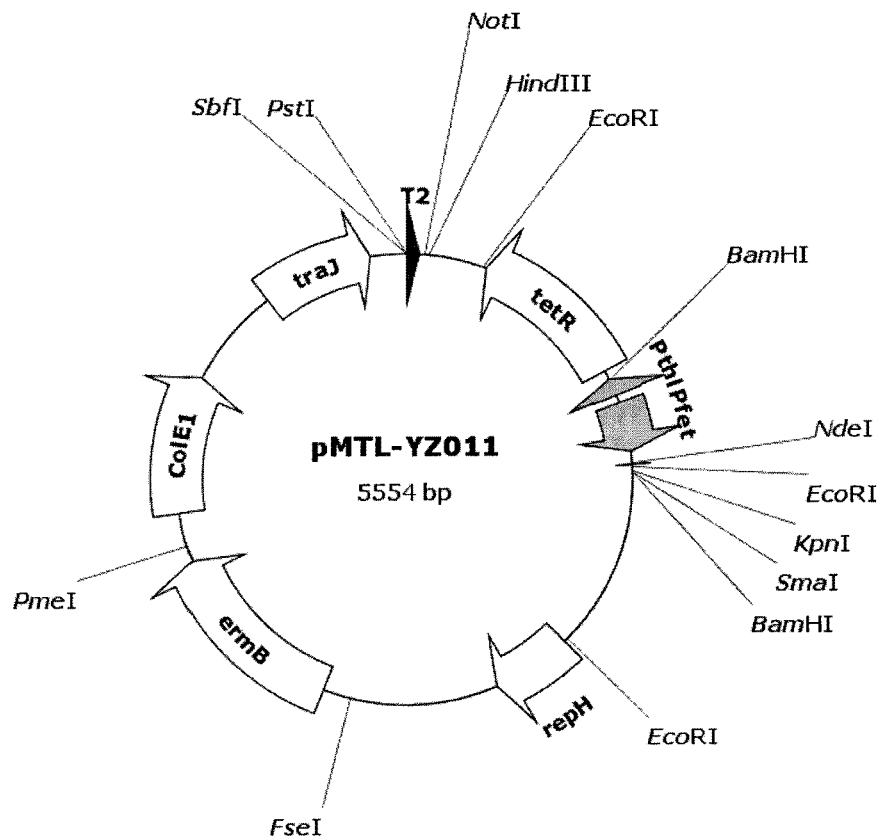

Figure 13.
CCTGCAGGATAAAAAAATTGTAGATAAATTTTATAAAATAGTTTTATCTACAA
TTTTTTTATCAGGAAACAGCTATGACCGCGCCGCGGCGCCAAGCTTAGAAAAA
TATAAATAAGAAGTAGCTTTAAGAGAATTAAATTATTAAGAAAAGCAAAGGT
GTTTAAAAAATAAATTTTTAAACACCTTTGCTTTTCTTAAATTATAAATAAGAT
AAAAAAGAATCCTGAATAAAATAAAAAGGGGTGTCTCAAAATTTTATTTTGA
GACGACCCCTTTTTATTCTATATGTCGATGCTATAGCTGAGATCGTGGAATTCT
TGTTAGCTACCAGATTCACATTTAAGTTGTTTCTCTAAACCACAGATTATCAAT
TCAAGTCCAAAAAGAAATGCTGGTTCTGCGCCTTGATGATCAAATAACTCTAT
TGCTTGTCTTAACAATGGAGGCATTGAATCTGTTGTTGGTGTTTCTCTTTCCTC
TTTTGCAACTTGATGTTCTTGATCCTCCAATACGCAACCTAAAGTAAAATGTC
CTACAGCACTTAGTGCGTATAAGGCATTTTCTAAACTAAAACCCTGTTGACAT

Figure 13 (continued)

AAGAATGCTAATTGATTTTCTAATGTTTCATATTGTTTTTCAGTTGGTCTAGTT
CCTAAATGTACTTTAGCCCCATCTCTATGTGATAATAGAGCACAACGAAAAGA
TTTAGCGTTATTCCTAAGAAAATCTTGCCATGATTCACCTTCTAAAGGACAAA
AGTGAGTGTGATGTCTATCAACATTTCAATAGCTAAGGCGTCAAGTAAAGCT
CTCTTATTCTTCACATGCCAATACAACGTAGGTTGTTCTACTCCAAGTTTCTGA
GCTAACTTTCTTGTAGTTAGTCCTTCTATTCCAACTTCATTTAGTAATTCCAAT
GCACTATTGATAACTTTACTTTTATCAAGTCTAGACATCATTTAATATCCTCCT
CTTCAATATATTTAAGTCGACTGATCGGATCCAATTTATACGTTTTCTCTAACA
ACTTAATTATACCCACTATTATTATTTTTATCAATATAGAGCTCCCATGGCGGC
CGGTCGATATCGATGTGTAGTAGCCTGTGAAATAAGTAAGGAAAAAAAGAA
GTAAGTGTTATATATGATGATTATTTGTAGATGTAGATAGGATAATAGAATC
CATAGAAAATATAGGTTATACAGTTATATAAAAATTACTTTAAAATCTATCAT
TGATAGGGTAAAATATAAATCGTATAAAGTTGTGTAATTTTTAAGGAGGTGTG
TTACAGACGTCCGCGAGAGACCTTAAATATATTGAAGAGGAGGAAATACATA
TGACCATGATTACGAATTCGAGCTCGGTACCCGGGGATCCGCGCCGCCATTAT
TTTTTTGAACAATTGACAATTCATTTCTTATTTTTATTAAGTGATAGTCAAAA
GGCATAACAGTGCTGAATAGAAAGAAATTTACAGAAAAGAAAATTATAGAAT
TTAGTATGATTAATTATACTCATTTATGAATGTTTAATTGAATACAAAAAAAA
ATACTTGTTATGTATTCAATTACGGGTTAAAATATAGACAAGTTGAAAAATTT
AATAAAAAAATAAGTCCTCAGCTCTTATATATTAAGCTACCAACTTAGTATAT
AAGCCAAAACTTAAATGTGCTACCAACACATCAAGCCGTTAGAGAACTCTAT
CTATAGCAATATTTCAAATGTACCGACATACAAGAGAAACATTAACTATATAT
ATTCAATTTATGAGATTATCTTAACAGATATAAATGTAAATTGCAATAAGTAA
GATTTAGAAGTTTATAGCCTTTGTGTATTGGAAGCAGTACGCAAAGGCTTTTT
TATTTGATAAAAATTAGAAGTATATTTATTTTTTCATAATTAATTTATGAAAAT
GAAAGGGGGTGAGCAAAGTGACAGAGGAAAGCAGTATCTTATCAAATAACA
AGGTATTAGCAATATCATTATTGACTTTAGCAGTAAACATTATGACTTTTATA
GTGCTTGTAGCTAAGTAGTACGAAAGGGGGAGCTTTAAAAAGCTCCTTGGAA
TACATAGAATTCATAAATTAATTTATGAAAGAAGGGCGTATATGAAAACTT
GTAAAAATTGCAAAGAGTTTATTAAGATACTGAAATATGCAAATACATTC
GTTGATGATTCATGATAAACAGTAGCAACCTATTGCAGTAAATACAATGAGT
CAAGATGTTTACATAAAGGGAAAGTCCAATGTATTAATTGTTCAAAGATGAA
CCGATATGGATGGTGTGCCATAAAAATGAGATGTTTTACAGAGGAAGAACAG
AAAAAAGAACGTACATGCATTAAATATTATGCAAGGAGCTTTAAAAAAGCTC

Figure 13 (continued)

ATGTAAAGAAGAGTAAAAGAAAAAATAATTTATTTATTAATTTAATATTGA
GAGTGCCGACACAGTATGCACTAAAAAATATATCTGTGGTGTAGTGAGCCGA
TACAAAAGGATAGTCACTCGCATTTTCATAATACATCTTATGTTATGATTATG
TGTCGGTGGGACTTCACGACGAAACCCACAATAAAAAAGAGTTCGGGGTA
GGGTTAAGCATAGTTGAGGCAACTAAACAATCAAGCTAGGATATGCAGTAGC
AGACCGTAAGGTCGTTGTTTAGGTGTGTTGTAATACATACGCTATTAAGATGT
AAAAATACGGATACCAATGAAGGGAAAGTATAATTTTGGATGTAGTTTGTT
TGTTCATCTATGGGCAAACTACGTCCAAAGCCGTTTCCAAATCTGCTAAAAAG
TATATCCTTTCTAAAATCAAAGTCAAGTATGAAATCATAAATAAAGTTTAATT
TTGAAGTTATTATGATATTATGTTTTCTATTAAAATAAATTAAGTATATAGAA
TAGTTTAATAATAGTATATACTTAATGTGATAAGTGTCTGACAGTGTCACAGA
AAGGATGATTGTTATGGATTATAAGCGGCCGGCCGAAGCAAACTTAAGAGTG
TGTTGATAGTGCAGTATCTTAAAATTTTGTATAATAGGAATTGAAGTTAAATT
AGATGCTAAAAATTTGTAATTAAGAAGGAGTGATTACATGAACAAAAATATA
AAATATTCTCAAAACTTTTTAACGAGTGAAAAGTACTCAACCAAATAATAA
AACAATTGAATTTAAAAGAAACCGATACCGTTTACGAATTGGAACAGGTAA
AGGGCATTTAACGACGAAACTGGCTAAAATAAGTAAACAGGTAACGTCTATT
GAATTAGACAGTCATCTATTCAACTTATCGTCAGAAAAATTAAAACTGAATAC
TCGTGTCACTTTAATTCACCAAGATATTCTACAGTTTCAATTCCCTAACAAAC
AGAGGTATAAAATTGTTGGGAGTATTCCTTACCATTTAAGCACACAAATTATT
AAAAAAGTGGTTTTTGAAAGCCATGCGTCTGACATCTATCTGATTGTTGAAGA
AGGATTCTACAAGCGTACCTTGGATATTCACCGAACACTAGGGTTGCTCTTGC
ACACTCAAGTCTCGATTCAGCAATTGCTTAAGCTGCCAGCGGAATGCTTTCAT
CCTAAACCAAAAGTAAACAGTGTCTTAATAAAACTTACCCGCCATACCACAG
ATGTTCCAGATAAATATTGGAAGCTATATACGTACTTTGTTTCAAAATGGGTC
AATCGAGAATATCGTCAACTGTTTACTAAAAATCAGTTTCATCAAGCAATGAA
ACACGCCAAAGTAAACAATTTAAGTACCGTTACTTATGAGCAAGTATTGTCTA
TTTTTAATAGTTATCTATTATTTAACGGGAGGAAATAATTCTATGAGTCGCTTT
TGTAAATTTGGAAAGTTACACGTTACTAAAGGGAATGTGTTTAAACTCCTTTT
TGATAATCTCATGACCAAAATCCCTTAACGTGAGTTTTCGTTCCACTGAGCGT
CAGACCCCGTAGAAAGATCAAAGGATCTTCTTGAGATCCTTTTTTTCTGCGC
GTAATCTGCTGCTTGCAAACAAAAAACCACCGCTACCAGCGGTGGTTTGTTT
GCCGGATCAAGAGCTACCAACTCTTTTTCCGAAGGTAACTGGCTTCAGCAGAG
CGCAGATACCAAATACTGTTCTTCTAGTGTAGCCGTAGTTAGGCCACCACTTC

Figure 13 (continued)

AAGAACTCTGTAGCACCGCCTACATACCTCGCTCTGCTAATCCTGTTACCAGT
GGCTGCTGCCAGTGGCGATAAGTCGTGTCTTACCGGGTTGGACTCAAGACGAT
AGTTACCGGATAAGGCGCAGCGGTCGGGCTGAACGGGGGGTTCGTGCACACA
GCCCAGCTTGGAGCGAACGACCTACACCGAACTGAGATACCTACAGCGTGAG
CTATGAGAAAGCGCCACGCTTCCCGAAGGGAGAAAGGCGGACAGGTATCCGG
TAAGCGGCAGGGTCGGAACAGGAGAGCGCACGAGGGAGCTTCCAGGGGGAA
ACGCCTGGTATCTTTATAGTCCTGTCGGGTTTCGCCACCTCTGACTTGAGCGTC
GATTTTTGTGATGCTCGTCAGGGGGGCGGAGCCTATGGAAAAACGCCAGCAA
CGCGGCCTTTTTACGGTTCCTGGCCTTTTGCTGGCCTTTTGCTCACATGTTCTT
TCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAG
GAAGCGGAAGAGCGCCCAATACGCAGGGCCCCCTGCTTCGGGGTCATTATAG
CGATTTTTTCGGTATATCCATCCTTTTTCGCACGATATACAGGATTTTGCCAAA
GGGTTCGTGTAGACTTTCCTTGGTGTATCCAACGGCGTCAGCCGGGCAGGATA
GGTGAAGTAGGCCCACCCGCGAGCGGGTGTTCCTTCTTCACTGTCCCTTATTC
GCACCTGGCGGTGCTAACGGGAATCCTGCTCTGCGAGGCTGGCCGGCTACC
GCCGGCGTAACAGATGAGGGCAAGCGGATGGCTGATGAAACCAAGCCAACCA
GGAAGGGCAGCCCACCTATCAAGGTGTACTGCCTTCCAGACGAACGAAGAGC
GATTGAGGAAAAGGCGGCGGCGGCCGGCATGAGCCTGTCGGCCTACCTGCTG
GCCGTCGGCCAGGGCTACAAAATCACGGGCGTCGTGGACTATGAGCACGTCC
GCGAGCTGGCCCGCATCAATGGCGACCTGGGCCGCCTGGGCGGCCTGCTGAA
ACTCTGGCTCACCGACGACCCGCGCACGGCGCGGTTCGGTGATGCCACGATCC
TCGCCCTGCTGGCGAAGATCGAAGAGAAGCAGGACGAGCTTGGCAAGGTCAT
GATGGGCGTGGTCCGCCCGAGGGCAGAGCCATGACTTTTTAGCCGCTAAAA
CGGCCGGGGGGTGCGCGTGATTGCCAAGCACGTCCCCATGCGCTCCATCAAG
AAGAGCGACTTCGCGGAGCTGGTGAAGTACATCACCGACGAGCAAGGCAAGA
CCGATCGGGCCC

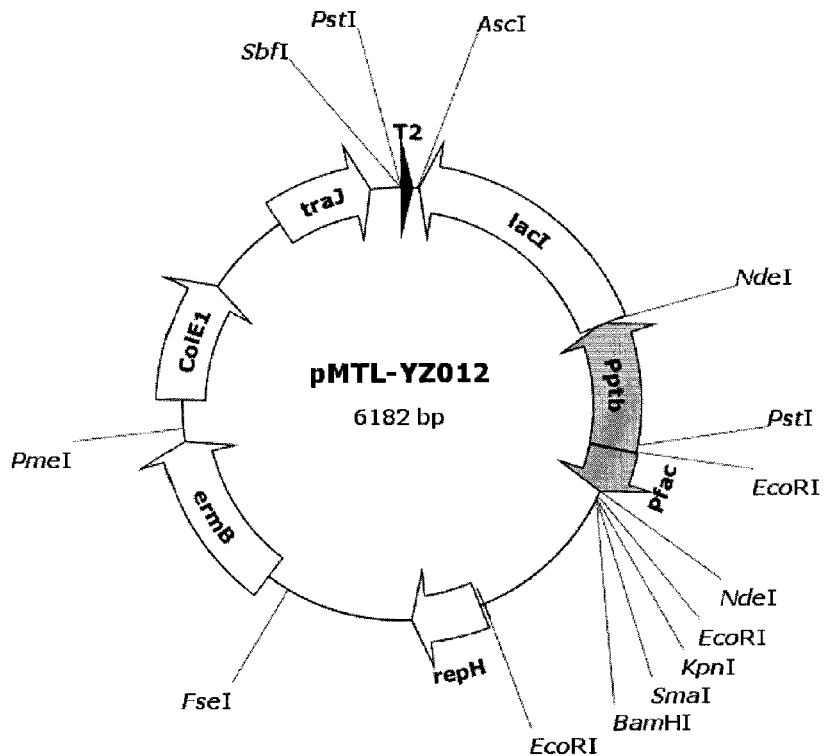

Figure 15.
CCTGCAGGATAAAAAAATTGTAGATAAATTTTATAAAATAGTTTTATCTACAA
TTTTTTTATCAGGAAACAGCTATGACCGGCGCGCCGCTCACTGCCCGCTTTCC
AGTCGGGAAACCTGTCGTGCCAGCTGCATTAATGAATCGGCCAACGCGCGGG
GAGAGGCGGTTTGCGTATTGGGCGCCAGGGTGGTTTTTCTTTTCACCAGTGAG
ACGGGCAACAGCTGATTGCCCTTCACCGCCTGGCCCTGAGAGAGTTGCAGCA
AGCGGTCCACGCTGGTTTGCCCCAGCAGGCGAAAATCCTGTTTGATGGTGGTT
AACGGCGGGATATAACATGAGCTGTCTTCGGTATCGTCGTATCCCACTACCGA
GATATCCGCACCAACGCGCAGCCCGGACTCGGTAATGGCGCGCATTGCGCCC
AGCGCCATCTGATCGTTGGCAACCAGCATCGCAGTGGGAACGATGCCCTCATT
CAGCATTTGCATGGTTTGTTGAAAACCGGACATGGCACTCCAGTCGCCTTCCC
GTTCCGCTATCGGCTGAATTTGATTGCGAGTGAGATATTTATGCCAGCCAGCC
AGACGCAGACGCGCCGAGACAGAACTTAATGGGCCCGCTAACAGCGCGATTT
GCTGGTGACCCAATGCGACCAGATGCTCCACGCCCAGTCGCGTACCGTCTTCA
TGGGAGAAAATAATACTGTTGATGGGTGTCTGGTCAGAGACATCAAGAAATA Figure 15 (continued)

ACGCCGGAACATTAGTGCAGGCAGCTTCCACAGCAATGGCATCCTGGTCATCC
AGCGGATAGTTAATGATCAGCCCACTGACGCGTTGCGCGAGAAGATTGTGCA
CCGCCGYTTTACAGGCTTCGACGCCGCTTCGTTCTACCATCGACACCACCACG
CTGGCACCCAGTTGATCGGCGCGAGATTTAATCGCCGCGACAATTTGCGACGG
CGCGTGCAGGGCCAGACTGGAGGTGGCAACGCCAATCAGCAACGACTGTTTG
CCCGCCAGTTGTTGTGCCACGCGGTTGGGAATGTAATTCAGCTCCGCCATCGC
CGCTTCCACTTTTTCCCGCGTTTTCGCAGAAACGTGGCTGGCCTGGTTCACCAC
GCGGGAAACGGTCTGATAAGAGACACCGGCATACTCTGCGACATCGTATAAC
GTTACTGGTTTCATATGTTGCACCTCTACTTTAATAATTTTAACTTTTATATA
TGATTAATTTAATTGTTTGTTAAATTTATATCAATCAATGCTATGAATATTTCT
TTATACCTTATTGTAACAAAAAAATATTGGAAATGTTGAATTTTCAGAATATT
ATTTTTATTATATTATTAATTTTATATATTCATTTTTATAAGATTTCACAACAC
GAACGTAATATAATATATCTTCCTCATCTTCTGAAAAGATTATACTAATTCTAT
TCATGTTACTTATAATCTTATTTTGGTAAATCGAATTTTTCAATTATATGTTCG
GCAACCTTTATCCCATCAACAGCCGCTGATATTATACCACCTGCAAATCCTGC
CCCTTCTCCAGTTGGATAAAGTCCGCATACATTTATACTTTCAAGTGAAGCAT
TTCTATTCAATCTAACTGGTGCTGATGTTCTTGTCTCAATTCCCGTTAAAATTG
CATCTTCTCTTGCATACCCTTTTATCTTTTATCAAAATTTATAATTCCTTCTTT
AAGAGCCTCTACAACATAATCAGGTAAACATTCTTTTAATTCCCTGAATTATC
TGCAGAGAATTCCCCGGATCGAGATAGTATATGATGCATATTCTTTAAATATA
GATAAAGTTATAGAAGCAATAGAAGATTTAGGATTTACTGTAATATAAATTAC
ACTTTTAAAAAGTTTAAAAACATGATACAATAAGTTATGGTTGGAATTGTTAT
CCGCTCACAATTCCAACTTATGATTAAAATTTTAAGGAGGTGTATTTCATATG
ACCATGATTACGAATTCGAGCTCGGTACCCGGGGATCCGCGCCGCCATTATTT
TTTTGAACAATTGACAATTCATTTCTTATTTTTTATTAAGTGATAGTCAAAAGG
CATAACAGTGCTGAATAGAAAGAAATTTACAGAAAAGAAAATTATAGAATTT
AGTATGATTAATTATACTCATTTATGAATGTTTAATTGAATACAAAAAAAAAT
ACTTGTTATGTATTCAATTACGGGTTAAAATATAGACAAGTTGAAAAATTTAA
TAAAAAAATAAGTCCTCAGCTCTTATATATTAAGCTACCAACTTAGTATATAA
GCCAAAACTTAAATGTGCTACCAACACATCAAGCCGTTAGAGAACTCTATCTA
TAGCAATATTTCAAATGTACCGACATACAAGAGAAACATTAACTATATATATT
CAATTTATGAGATTATCTTAACAGATATAAATGTAAATTGCAATAAGTAAGAT
TTAGAAGTTTATAGCCTTTGTGTATTGGAAGCAGTACGCAAAGGCTTTTTAT
TTGATAAAAATTAGAAGTATATTTATTTTTTCATAATTAATTTATGAAAATGA

Figure 15 (continued)

AAGGGGGTGAGCAAAGTGACAGAGGAAAGCAGTATCTTATCAAATAACAAG
GTATTAGCAATATCATTATTGACTTTAGCAGTAAACATTATGACTTTTATAGT
GCTTGTAGCTAAGTAGTACGAAAGGGGGAGCTTTAAAAAGCTCCTTGGAATA
CATAGAATTCATAAATTAATTTATGAAAAGAAGGGCGTATATGAAAACTTGT
AAAAATTGCAAAGAGTTTATTAAAGATACTGAAATATGCAAAATACATTCGTT
GATGATTCATGATAAACAGTAGCAACCTATTGCAGTAAATACAATGAGTCA
AGATGTTTACATAAAGGGAAAGTCCAATGTATTAATTGTTCAAAGATGAACC
GATATGGATGGTGTGCCATAAAAATGAGATGTTTTACAGAGGAAGAACAGAA
AAAAGAACGTACATGCATTAAATATTATGCAAGGAGCTTTAAAAAAGCTCAT
GTAAAGAAGAGTAAAAAGAAAAAATAATTTATTTATTAATTTAATATTGAGA
GTGCCGACACAGTATGCACTAAAAAATATATCTGTGGTGTAGTGAGCCGATA
CAAAAGGATAGTCACTCGCATTTTCATAATACATCTTATGTTATGATTATGTG
TCGGTGGGACTTCACGACGAAAACCCACAATAAAAAAAGAGTTCGGGGTAGG
GTTAAGCATAGTTGAGGCAACTAAACAATCAAGCTAGGATATGCAGTAGCAG
ACCGTAAGGTCGTTGTTTAGGTGTGTTGTAATACATACGCTATTAAGATGTAA
AAATACGGATACCAATGAAGGGAAAAGTATAATTTTTGGATGTAGTTTGTTTG
TTCATCTATGGGCAAACTACGTCCAAAGCCGTTTCCAAATCTGCTAAAAAGTA
TATCCTTTCTAAAATCAAAGTCAAGTATGAAATCATAAATAAAGTTTAATTTT
GAAGTTATTATGATATTATGTTTTTCTATTAAAATAAATTAAGTATATAGAAT
AGTTTAATAATAGTATATACTTAATGTGATAAGTGTCTGACAGTGTCACAGAA
AGGATGATTGTTATGGATTATAAGCGGCCGGCCGAAGCAAACTTAAGAGTGT
GTTGATAGTGCAGTATCTTAAAATTTTGTATAATAGGAATTGAAGTTAAATTA
GATGCTAAAAATTTGTAATTAAGAAGGAGTGATTACATGAACAAAAATATAA
AATATTCTCAAAACTTTTTAACGAGTGAAAAAGTACTCAACCAAATAATAAA
ACAATTGAATTTAAAAGAAACCGATACCGTTTACGAAATTGGAACAGGTAAA
GGGCATTTAACGACGAAACTGGCTAAAATAAGTAAACAGGTAACGTCTATTG
AATTAGACAGTCATCTATTCAACTTATCGTCAGAAAAATTAAAACTGAATACT
CGTGTCACTTTAATTCACCAAGATATTCTACAGTTTCAATTCCCTAACAAACA
GAGGTATAAAATTGTTGGGAGTATTCCTTACCATTTAAGCACACAAATTATTA
AAAAGTGGTTTTTGAAAGCCATGCGTCTGACATCTATCTGATTGTTGAAGAA
GGATTCTACAAGCGTACCTTGGATATTCACCGAACACTAGGGTTGCTCTTGCA
CACTCAAGTCTCGATTCAGCAATTGCTTAAGCTGCCAGCGGAATGCTTTCATC
CTAAACCAAAAGTAAACAGTGTCTTAATAAAACTTACCCGCCATACCACAGA
TGTTCCAGATAAATATTGGAAGCTATATACGTACTTTGTTTCAAAATGGGTCA

Figure 15 (continued)

ATCGAGAATATCGTCAACTGTTTACTAAAAATCAGTTTCATCAAGCAATGAAA
CACGCCAAAGTAAACAATTTAAGTACCGTTACTTATGAGCAAGTATTGTCTAT
TTTTAATAGTTATCTATTATTTAACGGGAGGAAATAATTCTATGAGTCGCTTTT
GTAAATTTGGAAAGTTACACGTTACTAAAGGGAATGTGTTTAAACTCCTTTTT
GATAATCTCATGACCAAAATCCCTTAACGTGAGTTTTCGTTCCACTGAGCGTC
AGACCCCGTAGAAAGATCAAGGATCTTCTTGAGATCCTTTTTTTCTGCGCG
TAATCTGCTGCTTGCAAACAAAAAACCACCGCTACCAGCGGTGGTTTGTTTG
CCGGATCAAGAGCTACCAACTCTTTTTCCGAAGGTAACTGGCTTCAGCAGAGC
GCAGATACCAAATACTGTTCTTCTAGTGTAGCCGTAGTTAGGCCACCACTTCA
AGAACTCTGTAGCACCGCCTACATACCTCGCTCTGCTAATCCTGTTACCAGTG
GCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAG
CCCAGCTTGGAGCGAACGACCTACACCGAACTGAGATACCTACAGCGTGAGC
TATGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAA
CGCCTGGTATCTTTATAGTCCTGTCGGGTTTCGCCACCTCTGACTTGAGCGTCG
ATTTTTGTGATGCTCGTCAGGGGGGCGGAGCCTATGGAAAAACGCCAGCAAC
GCGGCCTTTTTACGGTTCCTGGCCTTTTGCTGGCCTTTTGCTCACATGTTCTTT
CCTGCGTTATCCCCTGATTCTGTGGATAACCGTATTACCGCCTTTGAGTGAGCT
GATACCGCTCGCCGCAGCCGAACGACCGAGCGCAGCGAGTCAGTGAGCGAGG
AAGCGGAAGAGCGCCCAATACGCAGGGCCCCTGCTTCGGGGTCATTATAGC
GATTTTTCGGTATATCCATCCTTTTCGCACGATATACAGGATTTTGCCAAAG
GGTTCGTGTAGACTTTCCTTGGTGTATCCAACGGCGTCAGCCGGGCAGGATAG
GTGAAGTAGGCCCACCCGCGAGCGGGTGTTCCTTCTTCACTGTCCCTTATTCG
CACCTGGCGGTGCTCAACGGGAATCCTGCTCTGCGAGGCTGGCCGGCTACCGC
CGGCGTAACAGATGAGGGCAAGCGGATGGCTGATGAAACCAAGCCAACCAG
GAAGGGCAGCCCACCTATCAAGGTGTACTGCCTTCCAGACGAACGAAGAGCG
ATTGAGGAAAAGGCGGCGGCGGCCGGCATGAGCCTGTCGGCCTACCTGCTGG
CCGTCGGCCAGGGCTACAAAATCACGGGCGTCGTGGACTATGAGCACGTCCG
CGAGCTGGCCCGCATCAATGGCGACCTGGGCCGCCTGGGCGGCCTGCTGAAA
CTCTGGCTCACCGACGACCCGCGCACGGCGCGGTTCGGTGATGCCACGATCCT
CGCCCTGCTGGCGAAGATCGAAGAGAAGCAGGACGAGCTTGGCAAGGTCATG
ATGGGCGTGGTCCGCCCGAGGGCAGAGCCATGACTTTTTTAGCCGCTAAAAC
GGCCGGGGGTGCGCGTGATTGCCAAGCACGTCCCCATGCGCTCCATCAAGA

Figure 15 (continued)
AGAGCGACTTCGCGGAGCTGGTGAAGTACATCACCGACGAGCAAGGCAAGAC
CGATCGGGCCC

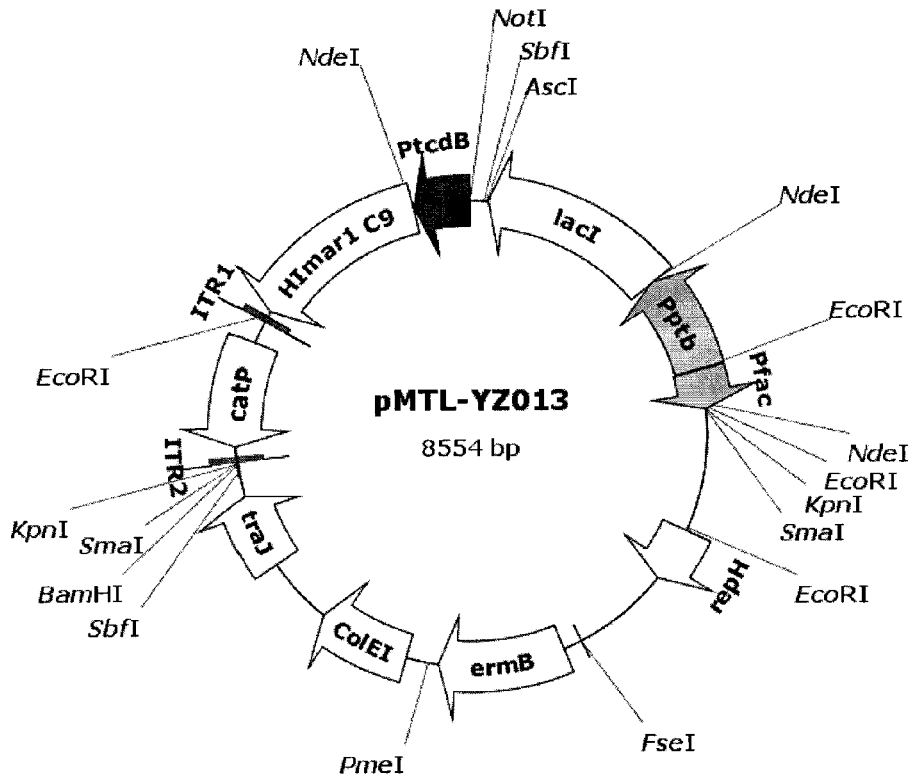

Figure 16.
GCGGTCATAGCTGTTTCCTGATAAAAAAATTGTAGATAAAACTATTTTATAAA
ATTTATCTACAATTTTTTTATCCTGCAGGCAGTCGGCGCGCCGCTCACTGCCCG
CTTTCCAGTCGGGAAACCTGTCGTGCCAGCTGCATTAATGAATCGGCCAACGC
GCGGGGAGAGGCGGTTTGCGTATTGGGCGCCAGGGTGGTTTTTCTTTTCACCA
GTGAGACGGGCAACAGCTGATTGCCCTTCACCGCCTGGCCCTGAGAGAGTTG
CAGCAAGCGGTCCACGCTGGTTTGCCCCAGCAGGCGAAAATCCTGTTTGATGG
TGGTTAACGGCGGGATATAACATGAGCTGTCTTCGGTATCGTCGTATCCCACT
ACCGAGATATCCGCACCAACGCGCAGCCCGGACTCGGTAATGGCGCGCATTG
CGCCCAGCGCCATCTGATCGTTGGCAACCAGCATCGCAGTGGGAACGATGCC
CTCATTCAGCATTTGCATGGTTTGTTGAAAACCGGACATGGCACTCCAGTCGC
CTTCCCGTTCCGCTATCGGCTGAATTTGATTGCGAGTGAGATATTTATGCCAG
CCAGCCAGACGCAGACGCGCCGAGACAGAACTTAATGGGCCCGCTAACAGCG
CGATTTGCTGGTGACCCAATGCGACCAGATGCTCCACGCCCAGTCGCGTACCG

Figure 16 (continued)

TCTTCATGGGAGAAAATAATACTGTTGATGGGTGTCTGGTCAGAGACATCAAG
AAATAACGCCGGAACATTAGTGCAGGCAGCTTCCACAGCAATGGCATCCTGG
TCATCCAGCGGATAGTTAATGATCAGCCCACTGACGCGTTGCGCGAGAAGATT
GTGCACCGCCGYTTTACAGGCTTCGACGCCGCTTCGTTCTACCATCGACACCA
CCACGCTGGCACCCAGTTGATCGGCGCGAGATTTAATCGCCGCGACAATTTGC
GACGGCGCGTGCAGGGCCAGACTGGAGGTGGCAACGCCAATCAGCAACGACT
GTTTGCCCGCCAGTTGTTGTGCCACGCGGTTGGGAATGTAATTCAGCTCCGCC
ATCGCCGCTTCCACTTTTTCCCGCGTTTTCGCAGAAACGTGGCTGGCCTGGTTC
ACCACGCGGGAAACGGTCTGATAAGAGACACCGGCATACTCTGCGACATCGT
ATAACGTTACTGGTTTCATATGTTGCACCTCTACTTTAATAATTTTTAACTTTT
ATATATGATTAATTTAATTGTTTGTTAAATTTATATCAATCAATGCTATGAATA
TTTCTTTATACCTTATTGTAACAAAAAATATTGGAAATGTTGAATTTTCAGA
ATATTATTTTTATTATATTATTAATTTTATATATTCATTTTTATAAGATTTCACA
ACACGAACGTAATATAATATATCTTCCTCATCTTCTGAAAAGATTATACTAAT
TCTATTCATGTTACTTATAATCTTATTTTGGTAAATCGAATTTTTCAATTATAT
GTTCGGCAACCTTTATCCCATCAACAGCCGCTGATATTATACCACCTGCAAAT
CCTGCCCCTTCTCCAGTTGGATAAAGTCCGCATACATTTATACTTTCAAGTGA
AGCATTTCTATTCAATCTAACTGGTGCTGATGTTCTTGTCTCAATTCCCGTTAA
AATTGCATCTTCTCTTGCATACCCTTTTATCTTTTTATCAAAATTTATAATTCCT
TCTTTAAGAGCCTCTACAACATAATCAGGTAAACATTCTTTTAATTCCCTGAA
TTATCTGCAGAGAATTCCCCGGATCGAGATAGTATATGATGCATATTCTTTAA
ATATAGATAAAGTTATAGAAGCAATAGAAGATTTAGGATTTACTGTAATATA
AATTACACTTTTAAAAAGTTTAAAAACATGATACAATAAGTTATGGTTGGAAT
TGTTATCCGCTCACAATTCCAACTTATGATTAAAATTTTAAGGAGGTGTATTTC
ATATGACCATGATTACGAATTCGAGCTCGGTACCCGGGGCGCCGCCATTATTT
TTTTGAACAATTGACAATTCATTTCTTATTTTTTATTAAGTGATAGTCAAAAGG
CATAACAGTGCTGAATAGAAAGAAATTTACAGAAAGAAAATTATAGAATTT
AGTATGATTAATTATACTCATTTATGAATGTTTAATTGAATACAAAAAAAAAT
ACTTGTTATGTATTCAATTACGGGTTAAAATATAGACAAGTTGAAAAATTTAA
TAAAAAATAAGTCCTCAGCTCTTATATATTAAGCTACCAACTTAGTATATAA
GCCAAAACTTAAATGTGCTACCAACACATCAAGCCGTTAGAGAACTCTATCTA
TAGCAATATTTCAAATGTACCGACATACAAGAGAAACATTAACTATATATATT
CAATTTATGAGATTATCTTAACAGATATAAATGTAAATTGCAATAAGTAAGAT
TTAGAAGTTTATAGCCTTTGTGTATTGGAAGCAGTACGCAAAGGCTTTTTTAT

Figure 16 (continued)

TTGATAAAAATTAGAAGTATATTTATTTTTTCATAATTAATTTATGAAAATGA
AAGGGGGTGAGCAAAGTGACAGAGGAAAGCAGTATCTTATCAAATAACAAG
GTATTAGCAATATCATTATTGACTTTAGCAGTAAACATTATGACTTTTATAGT
GCTTGTAGCTAAGTAGTACGAAAGGGGGAGCTTTAAAAAGCTCCTTGGAATA
CATAGAATTCATAAATTAATTTATGAAAGAAGGGCGTATATGAAAACTTGT
AAAAATTGCAAAGAGTTTATTAAAGATACTGAAATATGCAAATACATTCGTT
GATGATTCATGATAAACAGTAGCAACCTATTGCAGTAAATACAATGAGTCA
AGATGTTTACATAAAGGGAAAGTCCAATGTATTAATTGTTCAAAGATGAACC
GATATGGATGGTGTGCCATAAAAATGAGATGTTTTACAGAGGAAGAACAGAA
AAAAGAACGTACATGCATTAAATATTATGCAAGGAGCTTTAAAAAAGCTCAT
GTAAAGAAGAGTAAAAAGAAAAAATAATTTATTTATTAATTTAATATTGAGA
GTGCCGACACAGTATGCACTAAAAAATATATCTGTGGTGTAGTGAGCCGATA
CAAAAGGATAGTCACTCGCATTTTCATAATACATCTTATGTTATGATTATGTG
TCGGTGGGACTTCACGACGAAAACCCACAATAAAAAAAGAGTTCGGGGTAGG
GTTAAGCATAGTTGAGGCAACTAAACAATCAAGCTAGGATATGCAGTAGCAG
ACCGTAAGGTCGTTGTTTAGGTGTGTTGTAATACATACGCTATTAAGATGTAA
AAATACGGATACCAATGAAGGGAAAAGTATAATTTTTGGATGTAGTTTGTTTG
TTCATCTATGGGCAAACTACGTCCAAAGCCGTTTCCAAATCTGCTAAAAAGTA
TATCCTTTCTAAAATCAAAGTCAAGTATGAAATCATAAATAAAGTTTAATTTT
GAAGTTATTATGATATTATGTTTTCTATTAAAATAAATTAAGTATATAGAAT
AGTTTAATAATAGTATATACTTAATGTGATAAGTGTCTGACAGTGTCACAGAA
AGGATGATTGTTATGGATTATAAGCGGCCGGCCGAAGCAAACTTAAGAGTGT
GTTGATAGTGCAGTATCTTAAAATTTTGTATAATAGGAATTGAAGTTAAATTA
GATGCTAAAAATTTGTAATTAAGAAGGAGTGATTACATGAACAAAATATAA
AATATTCTCAAAACTTTTTAACGAGTGAAAAGTACTCAACCAAATAATAAA
ACAATTGAATTTAAAAGAAACCGATACCGTTTACGAAATTGGAACAGGTAAA
GGGCATTTAACGACGAAACTGGCTAAAATAAGTAAACAGGTAACGTCTATTG
AATTAGACAGTCATCTATTCAACTTATCGTCAGAAAAATTAAAACTGAATACT
CGTGTCACTTTAATTCACCAAGATATTCTACAGTTTCAATTCCCTAACAAACA
GAGGTATAAAATTGTTGGGAGTATTCCTTACCATTTAAGCACACAAATTATTA
AAAAGTGGTTTTTGAAAGCCATGCGTCTGACATCTATCTGATTGTTGAAGAA
GGATTCTACAAGCGTACCTTGGATATTCACCGAACACTAGGGTTGCTCTTGCA
CACTCAAGTCTCGATTCAGCAATTGCTTAAGCTGCCAGCGGAATGCTTTCATC

Figure 16 (continued)

CTAAACCAAAAGTAAACAGTGTCTTAATAAAACTTACCCGCCATACCACAGA
TGTTCCAGATAAATATTGGAAGCTATATACGTACTTTGTTTCAAAATGGGTCA
ATCGAGAATATCGTCAACTGTTTACTAAAAATCAGTTTCATCAAGCAATGAAA
CACGCCAAAGTAAACAATTTAAGTACCGTTACTTATGAGCAAGTATTGTCTAT
TTTTAATAGTTATCTATTATTTAACGGGAGGAAATAATTCTATGAGTCGCTTTT
GTAAATTTGGAAAGTTACACGTTACTAAAGGGAATGTGTTTAAACTCCTTTTT
GATAATCTCATGACCAAAATCCCTTAACGTGAGTTTTCGTTCCACTGAGCGTC
AGACCCCGTAGAAAAGATCAAAGGATCTTCTTGAGATCCTTTTTTCTGCGCG
TAATCTGCTGCTTGCAAACAAAAAAACCACCGCTACCAGCGGTGGTTTGTTTG
CCGGATCAAGAGCTACCAACTCTTTTTCCGAAGGTAACTGGCTTCAGCAGAGC
GCAGATACCAAATACTGTCCTTCTAGTGTAGCCGTAGTTAGGCCACCACTTCA
AGAACTCTGTAGCACCGCCTACATACCTCGCTCTGCTAATCCTGTTACCAGTG
GCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAG
CCCAGCTTGGAGCGAACGACCTACACCGAACTGAGATACCTACAGCGTGAGC
ATTGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAA
CGCCTGGTATCTTTATAGTCCTGTCGGGTTTCGCCACCTCTGACTTGAGCGTCG
ATTTTTGTGATGCTCGTCAGGGGGGCGGAGCCTATGGAAAAACGCCAGCAAC
GCGGCCTTTTTACGGTTCCTGGCCTTTTGCTGGCCTTTTGCTCACATGTTCTTT
CCTGCGTTATCCCCTGATTCTGTGGATAACCGTATTACCGCCTTTGAGTGAGCT
GATACCGCTCGCCGCAGCCGAACGACCGAGCGCAGCGAGTCAGTGAGCGAGG
AAGCGGAAGAGCGCCCAATACGCAGGGCCCCCTGCTTCGGGGTCATTATAGC
GATTTTTTCGGTATATCCATCCTTTTCGCACGATATACAGGATTTTGCCAAAG
GGTTCGTGTAGACTTTCCTTGGTGTATCCAACGGCGTCAGCCGGGCAGGATAG
GTGAAGTAGGCCCACCCGCGAGCGGGTGTTCCTTCTTCACTGTCCCTTATTCG
CACCTGGCGGTGCTCAACGGGAATCCTGCTCTGCGAGGCTGGCCGGCTACCGC
CGGCGTAACAGATGAGGGCAAGCGGATGGCTGATGAAACCAAGCCAACCAG
GAAGGGCAGCCCACCTATCAAGGTGTACTGCCTTCCAGACGAACGAAGAGCG
ATTGAGGAAAAGGCGGCGGCGGCCGGCATGAGCCTGTCGGCCTACCTGCTGG
CCGTCGGCCAGGGCTACAAAATCACGGGCGTCGTGGACTATGAGCACGTCCG
CGAGCTGGCCCGCATCAATGGCGACCTGGGCCGCCTGGGCGGCCTGCTGAAA
CTCTGGCTCACCGACGACCCGCGCACGGCGCGGTTCGGTGATGCCACGATCCT
CGCCCTGCTGGCGAAGATCGAAGAGAAGCAGGACGAGCTTGGCAAGGTCATG

Figure 16 (continued)

ATGGGCGTGGTCCGCCCGAGGGCAGAGCCATGACTTTTTTAGCCGCTAAAAC
GGCCGGGGGGTGCGCGTGATTGCCAAGCACGTCCCCATGCGCTCCATCAAGA
AGAGCGACTTCGCGGAGCTGGTGAAGTACATCACCGACGAGCAAGGCAAGAC
CGATCGGGCCCCCTGCAGGCCTCGAGATCTCCATGGACGCGTGACGTCGACTC
TAGAGGATCCCCGGGTACCGAGAAACTAACAGGTTGGCTGATAAGTCCCCGG
TCTAACAAAAATAAGAAGCCTGCATTTGCAGGCTTCTTATTTTAAGCTTAG
ACAAACCTGAAGTTAACTATTTATCAATTCCTGCAATTCGTTTACAAAACGGC
AAATGTGAAATCCGTCACATACTGCGTGATGAACTTGAATTGCCAAAGGAAG
TATAATTTTGTTATCTTCTTTATAATATTTCCCCATAGTAAAAATAGGAATCAA
ATAATCATATCCTTTCTGCAAATTCAGATTAAAGCCATCGAAGGTTGACCACG
GTATCATAGATACATTAAAAATGTTTTCCGGAGCATTTGGCTTTCCTTCCATTC
TATGATTGTTTCCATACCGTTGCGTATCACTTTCATAATCTGCTAAAAATGATT
TAAAGTCAGACTTACACTCAGTCCAAAGGCTGGAAAATGTTTCAGTATCATTG
TGAAATATTGTATAGCTTGGTATCATCTCATCATATATCCCCAATTCACCATCT
TGATTGATTGCCGTCCTAAACTCTGAATGGCGGTTTACAATCATTGCAATATA
ATAAAGCATTGCAGGATATAGTTTCATTCCCTTTTCCTTTATTTGTGTGATATC
CACTTTAACGGTCATGCTGTAGGTACAAGGTACACTTGCAAAGTAGTGGTCAA
AATACTCTTTCTGTTCCAACTATTTTATCAATTTTTCAAATACCATCTAAG
TTCCCTCTCAAATTCAAGTTTATCGCTCTAATGAACAAAGATATTATACCACA
TTTTTGTGAATTTTTCAACTTGCCCACTTCGACTGCACTCCCGACTTAATAACT
TCTTGAACACTTGCCGAAAAACAATTGTGTCAGACCGGGGACTTATCAGCCAA
CCTGTTATACCTCGAATTCGTAATCATGGTCATAATTTATTCAACATAGTTCCC
TTCAAGAGCGATACAACGATTATAACGACCTTCCAATTTTTGATACCATTTT
GGTAGTACTCCTTCGGTTTTGCCTCAAAATAGGCCTCAGTTTCGGCGATCACC
TCTTCATTGCAGCCAAATTTTTTCCCTGCGAGCATCCTTTTGAGGTCTGAGAAC
AAGAAAAAGTCGCTGGGGGCCAGATCTGGAGAATACGGCGGGTGGGGAAGC
AATTCGAAGCCCAATTCATGAATTTTTGCCATCGTTCTCAATGACTTGTGGCA
CGGTGCGTTGTCTTGGTGGAACAACACTTTTTTCTTCTTCATGTGGGGCCGTTT
TGCCGCGATTTCGACCTTCAAACGCTCCAATAACGCCATATAATAGTCACTGT
TGATGGTTTTTCCCTTCTCAAGATAATCGATAAAAATTATTCCATGCGCATCCC
AAAAAACAGAGGCCATTACTTTGCCAGCGGACTTTTGAGTCTTTCCACGCTTC
GGAGACGGTTCACCGGTCGCTGTCCACTCAGCCGACTGTCGATTGGACTCAGG
AGTGTAGTGATGGAGCCATGTTTCATCCATTGTCACATATCGACGGAAAAACT

Figure 16 (continued)

CGGGTGTATTACGAGTTAACAGCTGCAAACACCGCTTAGAATCATCAACACGT
CGTTGTTTTGGTCAAATGTGAGCTCGCGCGGCACCCATTTCGCACAGAGCTT
CCGCATATCCAAATATTGATGAATGATATGACCAACACGTTCCTTTGATATCT
TTAAGGCCTCTGCTATCTCGATCAACTTCATTTTACGGTCATTCAAAATCATTT
TGTGGATTTTTTTGATGTTTTCGTCGGTAACCACCTCTTTCGGGCGTCCACTGC
GTTCACCGTCCTCCGTGCTCATTTCACCACGCTTGAATTTTGCATACCAATCAA
TTATTGTTGATTTCCCTGGGGCAGAGTCCGGAAACTCATTATCAAGCCAAGTT
TTTGCTTCCACTGTATTTTTTCCCTTCAGAAACAGTATTTATCAAAACACGA
AATTCCTTTTTTTCCATCATATGATTTTCTCCTTTACTATAATATTTTATTGAA
TATTTTACATCTAAATGCTAAAACTCTTTTATATATCCTCCTTTCTATTTATA
AAATATACTAATATCTACTTAGGTTTTCATATACATTCACTTCCTAACATTTTA
AATTGAAGACACTCAGTTGATTAATTTGCTCTTCGATTGAATAAAGACGTTGT
CTGAAATAAATATGTAAACTTTGTTCTATATAAAATATAAAAATTAAGATATT
CTTAGATTAAGTTATTGATTTTACAATAAAGTTAATTCTAAAATTTGATTTCTA
TTGTAAATATTTCTTTAAATTCATTAAGCGGCC

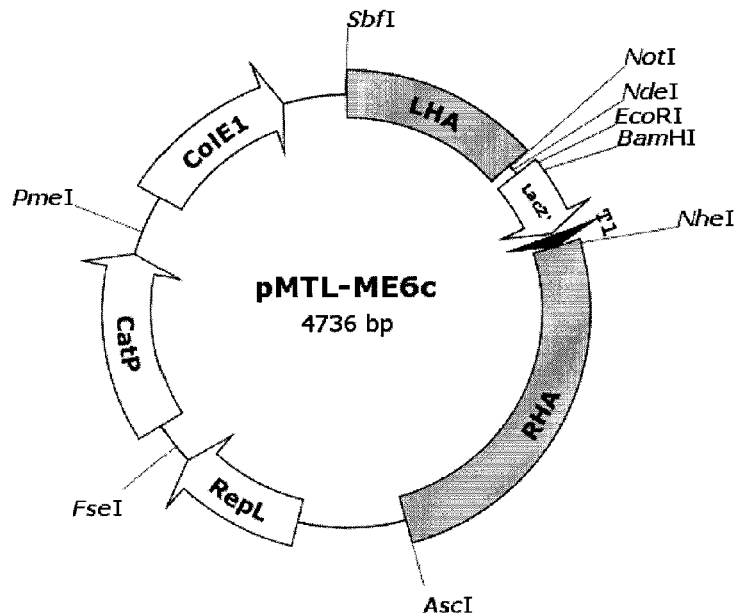

Figure 17.

AGTAATGTACTTACCTTTGGGGATTTCATAACTAAAAGCGGCAGAAGAACAC
CATTTTTTATAAATACAGGTAACTACAAGACAGGTAATCAATTAAATAAGTTG
GCTAAGTTTTATGCTAAAGCAATATATGATAATTTTGGAGATGATTTTGATAT
TTTATTTGGGCCTGCATATAAAGGAATACCTTTAAGTGTTTCAGTAGCTATGG
CACTTGATAATATTTATGGAATTAATGCAGCTTATTGTTCAAATAGAAAAGAA
GTTAAAGATCACGGTGATAAGGGAATACTTCTTGGAGCAAAGCTTGAAGAAG
GAGACAGAGTTATAATTGTAGAAGATGTCACAACAGCTGGTACATCAGTATA
CGAAACAATGCCTATACTTAAATCACAGGCTGAGGTTGATGTAAAGGGAATC
ATAATATCAGTGGATAGAATGGAAAGAGGTAAGGGAGATAAGAGTGCCTTAA
CTGAACTTAAAGAAAGTTTGGATTTAAAACATGTTCTATTGTTACTATGGAA
GAGGTAGTAGAATATTTGTATAAGAAAAATATCAATGGCAAAGTAATCATAG
ATGATAAAATGAAAGATAGAATTAATGAGTACTATAAAGAGTATGGAGTAAA
ATAGTAAGCGGCCGCTGTATCCATATGACCATGATTACGAATTCGAGCTCGGT
ACCCGGGGATCCTCTAGAGTCGACGTCACGCGTCCATGGAGATCTCGAGGCCT
GCAGACATGCAAGCTTGGCACTGGCCGTCGTTTTACAACGTCGTGACTGGGAA

Figure 17 (continued)

AACCCTGGCGTTACCCAACTTAATCGCCTTGCAGCACATCCCCCTTTCGCCAG
CTGGCGTAATAGCGAAGAGGCCCGCACCGATCGCCCTTCCCAACAGTTGCGC
AGCCTGAATGGCGAATGGCGCTAGTATAAAAATAAGAAGCCTGCATTTGCAG
GCTTCTTATTTTATGCTAGCTAAAATAAATGTGCCTCAACTTAGATGTTAAG
GCACATTTATTTTATATATTATTCATGTTTTGAAACATTTTTATCTTTTGTGTAT
TTTACGTGTAGTAATTTGTGAGCAAGTCCTTCACCTGGTTTTCCAAAGTAGCT
ATCATACATTTTAATAATAGCTGGATTATCATGTGACTTTCTCTTTGAAAGAA
CATTTTTATCTTGGTTGTATAATACTGATGCTCTTAGTTTTCTGTAATCAACAT
TTTCTCTATCAAGAGCATTTACGTGAGGTTGACCTCCACCATTTATACATCCAC
CAGGGCAAGCCATTACTTCTATAAAGTGATATTGTTTTCGTTCATTTTCCAG
ATTTCATAAACTCGAAGAAGTTAGAAGCACCATTTATAACAGCAACGTTTAGT
TTATTTCCAGCAATTTCAACTTCCGCTTCTTTTATGCCTTTAAAGCCTCTTACTT
CAGTGTAATCAACATTTTCAAGTTCTTTATTTTCAGCAAAGTCTTTAGCTGATC
TTATTGCAGCTTCCATAACGCCACCGGTTGCACCAAAGATAGCTCCAGCACCA
CTGTAAGTACCCATAGCAGGATCAACTTCACCATCTTCAAGATCTGCAAATTT
AATTTTTGCATCTTTAATCATTTTGCAAGCTCTCTTGTAGTTAAGGATGCATC
AATATCTCTTAAGCTGTTAGTTTCCATGAAAGGAATATCTGCTTCATATTTTT
ATCATTACAAGGCATGATAGTAACTGTATAAACATCTTCTGGAGCTATTCCTG
AAATTGAAGGATAGTAAGTTTTTGATGCAGTACCAAATATTTGTTGTGGTGAT
TTTGCTGATGAAAGATTATCTAATAATTCAGGATGATAATTTTGAGCTAATCT
TACCCATGCAGGACAGCAAGATGTAAACATAGGGAATGGGCCATTATTTTTA
ACTCTGCCTAAAAGTTCAGTAGCTTCTTCCATTATAGTCATATCTGCACCAAA
GTTTATATCAAATACTTTATCAAAGCCTAACATTCTAAGTGCAGTATATAGTT
TTCCTGTTACATCTTTTCCATATCCCATTTTGAATAATTCGCCCATAGCAGTTC
TTACTGATGGAGCCATTGCAACAATGACATGTTTTTAGGGTCATTAAGAGCT
TCTTGAACTTTTTCTATATGGGATTTTTCTTTTAAAGCAGCAACAGGCGCGCCG
CATTCACTTCTTTTCTATATAAATATGAGCGAAGCGAATAAGCGTCGGAAAAG
CAGCAAAAAGTTTCCTTTTTGCTGTTGGAGCATGGGGGTTCAGGGGGTGCAGT
ATCTGACGTCAATGCCGAGCGAAAGCGAGCCGAAGGGTAGCATTTACGTTAG
ATAACCCCCTGATATGCTCCGACGCTTTATATAGAAAGAAGATTCAACTAGG
TAAAATCTTAATATAGGTTGAGATGATAAGGTTTATAAGGAATTTGTTTGTTC
TAATTTTTCACTCATTTGTTCTAATTTCTTTTAACAAATGTTCTTTTTTTTTA
GAACAGTTATGATATAGTTAGAATAGTTTAAAATAAGGAGTGAGAAAAAGAT
GAAAGAAAGATATGGAACAGTCTATAAAGGCTCTCAGAGGCTCATAGACGAA

Figure 17 (continued)

GAAAGTGGAGAAGTCATAGAGGTAGACAAGTTATACCGTAAACAAACGTCTG
GTAACTTCGTAAAGGCATATATAGTGCAATTAATAAGTATGTTAGATATGATT
GGCGGAAAAAACTTAAAATCGTTAACTATATCCTAGATAATGTCCACTTAAG
TAACAATACAATGATAGCTACAACAAGAGAAATAGCAAAAGCTACAGGAACA
AGTCTACAAACAGTAATAACAACACTTAAAATCTTAGAAGAAGGAAATATTA
TAAAAAGAAAAACTGGAGTATTAATGTTAAACCCTGAACTACTAATGAGAGG
CGACGACCAAAAACAAAATACCTCTTACTCGAATTTGGGAACTTTGAGCAA
GAGGCAAATGAAATAGATTGACCTCCCAATAACACCACGTAGTTATTGGGAG
GTCAATCTATGAAATGCGATTAAGGGCCGGCCAAGTGGGCAAGTTGAAAAAT
TCACAAAAATGTGGTATAATATCTTTGTTCATTAGAGCGATAAACTTGAATTT
GAGAGGGAACTTAGATGGTATTTGAAAAAATTGATAAAAATAGTTGGAACAG
AAAAGAGTATTTTGACCACTACTTTGCAAGTGTACCTTGTACCTACAGCATGA
CCGTTAAAGTGGATATCACACAAATAAAGGAAAAGGGAATGAAACTATATCC
TGCAATGCTTTATTATATTGCAATGATTGTAAACCGCCATTCAGAGTTTAGGA
CGGCAATCAATCAAGATGGTGAATTGGGGATATATGATGAGATGATACCAAG
CTATACAATATTTCACAATGATACTGAAACATTTTCCAGCCTTTGGACTGAGT
GTAAGTCTGACTTTAAATCATTTTTAGCAGATTATGAAAGTGATACGCAACGG
TATGGAAACAATCATAGAATGGAAGGAAAGCCAAATGCTCCGGAAAACATTT
TTAATGTATCTATGATACCGTGGTCAACCTTCGATGGCTTTAATCTGAATTTGC
AGAAAGGATATGATTATTTGATTCCTATTTTTACTATGGGGAAATATTATAAA
GAAGATAACAAAATTATACTTCCTTTGGCAATTCAAGTTCATCACGCAGTATG
TGACGGATTTCACATTTGCCGTTTTGTAAACGAATTGCAGGAATTGATAAATA
GTTAACTTCAGGTTTGTCTGTAACTAAAAACAAGTATTTAAGCAAAAACATCG
TAGAAATACGGTGTTTTTGTTACCCTAAGTTTAAACTCCTTTTTGATAATCTC
ATGACCAAAATCCCTTAACGTGAGTTTTCGTTCCACTGAGCGTCAGACCCCGT
AGAAAAGATCAAAGGATCTTCTTGAGATCCTTTTTTTCTGCGCGTAATCTGCT
GCTTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGATAC
CAAATACTGTCCTTCTAGTGTAGCCGTAGTTAGGCCACCACTTCAAGAACTCT
GTAGCACCGCCTACATACCTCGCTCTGCTAATCCTGTTACCAGTGGCTGCTGC
CAGTGGCGATAAGTCGTGTCTTACCGGGTTGGACTCAAGACGATAGTTACCGG
ATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAA
AGCGCCACGCTTCCCGAAGGGAGAAAGGCGGACAGGTATCCGGTAAGCGGCA

Figure 17 (continued)

GGGTCGGAACAGGAGAGCGCACGAGGGAGCTTCCAGGGGGAAACGCCTGGT
ATCTTTATAGTCCTGTCGGGTTTCGCCACCTCTGACTTGAGCGTCGATTTTTGT
GATGCTCGTCAGGGGGGCGGAGCCTATGGAAAAACGCCAGCAACGCGGCCTT
TTTACGGTTCCTGGCCTTTTGCTGGCCTTTTGCTCACATGTTCTTTCCTGCGTTA
TCCCCTGATTCTGTGGATAACCGTATTACCGCCTTTGAGTGAGCTGATACCGC
TCGCCGCAGCCGAACGACCGAGCGCAGCGAGTCAGTGAGCGAGGAAGCGGA
AGAGCGCCCAATACGCAGGGCCCCCTGCAGGAG

SEQUENCE LISTING

<160> NUMBER OF SEQ ID NOS: 34

<210> SEQ ID NO 1
<211> LENGTH: 21
<212> TYPE: DNA
<213> ORGANISM: Artificial Sequence
<220> FEATURE:
<223> OTHER INFORMATION: Promoter of the Clostridium pasteuranium
      ferredoxin with lac operator

<400> SEQUENCE: 1
aattgttatc cgctcacaat t                                          21

<210> SEQ ID NO 2
<211> LENGTH: 72
<212> TYPE: DNA
<213> ORGANISM: Artificial Sequence
<220> FEATURE:
<223> OTHER INFORMATION: Pfac

<400> SEQUENCE: 2
acacttttaa aaagtttaaa aacatgatac aataagttat ggttggaatt gttatccgct   60
cacaattcca ac                                                      72

<210> SEQ ID NO 3
<211> LENGTH: 15
<212> TYPE: DNA
<213> ORGANISM: Artificial Sequence
<220> FEATURE:
<223> OTHER INFORMATION: Clostridium sporogenes ferredoxin gene with Tet
      operator

<400> SEQUENCE: 3
tctatcattg atagg                                                   15

```
<210> SEQ ID NO 4
<211> LENGTH: 55
<212> TYPE: DNA
<213> ORGANISM: Artificial Sequence
<220> FEATURE:
<223> OTHER INFORMATION: Pfet

<400> SEQUENCE: 4
aaattacttt aaaatctatc attgataggg taaaatataa atcgtataaa gttgt      55

<210> SEQ ID NO 5
<211> LENGTH: 29
<212> TYPE: DNA
<213> ORGANISM: Artificial Sequence
<220> FEATURE:
<223> OTHER INFORMATION: PxylA

<400> SEQUENCE: 5
tttacaaaaa atgaacaatg tgctatatt                                   29

<210> SEQ ID NO 6
<211> LENGTH: 60
<212> TYPE: DNA
<213> ORGANISM: Artificial Sequence
<220> FEATURE:
<223> OTHER INFORMATION: Pth1

<400> SEQUENCE: 6
tatattgata aaaataataa tagtgggtat aattaagttg ttagagaaaa cgtataaatt  60

<210> SEQ ID NO 7
<211> LENGTH: 1613
<212> TYPE: DNA
<213> ORGANISM: Artificial Sequence
<220> FEATURE:
<223> OTHER INFORMATION: pCB102

<400> SEQUENCE: 7
gccattattt ttttgaacaa ttgacaattc atttcttatt ttttattaag tgatagtcaa   60
aaggcataac agtgctgaat agaaagaaat ttacagaaaa gaaaattata gaatttagta  120
tgattaatta tactcattta tgaatgttta attgaataca aaaaaaaata cttgttatgt  180
attcaattac gggttaaaat atagacaagt tgaaaaattt aataaaaaaa taagtcctca  240
gctcttatat attaagctac caacttagta tataagccaa aacttaaatg tgctaccaac  300
acatcaagcc gttagagaac tctatctata gcaatatttc aaatgtaccg acatacaaga  360
gaaacattaa ctatatatat tcaatttatg agattatctt aacagatata aatgtaaatt  420
gcaataagta agatttagaa gtttatagcc tttgtgtatt ggaagcagta cgcaaaggct  480 ttttttatttg ataaaaatta gaagtatatt tatttttttca taattaattt atgaaaatga  540 aaggggggtga gcaaagtgac agaggaaagc agtatcttat caaataacaa ggtattagca  600
atatcattat tgactttagc agtaaacatt atgacttttta tagtgcttgt agctaagtag  660
tacgaaaggg ggagctttaa aaagctccctt ggaatacata gaattcataa attaatttat  720
gaaaagaagg gcgtatatga aaacttgtaa aaattgcaaa gagtttatta agatactga  780 aatatgcaaa atacattcgt tgatgattca tgataaaaca gtagcaacct attgcagtaa  840
atacaatgag tcaagatgtt tacataaagg gaaagtccaa tgtattaatt gttcaaagat  900
gaaccgatat ggatggtgtg ccataaaaat gagatgtttt acagaggaag aacagaaaaa  960
agaacgtaca tgcattaaat attatgcaag gagctttaaa aaagctcatg taaagaagag 1020
```

```
taaaaagaaa aaataattta tttattaatt taatattgag agtgccgaca cagtatgcac   1080
taaaaaatat atctgtggtg tagtgagccg atacaaaagg atagtcactc gcattttcat   1140
aatacatctt atgttatgat tatgtgtcgg tgggacttca cgacgaaaac ccacaataaa   1200
aaaagagttc ggggtagggt taagcatagt tgaggcaact aaacaatcaa gctaggatat   1260
gcagtagcag accgtaaggt cgttgtttag gtgtgttgta atacatacgc tattaagatg   1320
taaaaatacg gataccaatg aagggaaaag tataattttt ggatgtagtt tgtttgttca   1380
tctatgggca aactacgtcc aaagccgttt ccaaatctgc taaaaagtat atcctttcta   1440
aaatcaaagt caagtatgaa atcataaata aagtttaatt ttgaagttat tatgatatta   1500
tgtttttcta ttaaaataaa ttaagtatat agaatagttt aataatagta tatacttaat   1560
gtgataagtg tctgacagtg tcacagaaag gatgattgtt atggattata agc          1613

<210> SEQ ID NO 8
<211> LENGTH: 105
<212> TYPE: PRT
<213> ORGANISM: Artificial Sequence
<220> FEATURE:
<223> OTHER INFORMATION: RepH protein

<400> SEQUENCE: 8

Met Lys Arg Arg Ala Tyr Met Lys Thr Cys Lys Asn Cys Lys Glu Phe
1               5                   10                  15

Ile Lys Asp Thr Glu Ile Cys Lys Ile His Ser Leu Met Ile His Asp
            20                  25                  30

Lys Thr Val Ala Thr Tyr Cys Ser Lys Tyr Asn Glu Ser Arg Cys Leu
        35                  40                  45

His Lys Gly Lys Val Gln Cys Ile Asn Cys Ser Lys Met Asn Arg Tyr
    50                  55                  60

Gly Trp Cys Ala Ile Lys Met Arg Cys Phe Thr Glu Glu Glu Gln Lys
65                  70                  75                  80

Lys Glu Arg Thr Cys Ile Lys Tyr Tyr Ala Arg Ser Phe Lys Lys Ala
                85                  90                  95

His Val Lys Lys Ser Lys Lys Lys Lys
            100                 105

<210> SEQ ID NO 9
<211> LENGTH: 184
<212> TYPE: PRT
<213> ORGANISM: Clostridium difficile

<400> SEQUENCE: 9

Met Gln Lys Ser Phe Tyr Glu Leu Ile Val Leu Ala Arg Asn Asn Ser
1               5                   10                  15

Val Asp Asp Leu Gln Glu Ile Leu Phe Met Phe Lys Pro Leu Val Lys
            20                  25                  30

Lys Leu Ser Arg Val Leu His Tyr Glu Glu Gly Glu Thr Asp Leu Ile
        35                  40                  45

Ile Phe Phe Ile Glu Leu Ile Lys Asn Ile Lys Leu Ser Ser Phe Ser
    50                  55                  60

Glu Lys Ser Asp Ala Ile Ile Val Lys Tyr Ile His Lys Ser Leu Leu
65                  70                  75                  80

Asn Lys Thr Phe Glu Leu Ser Arg Arg Tyr Ser Lys Met Lys Phe Asn
                85                  90                  95

Phe Val Glu Phe Asp Glu Asn Ile Leu Asn Met Lys Asn Asn Tyr Gln
```

```
                    100                 105                 110
Ser Lys Ser Val Phe Glu Glu Asp Ile Cys Phe Phe Glu Tyr Ile Leu
        115                 120                 125

Lys Glu Leu Ser Gly Ile Gln Arg Lys Val Ile Phe Tyr Lys Tyr Leu
    130                 135                 140

Lys Gly Tyr Ser Asp Arg Glu Ile Ser Val Lys Leu Lys Ile Ser Arg
145                 150                 155                 160

Gln Ala Val Asn Lys Ala Lys Asn Arg Ala Phe Lys Lys Ile Lys Lys
                165                 170                 175

Asp Tyr Glu Asn Tyr Phe Asn Leu
            180

<210> SEQ ID NO 10
<211> LENGTH: 67
<212> TYPE: DNA
<213> ORGANISM: Clostridium difficile

<400> SEQUENCE: 10
tataagatat gtttacaaat tactatcaga caatctcctt atctaataga agagtcaatt      60
aactaat                                                               67

<210> SEQ ID NO 11
<211> LENGTH: 84
<212> TYPE: DNA
<213> ORGANISM: Clostridium difficile

<400> SEQUENCE: 11
atctaagaat atcttaattt ttatattta tatagaacaa agtttacata tttatttcag       60
acaacgtctt tattcaatcg aaga                                            84

<210> SEQ ID NO 12
<211> LENGTH: 50
<212> TYPE: DNA
<213> ORGANISM: Clostridium difficile

<400> SEQUENCE: 12
gaacaaagtt tacatattta tttcagacaa cgtctttatt caatcgaaga                50

<210> SEQ ID NO 13
<211> LENGTH: 50
<212> TYPE: DNA
<213> ORGANISM: Clostridium difficile

<400> SEQUENCE: 13
atctaagaat atcttaattt ttatattta tatagaacaa agtttacata                50

<210> SEQ ID NO 14
<211> LENGTH: 35
<212> TYPE: DNA
<213> ORGANISM: Artificial Sequence
<220> FEATURE:
<223> OTHER INFORMATION: primer del sense

<400> SEQUENCE: 14
ctcgatccgg ggaattctct gcagataatt caggg                                35

<210> SEQ ID NO 15
<211> LENGTH: 35
<212> TYPE: DNA
<213> ORGANISM: Artificial Sequence
<220> FEATURE:
```

<223> OTHER INFORMATION: Primer del antisense

<400> SEQUENCE: 15

| cccctgaatta tctgcagaga attccccgga tcgag | 35 |
|---|---|

<210> SEQ ID NO 16
<211> LENGTH: 7763
<212> TYPE: DNA
<213> ORGANISM: Artificial Sequence
<220> FEATURE:
<223> OTHER INFORMATION: pMTL-YZ006

<400> SEQUENCE: 16

| actgccgggc ctcttgcggg atcaaaagaa aaacgaaatg atacaccaat cagtgcaaaa | 60 |
|---|---|
| aaagatataa tgggagataa gacggttcgt gttcgtgctg acttgcacca tatcataaaa | 120 |
| atcgaaacag caaagaatgg cggaaacgta aagaagtta tggaaataag acttagaagc | 180 |
| aaacttaaga gtgtgttgat agtgcagtat cttaaaattt tgtataatag gaattgaagt | 240 |
| taaattagat gctaaaaatt tgtaattaag aaggagtgat tacatgaaca aaaatataaa | 300 |
| atattctcaa aacttttttaa cgagtgaaaa agtactcaac caaataataa acaattgaa | 360 |
| tttaaaagaa accgataccg tttacgaaat tggaacaggt aaagggcatt taacgacgaa | 420 |
| actggctaaa ataagtaaac aggtaacgtc tattgaatta gacagtcatc tattcaactt | 480 |
| atcgtcagaa aaattaaaac tgaatactcg tgtcactta attccaccaag atattctaca | 540 |
| gtttcaattc cctaacaaac agaggtataa aattgttggg agtattcctt accatttaag | 600 |
| cacacaaatt attaaaaaag tggttttttga agccatgcg tctgacatct atctgattgt | 660 |
| tgaagaagga ttctacaagc gtaccttgga tattcaccga acactagggt tgctcttgca | 720 |
| cactcaagtc tcgattcagc aattgcttaa gctgccagcg gaatgctttc atcctaaacc | 780 |
| aaaagtaaac agtgtcttaa taaaacttac ccgccatacc acagatgttc cagataaata | 840 |
| ttggaagcta tatcgtact tgtttcaaa atgggtcaat cgagaatatc gtcaactgtt | 900 |
| tactaaaaat cagtttcatc aagcaatgaa acacgccaaa gtaaacaatt aagtaccgt | 960 |
| tacttatgag caagtattgt ctatttttaa tagttatcta ttatttaacg ggaggaaata | 1020 |
| attctatgag tcgcttttgt aaatttggaa agttacacgt tactaaaggg aatgtagata | 1080 |
| aattattagg tatactactg acagcttcca aggagctaaa gaggtcccta gcgcctacgg | 1140 |
| ggaatttgat cgtccattcc gacagcatcg ccagtcacta tggcgtgctg ctagagctta | 1200 |
| taatccataa caatcatcct ttctgtgaca ctgtcagaca cttatacat taagtatata | 1260 |
| ctattattaa actattctat atacttaatt tattttaata gaaaaacata atatcataat | 1320 |
| aacttcaaaa ttaaacttta tttatgattt catacttgac tttgattta gaaaggatat | 1380 |
| acttttttagc agatttggaa acggctttgg acgtagtttg cccatagatg aacaaacaaa | 1440 |
| ctacatccaa aaattatact tttcccttca ttggtatccg tatttttaca tcttaatagc | 1500 |
| gtatgtatta caacacacct aaacaacgac cttacggtct gctactgcat atcctagctt | 1560 |
| gattgtttag ttgcctcaac tatgcttaac cctaccccga actctttttt tattgtgggt | 1620 |
| tttcgtcgtg aagtcccacc gacacataat cataacataa gatgtattat gaaaatgcga | 1680 |
| gtgactatcc tttttgtatcg gctcactaca ccacagatat atttttagt gcatactgtg | 1740 |
| tcggcactct caatattaaa ttaataaata aattatttttt tcttttttact cttctttaca | 1800 |
| tgagcttttt taaagctcct tgcataatat ttaatgcatg tacgttcttt tttctgttct | 1860 |
| tcctctgtaa aacatctcat ttttatggca caccatccat atcggttcat ctttgaacaa | 1920 |

```
ttaatacatt ggactttccc tttatgtaaa catcttgact cattgtatt  actgcaatag    1980 gttgctactg ttttatcatg aatcatcaac gaatgtattt tgcatatttc agtatcttta    2040
ataaactctt tgcaattttt acaagttttc atatacgccc ttcttttcat aaattaattt    2100
atgaattcta tgtattccaa ggagcttttt aaagctcccc ctttcgtact acttagctac    2160
aagcactata aaagtcataa tgtttactgc taaagtcaat aatgatattg ctaatacctt    2220
gttatttgat aagatactgc tttcctctgt cactttgctc accccctttc attttcataa    2280
attaattatg aaaaaataaa tatacttcta attttttatca aataaaaaag cctttgcgta    2340
ctgcttccaa tacacaaagg ctataaactt ctaaatctta cttattgcaa tttacattta    2400
tatctgttaa gataatctca taaattgaat atatatagtt aatgtttctc ttgtatgtcg    2460
gtacatttga aatattgcta tagatagagt tctctaacgg cttgatgtgt tggtagcaca    2520
tttaagtttt ggcttatata ctaagttggt agcttaatat ataagagctg aggacttatt    2580 ttttttattaa attttttcaac ttgtctatat tttaacccgt aattgaatac ataacaagta    2640 ttttttttttg tattcaatta acattcata aatgagtata attaatcata ctaaattcta    2700
taattttctt ttctgtaaat ttcttttctat tcagcactgt tatgccttt  gactatcact    2760 taataaaaaa taagaaatga attgtcaatt gttcaaaaaa aatatggctg ctgcatctct    2820
tcgctagcgc cattcgccat tcaggctgcg caactgttgg gaagggcgat cggtgcgggc    2880
ctcttcgcta ttacgccagc tggcgaaagg gggatgtgct gcaaggcgat taagttgggt    2940
aacgccaggg ttttcccagt cacgacgttg taaaacgacg ccagtgcca  agcttgcatg    3000 ccatggtacc catcggcgag gctagttacc cttaagttat tggtatgact ggttttaagc    3060
gcaaaaaaag ttgctttttc gtacctatta agttatcgtt agaaaaccga ctgtaaaaag    3120
tacagtcggc attatctcat attataaaag ccagtcatta ggcctatctg acaattcctg    3180
aatagagttc ataaacaatc ctgcatgata accatcacaa acagaatgat gtacctgtaa    3240
agatagcggt aaatatattg aattacccttt attaatgaat tttcctgctg taataatggg    3300
tagaaggtaa ttactattat tattgatatt taagttaaac ccagtaaatg aagtccatgg    3360
aataatagaa agagaaaaag cattttcagg tataggtgtt ttgggaaaca atttccccga    3420
accattatat ttctctacat cagaaaggta taaatcataa aactctttga agtcattctt    3480
tacaggagtc caaataccag agaatgtttt agatacacca tcaaaaattg tataaagtgg    3540
ctctaactta tcccaataac ctaactctcc gtcgctattg taaccagttc taaaagctgt    3600
atttgagttt atcacccttg tcactaagaa aataaatgca gggtaaaatt tatatccttc    3660
ttgttttatg tttcggtata aaacactaat atcaatttct gtggttatac taaaagtcgt    3720
ttgttggttc aaataatgat taaatatctc ttttctcttc caattgtcta aatcaatttt    3780
attaaagttc atttgatatg cctcctaaat ggggatcccc gggtaccgag ctcgaattcg    3840
taatcatggt catatgaaat acacctcctt aaaattttaa tcataagttg gaattgtgag    3900
cggataacaa ttccaaccat aacttattgt atcatgtttt taaactttt  aaaagtgtaa    3960 tttatattac agtaaatcct aaatcttcta ttgcttctat aactttatct atatttaaag    4020
aatatgcatc atatactatc tcgatccggg gaattctctg cagataattc agggaattaa    4080
aagaatgttt acctgattat gttgtagagg ctcttaaaga aggaattata aattttgata    4140
aaaagataaa agggtatgca agagaagatg caatttaac  gggaattgag acaagaacat    4200
cagcaccagt tagattgaat agaaatgctt cacttgaaag tataaatgta tgcggacttt    4260
```

```
atccaactgg agaaggggca ggatttgcag gtggtataat atcagcggct gttgatggga    4320
taaaggttgc cgaacatata attgaaaaat tcgatttacc aaaataagat tataagtaac    4380
atgaatagaa ttagtataat cttttcagaa gatgaggaag atatattata ttacgttcgt    4440
gttgtgaaat cttataaaaa tgaatatata aaattaataa tataataaaa ataatattct    4500
gaaaattcaa catttccaat attttttttgt tacaataagg tataaagaaa tattcatagc    4560
attgattgat ataaatttaa caaacaatta aattaatcat atataaaagt taaaaattat    4620
taaagtagag gtgcaacata tgaaaccagt aacgttatac gatgtcgcag agtatgccgg    4680
tgtctcttat cagaccgttt cccgcgtggt gaaccaggcc agccacgttt ctgcgaaaac    4740
gcgggaaaaa gtggaagcgg cgatggcgga gctgaattac attcccaacc gcgtggcaca    4800
acaactggcg ggcaaacagt cgttgctgat tggcgttgcc acctccagtc tggccctgca    4860
cgcgccgtcg caaattgtcg cggcgattaa atctcgcgcc gatcaactgg gtgccagcgt    4920
ggtggtgtcg atggtagaac gaagcggcgt cgaagcctgt aaagcggcgg tgcacaatct    4980
tctcgcgcaa cgcgtcagtg ggctgatcat taactatccg ctggatgacc aggatgccat    5040
tgctgtggaa gctgcctgca ctaatgttcc ggcgttattt cttgatgtct ctgaccagac    5100
acccatcaac agtattattt tctcccatga agacggtacg cgactgggcg tggagcatct    5160
ggtcgcattg ggtcaccagc aaatcgcgct gttagcgggc ccattaagtt ctgtctcggc    5220
gcgtctgcgt ctggctggct ggcataaata tctcactcgc aatcaaattc agccgatagc    5280
ggaacgggaa ggcgactgga gtgccatgtc cggttttcaa caaaccatgc aaatgctgaa    5340
tgagggcatc gttcccactg cgatgctggt tgccaacgat cagatggcgc tgggcgcaat    5400
gcgcgccatt accgagtccg ggctgcgcgt tggtgcggat atctcggtag tgggatacga    5460
cgataccgaa gacagctcat gttatatccc gccgtcaacc accatcaaac aggattttcg    5520
cctgctgggg caaaccagcg tggaccgctt gctgcaactc tctcagggcc aggcggtgaa    5580
gggcaatcag ctgttgcccg tctcactggt gaaaagaaaa accaccctgg cgcccaatac    5640
gcaaaccgcc tctccccgcg cgttggccga ttcattaatg cagctggcac gacaggtttc    5700
ccgactggaa agcgggcagt gagcgcaacg caattaatgt gagttaggaa ttatcccgtg    5760
acaggtcatt cagactggct aatgcaccca gtaaggcagc ggtatcatca acaggcttac    5820
ccgtcttact gcttccgctt cctcgctcac tgactcgctg cgctcggtcg ttcggctgcg    5880
gcgagcggta tcagctcact caaaggcggt aatacggtta tccacagaat cagggggataa    5940
cgcaggaaag aacatgtgag caaaaggcca gcaaaaggcc aggaaccgta aaaaggccgc    6000
gttgctggcg ttttttccata ggctccgccc ccctgacgag catcacaaaa atcgacgctc    6060
aagtcagagg tggcgaaacc cgacaggact ataaagatac caggcgtttc ccctggaag    6120
ctccctcgtg cgctctcctg ttccgaccct gccgcttacc ggatacctgt ccgcctttct    6180
cccttcggga agcgtggcgc tttctcaatg ctcacgctgt aggtatctca gttcggtgta    6240
ggtcgttcgc tccaagctgg gctgtgtgca cgaaccccc gttcagcccg accgctgcgc    6300
cttatccggt aactatcgtc ttgagtccaa cccggtaaga cacgacttat cgccactggc    6360
agcagccact ggtaacagga ttagcagagc gaggtatgta ggcggtgcta cagagttctt    6420
gaagtggtgg cctaactacg gctacactag aaggacagta tttggtatct gcgctctgct    6480
gaagccagtt accttcggaa aaagagttgg tagctcttga tccggcaaac aaaccaccgc    6540
tggtagcggt ggtttttttg tttgcaagca gcagattacg cgcagaaaaa aaggatctca    6600
agaagatcct ttgatctttt ctacggggtc tgacgctcag tggaacgaaa actcacgtta    6660
```

```
agggattttg gtcatgagat tatcaaaaag gatcttcacc tagatccttt taaattaaaa    6720
atgaagtttt aaatcaatct aaagtatata tgagtaaact tggtctgaca gttaccaatg    6780
cttaatcagt gaggcaccta tctcagcgat ctgtctattt cgttcatcca tagttgcctg    6840
actccccgtc gtgtagataa ctacgatacg ggagggctta ccatctggcc ccagtgctgc    6900
aatgataccg cgagacccac gctcaccggc tccagattta tcagcaataa accagccagc    6960
cggaagggcc gagcgcagaa gtggtcctgc aactttatcc gcctccatcc agtctattaa    7020
ttgttgccgg gaagctagag taagtagttc gccagttaat agtttgcgca acgttgttgc    7080
cattgctaca ggcatcgtgg tgtcacgctc gtcgtttggt atggcttcat tcagctccgg    7140
ttcccaacga tcaaggcgag ttacatgatc ccccatgttg tgcaaaaaag cggttagctc    7200
cttcggtcct ccgatcgttg tcagaagtaa gttggccgca gtgttatcac tcatggttat    7260
ggcagcactg cataattctc ttactgtcat gccatccgta agatgctttt ctgtgactgg    7320
tgagtactca accaagtcat tctgagaata gtgtatgcgg cgaccgagtt gctcttgccc    7380
ggcgtcaata cgggataata ccgcgccaca tagcagaact ttaaaagtgc tcatcattgg    7440
aaaacgttct cggggcgaaa actctcaag gatcttaccg ctgttgagat ccagttcgat    7500
gtaacccact cgtgcaccca actgatcttc agcatctttt actttcacca gcgtttctgg    7560
gtgagcaaaa acaggaaggc aaaatgccgc aaaaaaggga ataagggcga cacgaaatg    7620 ttgaatactc atactcttcc ttttt caata ttattgaagc atttatcagg gttattgtct    7680
catgagcgga tacatatttg aatgtattta gaaaaataaa caaataggggg ttccgcgcac    7740 atttccccga aaagtgccac ctg                                            7763

<210> SEQ ID NO 17
<211> LENGTH: 32
<212> TYPE: DNA
<213> ORGANISM: Artificial Sequence
<220> FEATURE:
<223> OTHER INFORMATION: Primer YZ4

<400> SEQUENCE: 17
tttatatagc ggccgcgctc actgcccgct tt                                  32

<210> SEQ ID NO 18
<211> LENGTH: 24
<212> TYPE: DNA
<213> ORGANISM: Artificial Sequence
<220> FEATURE:
<223> OTHER INFORMATION: Primer YZ5

<400> SEQUENCE: 18
gtgccaagct tgcatgccat ggta                                           24

<210> SEQ ID NO 19
<211> LENGTH: 7217
<212> TYPE: DNA
<213> ORGANISM: Artificial Sequence
<220> FEATURE:
<223> OTHER INFORMATION: pMTL-YZ007

<400> SEQUENCE: 19
cctgcaggat aaaaaaattg tagataaatt ttataaaata gttttatcta caatttttt     60 atcaggaaac agctatgacc gcggccgcgc tcactgcccg ctttccagtc gggaaacctg    120
tcgtgccagc tgcattaatg aatcggccaa cgcgcgggga gaggcggttt gcgtattggg    180
```

```
cgccagggtg gttttcttt tcaccagtga gacgggcaac agctgattgc ccttcaccgc    240
ctggccctga gagagttgca gcaagcggtc cacgctggtt tgccccagca ggcgaaaatc    300
ctgtttgatg gtggttaacg gcgggatata acatgagctg tcttcggtat cgtcgtatcc    360
cactaccgag atatccgcac caacgcgcag cccggactcg gtaatggcgc gcattgcgcc    420
cagcgccatc tgatcgttgg caaccagcat cgcagtggga acgatgccct cattcagcat    480
ttgcatggtt tgttgaaaac cggacatggc actccagtcg ccttcccgtt ccgctatcgg    540
ctgaatttga ttgcgagtga gatatttatg ccagccagcc agacgcagac gcgccgagac    600
agaacttaat gggcccgcta acagcgcgat ttgctggtga cccaatgcga ccagatgctc    660
cacgcccagt cgcgtaccgt cttcatggga gaaaataata ctgttgatgg gtgtctggtc    720
agagacatca agaaataacg ccggaacatt agtgcaggca gcttccacag caatggcatc    780
ctggtcatcc agcggatagt taatgatcag cccactgacg cgttgcgcga agagattgtg    840
caccgccgyt ttacaggctt cgacgccgct tcgttctacc atcgacacca ccacgctggc    900
acccagttga tcggcgcgag atttaatcgc cgcgacaatt tgcgacggcg cgtgcagggc    960
cagactggag gtggcaacgc caatcagcaa cgactgtttg cccgccagtt gttgtgccac   1020
gcggttggga atgtaattca gctccgccat cgccgcttcc actttttccc gcgttttcgc   1080
agaaacgtgg ctggcctggt tcaccacgcg ggaaacggtc tgataagaga caccggcata   1140
ctctgcgaca tcgtataacg ttactggttt catatgttgc acctctactt taataatttt   1200
taacttttat atatgattaa tttaattgtt tgttaaattt atatcaatca atgctatgaa   1260
tatttcttta taccttattg taacaaaaaa atattggaaa tgttgaattt tcagaatatt   1320
attttattta tattattaat tttatatatt cattttttata agatttcaca acacgaacgt   1380 aatataaatat atcttcctca tcttctgaaa agattatact aattctattc atgttactta   1440
taatcttatt ttggtaaatc gaatttttca attatatgtt cggcaacctt tatcccatca   1500
acagccgctg atattatacc acctgcaaat cctgccccct tctccagttgg ataaagtccg   1560 catacattta actttcaag tgaagcattt ctattcaatc taactggtgc tgatgttctt   1620
gtctcaattc ccgttaaaat tgcatcttct cttgcatacc cttttatctt tttatcaaaa   1680
tttataattc cttctttaag agcctctaca acataatcag gtaaacattc ttttaattcc   1740
ctgaattatc tgcagagaat tccccggatc gagatagtat atgatgcata ttctttaaat   1800
atagataaag ttatagaagc aatagaagat ttaggattta ctgtaatata aattacactt   1860
ttaaaaagtt taaaaacatg atacaataag ttatggttgg aattgttatc cgctcacaat   1920
tccaacttat gattaaaatt ttaaggaggt gtatttcata tgaccatgat tacgaattcg   1980
agctcggtac ccggggatcc ccatttagga ggcatatcaa atgaacttta taaaattga   2040 tttagacaat tggaagagaa aagagatatt taatcattat ttgaaccaac aaacgacttt   2100
tagtataacc acagaaattg atattagtgt tttataccga aacataaaac aagaaggata   2160
taaattttac cctgcattta ttttcttagt gacaagggtg ataaactcaa atacagcttt   2220
tagaactggt tacaatagcg acggagagtt aggttattgg gataagttag agccacttta   2280 tacaatttt gatggtgtat ctaaaacatt ctctggtatt tggactcctg taagaatga   2340 cttcaaagag ttttatgatt tatacctttc tgatgtagag aaatataatg gttcggggaa   2400
attgttcccc aaaacaccta acctgaaaa tgcttttct cttctatta ttccatggac   2460 ttcatttact gggtttaact taaatatcaa taataatagt aattaccttc tacccattat   2520
tacagcagga aaattcatta ataaaggtaa ttcaatatat ttaccgctat ctttacaggt   2580
```

```
acatcattct gtttgtgatg gttatcatgc aggattgttt atgaactcta ttcaggaatt   2640
gtcagatagg cctaatgact ggcttttata atatgagata atgccgactg tactttttac   2700
agtcggtttt ctaacgatac attaataggt acgaaaaagc aactttttt gcgcttaaaa    2760 ccagtcatac caataactta agggtaacta gcctcgccga tgggtaccat ggcatgcaag   2820
cttggcactg gccgtcgttt tacaacgtcg tgactgggaa aaccctggcg ttacccaact   2880
taatcgcctt gcagcacatc cccctttcgc cagctggcgt aatagcgaag aggcccgcac   2940
cgatcgccct tcccaacagt tgcgcagcct gaatggcgaa tggcgctagc ataaaaataa   3000
gaagcctgca tttgcaggct tcttattttt atggcgcgcc gccattattt ttttgaacaa   3060
ttgacaattc atttcttatt ttttattaag tgatagtcaa aaggcataac agtgctgaat   3120
agaaagaaat ttacagaaaa gaaaattata gaatttagta tgattaatta tactcattta   3180
tgaatgttta attgaataca aaaaaaaata cttgttatgt attcaattac gggttaaaat   3240
atagacaagt tgaaaaattt aataaaaaaa taagtcctca gctcttatat attaagctac   3300
caacttagta tataagccaa aacttaaatg tgctaccaac acatcaagcc gttagagaac   3360
tctatctata gcaatatttc aaatgtaccg acatacaaga gaaacattaa ctatatatat   3420
tcaatttatg agattatctt aacagatata aatgtaaatt gcaataagta agatttagaa   3480
gtttatagcc tttgtgtatt ggaagcagta cgcaaaggct ttttatttg ataaaaatta    3540 gaagtatatt tattttttca taattaattt atgaaaatga aaggggtga gcaaagtgac    3600 agaggaaagc agtatcttat caaataacaa ggtattagca atatcattat tgactttagc   3660
agtaaacatt atgactttta tagtgcttgt agctaagtag tacgaaaggg ggagctttaa   3720 aaagctccctt ggaatacata gaattcataa attaatttat gaaagaagg gcgtatatga   3780 aaacttgtaa aaattgcaaa gagtttatta aagatactga aatatgcaaa atacattcgt   3840
tgatgattca tgataaaaca gtagcaacct attgcagtaa atacaatgag tcaagatgtt   3900
tacataaagg gaaagtccaa tgtattaatt gttcaaagat gaaccgatat ggatggtgtg   3960
ccataaaaat gagatgtttt acagaggaag aacagaaaaa agaacgtaca tgcattaaat   4020
attatgcaag gagctttaaa aaagctcatg taaagaagag taaaagaaa aaataattta    4080 tttattaatt taatattgag agtgccgaca cagtatgcac taaaaaatat atctgtggtg   4140
tagtgagccg atacaaaagg atagtcactc gcattttcat aatacatctt atgttatgat   4200
tatgtgtcgg tgggacttca cgacgaaaac ccacaataaa aaaagagttc ggggtagggt   4260
taagcatagt tgaggcaact aaacaatcaa gctaggatat gcagtagcag accgtaaggt   4320
cgttgtttag gtgtgttgta atacatacgc tattaagatg taaaaatacg gataccaatg   4380
aagggaaaag tataattttt ggatgtagtt tgtttgttca tctatgggca aactacgtcc   4440
aaagccgttt ccaaatctgc taaaaagtat atcctttcta aaatcaaagt caagtatgaa   4500
atcataaata aagtttaatt ttgaagttat tatgatatta tgtttttcta ttaaaataaa   4560
ttaagtatat agaatagttt aataatagta tatacttaat gtgataagtg tctgacagtg   4620
tcacagaaag gatgattgtt atggattata agcggccggc cgaagcaaac ttaagagtgt   4680
gttgatagtg cagtatctta aaatttttgta taataggaat tgaagttaaa ttagatgcta   4740
aaaatttgta attaagaagg agtgattaca tgaacaaaaa tataaaatat tctcaaaact   4800
ttttaacgag tgaaaagta ctcaaccaaa taataaaaca attgaattta aaagaaaccg    4860
ataccgttta cgaaattgga acaggtaaag ggcatttaac gacgaaactg gctaaaataa   4920
```

```
gtaaacaggt aacgtctatt gaattagaca gtcatctatt caacttatcg tcagaaaaat    4980
taaaactgaa tactcgtgtc actttaattc accaagatat tctacagttt caattcccta    5040
acaaacagag gtataaaatt gttgggagta ttccttacca tttaagcaca caaattatta    5100
aaaaagtggt ttttgaaagc catgcgtctg acatctatct gattgttgaa gaaggattct    5160
acaagcgtac cttggatatt caccgaacac tagggttgct cttgcacact caagtctcga    5220
ttcagcaatt gcttaagctg ccagcggaat gctttcatcc taaaccaaaa gtaaacagtg    5280
tcttaataaa acttacccgc cataccacag atgttccaga taatattgg aagctatata     5340 cgtactttgt ttcaaaatgg gtcaatcgag aatatcgtca actgtttact aaaaatcagt    5400
ttcatcaagc aatgaaacac gccaaagtaa acaatttaag taccgttact tatgagcaag    5460
tattgtctat ttttaatagt tatctattat ttaacgggag gaaataattc tatgagtcgc    5520
ttttgtaaat ttggaaagtt acacgttact aaagggaatg tgtttaaact ccttttttgat   5580 aatctcatga ccaaaatccc ttaacgtgag ttttcgttcc actgagcgtc agaccccgta    5640
gaaaagatca aaggatcttc ttgagatcct ttttttctgc gcgtaatctg ctgcttgcaa    5700
acaaaaaaac caccgctacc agcggtggtt tgtttgccgg atcaagagct accaactctt    5760
tttccgaagg taactggctt cagcagagcg cagataccaa atactgttct tctagtgtag    5820
ccgtagttag gccaccactt caagaactct gtagcaccgc ctacatacct cgctctgcta    5880
atcctgttac cagtggctgc tgccagtggc gataagtcgt gtcttaccgg gttggactca    5940
agacgatagt taccggataa ggcgcagcgg tcgggctgaa cggggggttc gtgcacacag    6000
cccagcttgg agcgaacgac ctacaccgaa ctgagatacc tacagcgtga gctatgagaa    6060
agcgccacgc ttcccgaagg gagaaaggcg gacaggtatc cggtaagcgg cagggtcgga    6120
acaggagagc gcacgaggga gcttccaggg ggaaacgcct ggtatcttta tagtcctgtc    6180
gggtttcgcc acctctgact tgagcgtcga ttttgtgat gctcgtcagg ggggcggagc     6240
ctatggaaaa acgccagcaa cgcggccttt ttacggttcc tggccttttg ctggccttt     6300 gctcacatgt tctttcctgc gttatcccct gattctgtgg ataaccgtat taccgccttt    6360
gagtgagctg ataccgctcg ccgcagccga acgaccgagc gcagcgagtc agtgagcgag    6420
gaagcggaag agcgcccaat acgcagggcc ccctgcttcg gggtcattat agcgattttt    6480
tcggtatatc catcctttt cgcacgatat acaggatttt gccaaagggt tcgtgtagac     6540
tttccttggt gtatccaacg gcgtcagccg ggcaggatag gtgaagtagg cccacccgcg    6600
agcgggtgtt ccttcttcac tgtcccttat tcgcacctgg cggtgctcaa cgggaatcct    6660
gctctgcgag gctggccggc taccgccggc gtaacagatg agggcaagcg gatggctgat    6720
gaaaccaagc caaccaggaa gggcagccca cctatcaagg tgtactgcct tccagacgaa    6780
cgaagagcga ttgaggaaaa ggcggcggcg gccggcatga gcctgtcggc ctacctgctg    6840
gccgtcggcc agggctacaa aatcacgggc gtcgtggact atgagcacgt ccgcgagctg    6900
gcccgcatca atgcggacct gggccgcctg ggcggcctgc tgaaactctg gctcaccgac    6960
gacccgcgca cggcgcggtt cggtgatgcc acgatcctcg ccctgctggc gaagatcgaa    7020
gagaagcagg acgagcttgg caaggtcatg atgggcgtgg tccgcccgag ggcagagcca    7080
tgactttttt agccgctaaa acggccgggg ggtgcgcgtg attgccaagc acgtccccat    7140
gcgctccatc aagaagagcg acttcgcgga gctggtgaag tacatcaccg acgagcaagg    7200
caagaccgat cgggccc                                                   7217
```

<210> SEQ ID NO 20
<211> LENGTH: 1920
<212> TYPE: DNA
<213> ORGANISM: Artificial Sequence
<220> FEATURE:
<223> OTHER INFORMATION: inducible expression cassette

<400> SEQUENCE: 20

```
gcggccgcgc tcactgcccg ctttccagtc gggaaacctg tcgtgccagc tgcattaatg      60
aatcggccaa cgcgcgggga gaggcggttt gcgtattggg cgccagggtg ttttttcttt     120
tcaccagtga cgggcaac agctgattgc ccttcaccgc ctggccctga gagagttgca       180
gcaagcggtc cacgctggtt tgccccagca ggcgaaaatc ctgtttgatg gtggttaacg     240
gcgggatata acatgagctg tcttcggtat cgtcgtatcc cactaccgag atatccgcac     300
caacgcgcag cccggactcg gtaatggcgc gcattgcgcc cagcgccatc tgatcgttgg     360
caaccagcat cgcagtggga acgatgccct cattcagcat ttgcatggtt tgttgaaaac     420
cggacatggc actccagtcg ccttcccgtt ccgctatcgg ctgaatttga ttgcgagtga     480
gatatttatg ccagccagcc agacgcagac gcgccgagac agaacttaat gggcccgcta     540
acagcgcgat ttgctggtga cccaatgcga ccagatgctc cacgcccagt cgcgtaccgt     600
cttcatggga gaaaataata ctgttgatgg gtgtctggtc agagacatca agaaataacg     660
ccggaacatt agtgcaggca gcttccacag caatggcatc ctggtcatcc agcggatagt     720
taatgatcag cccactgacg cgttgcgcga agattgtg caccgccgyt ttacaggctt       780
cgacgccgct tcgttctacc atcgacacca ccacgctggc acccagttga tcggcgcgag     840
atttaatcgc cgcgacaatt tgcgacggcg cgtgcagggc cagactggag gtggcaacgc     900
caatcagcaa cgactgtttg cccgccagtt gttgtgccac gcggttggga atgtaattca     960
gctccgccat cgccgcttcc acttttttccc gcgttttcgc agaaacgtgg ctggcctggt    1020
tcaccacgcg ggaaacggtc tgataagaga caccggcata ctctgcgaca tcgtataacg    1080
ttactggttt catatgttgc acctctactt taataatttt taactttat atatgattaa     1140
tttaattgtt tgttaaattt atatcaatca atgctatgaa tatttctttta taccttattg    1200
taacaaaaaa atattggaaa tgttgaattt tcagaatatt attttattta tattattaat    1260
tttatatatt cattttata agatttcaca acacgaacgt aatataatat atcttcctca    1320
tcttctgaaa agattatact aattctattc atgttactta taatcttatt ttggtaaatc    1380
gaattttca attatatgtt cggcaacctt tatcccatca acagccgctg atattatacc    1440
acctgcaaat cctgcccctt ctccagttgg ataaagtccg catacattta tactttcaag    1500
tgaagcattt ctattcaatc taactggtgc tgatgttctt gtctcaattc ccgttaaaat    1560
tgcatcttct cttgcatacc ttttatcctt tttatcaaaa tttataattc cttctttaag    1620
agcctctaca acataatcag gtaaacattc ttttaattcc ctgaattatc tgcagagaat    1680
tcccccggatc gagatagtat atgatgcata ttctttaaat atagataaag ttatagaagc    1740
aatagaagat ttaggattta ctgtaatata aattcacctt ttaaaagtt taaaaacatg     1800
atacaataag ttatggttgg aattgttatc cgctcacaat tccaacttat gattaaaatt    1860
ttaaggaggt gtatttcata tgaccatgat tacgaattcg agctcggtac ccggggatcc    1920
```

<210> SEQ ID NO 21
<211> LENGTH: 6398
<212> TYPE: DNA
<213> ORGANISM: Artificial Sequence
<220> FEATURE:

<223> OTHER INFORMATION: pMTL-YZ008

<400> SEQUENCE: 21

```
cctgcaggat aaaaaaattg tagataaatt ttataaaata gttttatcta caatttttttt    60
atcaggaaac agctatgacc gcggccgcgc tcactgcccg ctttccagtc gggaaacctg   120
tcgtgccagc tgcattaatg aatcggccaa cgcgcgggga gaggcggttt gcgtattggg   180
cgccagggtg ttttttcttt tcaccagtga cacgggcaac agctgattgc ccttcaccgc   240
ctggccctga gagagttgca gcaagcggtc cacgctggtt tgccccagca ggcgaaaatc   300
ctgtttgatg gtggttaacg gcgggatata acatgagctg tcttcggtat cgtcgtatcc   360
cactaccgag atatccgcac caacgcgcag cccggactcg gtaatggcgc gcattgcgcc   420
cagcgccatc tgatcgttgg caaccagcat cgcagtggga acgatgccct cattcagcat   480
ttgcatggtt tgttgaaaac cggacatggc actccagtcg ccttcccgtt ccgctatcgg   540
ctgaatttga ttgcgagtga gatatttatg ccagccagcc agacgcagac gcgccgagac   600
agaacttaat gggcccgcta acagcgcgat ttgctggtga cccaatgcga ccagatgctc   660
cacgcccagt cgcgtaccgt cttcatggga gaaaataata ctgttgatgg gtgtctggtc   720
agagacatca agaaataacg ccggaacatt agtgcaggca gcttccacag caatggcatc   780
ctggtcatcc agcggatagt taatgatcag cccactgacg cgttgcgcga agagattgtg   840
caccgccgyt ttacaggctt cgacgccgct tcgttctacc atcgacacca ccacgctggc   900
acccagttga tcggcgcgag atttaatcgc cgcgacaatt tgcgacggcg cgtgcagggc   960
cagactggag gtggcaacgc caatcagcaa cgactgtttg cccgccagtt gttgtgccac  1020
gcggttggga atgtaattca gctccgccat cgccgcttcc actttttccc gcgttttcgc  1080
agaaacgtgg ctggcctggt tcaccacgcg ggaaacggtc tgataagaga caccggcata  1140
ctctgcgaca tcgtataacg ttactggttt catatgttgc acctctactt taataatttt  1200
taacttttat atatgattaa tttaattgtt tgttaaattt atatcaatca atgctatgaa  1260
tatttcttta taccttattg taacaaaaaa atattggaaa tgttgaattt tcagaatatt  1320
atttttatta tattattaat tttatatatt cattttttata agatttcaca acacgaacgt  1380
aatataatat atcttcctca tcttctgaaa agattatact aattctattc atgttactta  1440
taatcttatt ttggtaaatc gaattttttca attatatgtt cggcaacctt tatcccatca  1500
acagccgctg atattatacc acctgcaaat cctgcccctt ctccagttgg ataaagtccg  1560
catacattta tactttcaag tgaagcattt ctattcaatc taactggtgc tgatgttctt  1620
gtctcaattc ccgttaaaat tgcatcttct cttgcatacc ctttttatctt tttatcaaaa  1680
tttataattc cttctttaag agcctctaca acataatcag gtaaacattc ttttaattcc  1740
ctgaattatc tgcagagaat tccccggatc gagatagtat atgatgcata ttctttaaat  1800
atagataaag ttatagaagc aatagaagat ttaggattta ctgtaatata aattacactt  1860
ttaaaaagtt taaaaacatg atacaataag ttatggttgg aattgttatc cgctcacaat  1920
tccaacttat gattaaaatt ttaaggaggt gtatttcata tgaccatgat tacgaattcg  1980
agctcggtac ccggggatca gcttggcact ggccgtcgtt ttacaacgtc gtgactggga  2040
aaaccctggc gttacccaac ttaatcgcct tgcagcacat ccccctttcg ccagctggcg  2100
taatagcgaa gaggcccgca ccgatcgccc ttcccaacag ttgcgcagcc tgaatggcga  2160
atggcgctag cataaaaaata agaagcctgc atttgcaggc ttcttatttt tatgcgcgc   2220
cgccattatt ttttgaaca attgacaatt catttcttat ttttttattaa gtgatagtca  2280
```

```
aaaggcataa cagtgctgaa tagaaagaaa tttacagaaa agaaaattat agaatttagt   2340
atgattaatt atactcattt atgaatgttt aattgaatac aaaaaaaaat acttgttatg   2400
tattcaatta cgggttaaaa tatagacaag ttgaaaaatt taataaaaaa ataagtcctc   2460
agctcttata tattaagcta ccaacttagt atataagcca aaacttaaat gtgctaccaa   2520
cacatcaagc cgttagagaa ctctatctat agcaatattt caaatgtacc gacatacaag   2580
agaaacatta actatatata ttcaatttat gagattatct aacagatat  aaatgtaaat   2640 tgcaataagt aagatttaga agtttatagc ctttgtgtat tggaagcagt acgcaaaggc   2700
ttttttattt gataaaaatt agaagtatat ttatttttc  ataattaatt tatgaaaatg   2760
aaggggggtg agcaaagtga cagaggaaag cagtatctta tcaaataaca aggtattagc   2820
aatatcatta ttgactttag cagtaaacat tatgactttt atagtgcttg tagctaagta   2880
gtacgaaagg gggagcttta aaaagctcct tggaatacat agaattcata aattaattta   2940 tgaaagaag  ggcgtatatg aaaacttgta aaaattgcaa agagtttatt aaagatactg   3000
aaatatgcaa aatacattcg ttgatgattc atgataaaac agtagcaacc tattgcagta   3060
aatacaatga gtcaagatgt ttacataaag ggaaagtcca atgtattaat tgttcaaaga   3120
tgaaccgata tggatggtgt gccataaaaa tgagatgttt tacagaggaa gaacagaaaa   3180
aagaacgtac atgcattaaa tattatgcaa ggagctttaa aaaagctcat gtaaagaaga   3240 gtaaaagaa  aaaataattt atttattaat ttaatattga gagtgccgac acagtatgca   3300
ctaaaaaata tatctgtggt gtagtgagcc gatacaaaag gatagtcact cgcattttca   3360
taatacatct tatgttatga ttatgtgtcg gtgggacttc acgacgaaaa cccacaataa   3420
aaaaagagtt cggggtaggg ttaagcatag ttgaggcaac taaacaatca agctaggata   3480
tgcagtagca gaccgtaagg tcgttgttta ggtgtgttgt aatacatacg ctattaagat   3540
gtaaaaatac ggataccaat gaagggaaaa gtataatttt tggatgtagt ttgtttgttc   3600
atctatgggc aaactacgtc caaagccgtt tccaaatctg ctaaaaagta tatcctttct   3660
aaaatcaaag tcaagtatga aatcataaat aaagtttaat tttgaagtta ttatgatatt   3720 atgttttct  attaaaataa attaagtata tagaatagtt taataatagt atatacttaa   3780
tgtgataagt gtctgacagt gtcacagaaa ggatgattgt tatggattat aagcggccgg   3840
ccgaagcaaa cttaagagtg tgttgatagt gcagtatctt aaaattttgt ataataggaa   3900
ttgaagttaa attagatgct aaaaatttgt aattaagaag gagtgattac atgaacaaaa   3960
atataaaata ttctcaaaac tttttaacga gtgaaaaagt actcaaccaa ataataaaac   4020
aattgaattt aaaagaaacc gataccgttt acgaaattgg aacaggtaaa gggcatttaa   4080
cgacgaaact ggctaaaata agtaaacagg taacgtctat tgaattagac agtcatctat   4140
tcaacttatc gtcagaaaaa ttaaaactga atactcgtgt cactttaatt caccaagata   4200
ttctacagtt tcaattccct aacaaacaga ggtataaaat tgttgggagt attccttacc   4260
atttaagcac acaaattatt aaaaaagtgg ttttttgaaag ccatgcgtct gacatctatc   4320
tgattgttga agaaggattc tacaagcgta ccttggatat tcaccgaaca ctagggttgc   4380
tcttgcacac tcaagtctcg attcagcaat tgcttaagct gccagcggaa tgctttcatc   4440
ctaaaccaaa agtaaacagt gtcttaataa aacttacccg ccataccaca gatgttccag   4500
ataaatattg gaagctatat acgtactttg tttcaaaatg ggtcaatcga gaatatcgtc   4560
aactgtttac taaaaatcag tttcatcaag caatgaaaca cgccaaagta aacaatttaa   4620
```

| | |
|---|---:|
| gtaccgttac ttatgagcaa gtattgtcta tttttaatag ttatctatta tttaacggga | 4680 |
| ggaaataatt ctatgagtcg cttttgtaaa tttggaaagt tacacgttac taaagggaat | 4740 |
| gtgtttaaac tccttttga taatctcatg accaaaatcc cttaacgtga gttttcgttc | 4800 |
| cactgagcgt cagaccccgt agaaaagatc aaaggatctt cttgagatcc ttttttctg | 4860 |
| cgcgtaatct gctgcttgca acaaaaaaa ccaccgctac cagcggtggt ttgtttgccg | 4920 |
| gatcaagagc taccaactct ttttccgaag gtaactggct tcagcagagc gcagatacca | 4980 |
| aatactgttc ttctagtgta gccgtagtta ggccaccact tcaagaactc tgtagcaccg | 5040 |
| cctacatacc tcgctctgct aatcctgtta ccagtggctg ctgccagtgg cgataagtcg | 5100 |
| tgtcttaccg ggttggactc aagacgatag ttaccggata aggcgcagcg tcgggctga | 5160 |
| acggggggtt cgtgcacaca gcccagcttg gagcgaacga cctacaccga actgagatac | 5220 |
| ctacagcgtg agctatgaga aagcgccacg cttcccgaag ggagaaaggc ggacaggtat | 5280 |
| ccggtaagcg gcagggtcgg aacaggagag cgcacgaggg agcttccagg gggaaacgcc | 5340 |
| tggtatcttt atagtcctgt cgggtttcgc cacctctgac ttgagcgtcg attttgtga | 5400 |
| tgctcgtcag gggggcggag cctatggaaa aacgccagca acgcggcctt tttacggttc | 5460 |
| ctggccttt gctggccttt tgctcacatg ttctttcctg cgttatcccc tgattctgtg | 5520 |
| gataaccgta ttaccgcctt tgagtgagct gataccgctc gccgcagccg aacgaccgag | 5580 |
| cgcagcgagt cagtgagcga ggaagcggaa gagcgcccaa tacgcagggc ccctgcttc | 5640 |
| ggggtcatta tagcgatttt ttcggtatat ccatccttt tcgcacgata tacaggattt | 5700 |
| tgccaaaggg ttcgtgtaga ctttccttgg tgtatccaac ggcgtcagcc gggcaggata | 5760 |
| ggtgaagtag gcccacccgc gagcgggtgt tccttcttca ctgtccctta ttcgcacctg | 5820 |
| gcggtgctca acgggaatcc tgctctgcga ggctggccgg ctaccgccgg cgtaacagat | 5880 |
| gagggcaagc ggatggctga tgaaaccaag ccaaccagga agggcagccc acctatcaag | 5940 |
| gtgtactgcc ttccagacga acgaagagcg attgaggaaa aggcggcggc ggccggcatg | 6000 |
| agcctgtcgg cctacctgct ggccgtcggc cagggctaca aaatcacggg cgtcgtggac | 6060 |
| tatgagcacg tccgcgagct ggcccgcatc aatggcgacc tgggccgcct gggcggcctg | 6120 |
| ctgaaactct ggctcaccga cgacccgcgc acggcgcggt tcggtgatgc cacgatcctc | 6180 |
| gccctgctgg cgaagatcga agagaagcag gacgagcttg gcaaggtcat gatgggcgtg | 6240 |
| gtccgcccga gggcagagcc atgactttt tagccgctaa acggccggg gggtgcgcgt | 6300 |
| gattgccaag cacgtcccca tgcgctccat caagaagagc gacttcgcgg agctggtgaa | 6360 |
| gtacatcacc gacgagcaag gcaagaccga tcgggccc | 6398 |

<210> SEQ ID NO 22
<211> LENGTH: 6182
<212> TYPE: DNA
<213> ORGANISM: Artificial Sequence
<220> FEATURE:
<223> OTHER INFORMATION: pMTL-YZ009

<400> SEQUENCE: 22

| | |
|---|---:|
| cctgcaggat aaaaaattg tagataaatt ttataaaata gttttatcta caatttttt | 60 |
| atcaggaaac agctatgacc gcggccgcgc tcactgcccg ctttccagtc gggaaacctg | 120 |
| tcgtgccagc tgcattaatg aatcggccaa cgcgcgggga gaggcggttt gcgtattggg | 180 |
| cgccagggtg gtttttcttt tcaccagtga cgggcaac agctgattgc ccttcaccgc | 240 |
| ctggccctga gagagttgca gcaagcggtc cacgctggtt tgccccagca ggcgaaaatc | 300 |

```
ctgtttgatg gtggttaacg gcgggatata acatgagctg tcttcggtat cgtcgtatcc   360
cactaccgag atatccgcac caacgcgcag cccggactcg gtaatggcgc gcattgcgcc   420
cagcgccatc tgatcgttgg caaccagcat cgcagtggga acgatgccct cattcagcat   480
ttgcatggtt tgttgaaaac cggacatggc actccagtcg ccttcccgtt ccgctatcgg   540
ctgaatttga ttgcgagtga gatatttatg ccagccagcc agacgcagac gcgccgagac   600
agaacttaat gggcccgcta acagcgcgat ttgctggtga cccaatgcga ccagatgctc   660
cacgcccagt cgcgtaccgt cttcatggga gaaaataata ctgttgatgg tgtctggtc    720
agagacatca agaaataacg ccggaacatt agtgcaggca gcttccacag caatggcatc   780
ctggtcatcc agcggatagt taatgatcag cccactgacg cgttgcgcga agagattgtg   840
caccgccgyt ttacaggctt cgacgccgct tcgttctacc atcgacacca ccacgctggc   900
acccagttga tcggcgcgag atttaatcgc cgcgacaatt tgcgacggcg cgtgcagggc   960
cagactggag gtggcaacgc caatcagcaa cgactgtttg cccgccagtt gttgtgccac  1020
gcggttggga atgtaattca gctccgccat cgccgcttcc acttttttccc gcgttttcgc  1080
agaaacgtgg ctggcctggt tcaccacgcg ggaaacggtc tgataagaga caccggcata  1140
ctctgcgaca tcgtataacg ttactggttt catatgttgc acctctactt taataatttt  1200
taacttttat atatgattaa tttaattgtt tgttaaattt atatcaatca atgctatgaa  1260
tatttcttta taccttattg taacaaaaaa atattggaaa tgttgaattt tcagaatatt  1320
attttttatta tattattaat tttatatatt cattttttata agatttcaca acacgaacgt  1380
aatataatat atcttcctca tcttctgaaa agattatact aattctattc atgttactta  1440
taatcttatt ttggtaaatc gaattttttca attatatgtt cggcaacctt tatcccatca  1500
acagccgctg atattatacc acctgcaaat cctgccccctt ctccagttgg ataaagtccg  1560
catacattta tactttcaag tgaagcattt ctattcaatc taactggtgc tgatgttctt  1620
gtctcaattc ccgttaaaat tgcatcttct cttgcatacc cttttatctt tttatcaaaa  1680
tttataattc cttctttaag agcctctaca acataatcag gtaaacattc ttttaattcc  1740
ctgaattatc tgcagagaat tccccggatc gagatagtat atgatgcata ttctttaaat  1800
atagataaag ttatagaagc aatagaagat ttaggattta ctgtaatata aattcacctt  1860
ttaaaaagtt taaaaacatg atacaataag ttatggttgg aattgttatc cgctcacaat  1920
tccaacttat gattaaaatt ttaaggaggt gtatttcata tgaccatgat tacgaattcg  1980
agctcggtac ccggggatcc gcgccgccat tattttttttg aacaattgac aattcatttc  2040
ttattttttta ttaagtgata gtcaaaaggc ataacagtgc tgaatagaaa gaaatttaca  2100
gaaaagaaaa ttatagaatt tagtatgatt aattatactc atttatgaat gtttaattga  2160
atacaaaaaa aaatacttgt tatgtattca attacgggtt aaaatataga caagttgaaa  2220
aatttaataa aaaaataagt cctcagctct tatatattaa gctaccaact tagtatataa  2280
gccaaaactt aaatgtgcta ccaacacatc aagccgttag agaactctat ctatagcaat  2340
atttcaaatg taccgacata caagagaaac attaactata tatattcaat ttatgagatt  2400
atcttaacag atataaatgt aaattgcaat aagtaagatt tagaagttta tagcctttgt  2460
gtattggaag cagtacgcaa aggctttttt atttgataaa aattagaagt atatttatttt  2520
tttcataatt aatttatgaa atgaaagggg ggtgagcaaa gtgacagagg aaagcagtat  2580
cttatcaaat aacaaggtat tagcaatatc attattgact ttagcagtaa acattatgac  2640
```

```
ttttatagtg cttgtagcta agtagtacga aaggggagc tttaaaaagc tccttggaat   2700
acatagaatt cataaattaa tttatgaaaa gaagggcgta tatgaaaact tgtaaaaatt   2760
gcaaagagtt tattaaagat actgaaatat gcaaaataca ttcgttgatg attcatgata   2820
aaacagtagc aacctattgc agtaaataca atgagtcaag atgtttacat aaagggaaag   2880
tccaatgtat taattgttca agatgaacc gatatggatg gtgtgccata aaaatgagat   2940
gttttacaga ggaagaacag aaaaaagaac gtacatgcat taaatattat gcaaggagct   3000
ttaaaaagc tcatgtaaag aagagtaaaa agaaaaaata atttatttat taatttaata   3060
ttgagagtgc cgacacagta tgcactaaaa aatatatctg tggtgtagtg agccgataca   3120
aaaggatagt cactcgcatt tcataatac atcttatgtt atgattatgt gtcggtggga   3180
cttcacgacg aaaacccaca ataaaaaaag agttcggggt agggttaagc atagttgagg   3240
caactaaaca atcaagctag gatatgcagt agcagaccgt aaggtcgttg tttaggtgtg   3300
ttgtaataca tacgctatta agatgtaaaa atacggatac caatgaaggg aaaagtataa   3360
tttttggatg tagtttgttt gttcatctat gggcaaacta cgtccaaagc cgtttccaaa   3420
tctgctaaaa agtatatcct ttctaaaatc aaagtcaagt atgaaatcat aaataaagtt   3480
taattttgaa gttattatga tattatgttt ttctattaaa ataaattaag tatatagaat   3540
agtttaataa tagtatatac ttaatgtgat aagtgtctga cagtgtcaca gaaaggatga   3600
ttgttatgga ttataagcgg ccggccgaag caaacttaag agtgtgttga tagtgcagta   3660
tcttaaaatt ttgtataata ggaattgaag ttaaattaga tgctaaaaat ttgtaattaa   3720
gaaggagtga ttacatgaac aaaaatataa aatattctca aaacttttta acgagtgaaa   3780
aagtactcaa ccaaataata aaacaattga atttaaaaga aaccgatacc gtttacgaaa   3840
ttggaacagg taagggcat ttaacgacga aactggctaa aataagtaaa caggtaacgt   3900
ctattgaatt agacagtcat ctattcaact tatcgtcaga aaaattaaaa ctgaatactc   3960
gtgtcacttt aattcaccaa gatattctac agtttcaatt ccctaacaaa cagaggtata   4020
aaattgttgg gagtattcct taccatttaa gcacacaaat tattaaaaaa gtggttttttg   4080
aaagccatgc gtctgacatc tatctgattg ttgaagaagg attctacaag cgtaccttgg   4140
atattcaccg aacactaggg ttgctcttgc acactcaagt ctcgattcag caattgctta   4200
agctgccagc ggaatgcttt catcctaaac caaaagtaaa cagtgtctta ataaaactta   4260
cccgccatac cacagatgtt ccagataaat attggaagct atatacgtac tttgtttcaa   4320
aatgggtcaa tcgagaatat cgtcaactgt ttactaaaaa tcagtttcat caagcaatga   4380
aacacgccaa agtaaacaat ttaagtaccg ttacttatga gcaagtattg tctatttttta   4440
atagttatct attatttaac gggaggaaat aattctatga gtcgcttttg taaatttgga   4500
aagttacacg ttactaaagg gaatgtgttt aaactccttt ttgataatct catgaccaaa   4560
atcccttaac gtgagttttc gttccactga gcgtcagacc ccgtagaaaa gatcaaagga   4620
tcttcttgag atccttttt tctgcgcgta atctgctgct tgcaaacaaa aaaaccaccg   4680
ctaccagcgg tggtttgttt gccggatcaa gagctaccaa ctcttttcc gaaggtaact   4740
ggcttcagca gagcgcagat accaaatact gttcttctag tgtagccgta gttaggccac   4800
cacttcaaga actctgtagc accgcctaca tacctcgctc tgctaatcct gttaccagtg   4860
gctgctgcca gtggcgataa gtcgtgtctt accgggttgg actcaagacg atagttaccg   4920
gataaggcgc agcggtcggg ctgaacgggg ggttcgtgca cacagcccag cttggagcga   4980
acgacctaca ccgaactgag atacctacag cgtgagctat gagaaagcgc cacgcttccc   5040
```

```
gaagggagaa aggcggacag gtatccggta agcggcaggg tcggaacagg agagcgcacg    5100
agggagcttc caggggggaaa cgcctggtat ctttatagtc ctgtcgggtt tcgccacctc    5160
tgacttgagc gtcgattttt gtgatgctcg tcagggggggc ggagcctatg gaaaaacgcc    5220
agcaacgcgg cctttttacg gttcctggcc ttttgctggc cttttgctca catgttcttt    5280
cctgcgttat ccctgattc tgtggataac cgtattaccg cctttgagtg agctgatacc    5340
gctcgccgca gccgaacgac cgagcgcagc gagtcagtga gcgaggaagc ggaagagcgc    5400
ccaatacgca gggcccctg cttcggggtc attatagcga ttttttcggt atatccatcc    5460
tttttcgcac gatatacagg attttgccaa agggttcgtg tagactttcc ttggtgtatc    5520
caacggcgtc agccgggcag gataggtgaa gtaggcccac ccgcgagcgg gtgttccttc    5580
ttcactgtcc cttattcgca cctggcggtg ctcaacggga atcctgctct gcgaggctgg    5640
ccggctaccg ccggcgtaac agatgagggc aagcggatgg ctgatgaaac caagccaacc    5700
aggaagggca gcccacctat caaggtgtac tgccttccag acgaacgaag agcgattgag    5760
gaaaaggcgg cggcggccgg catgagcctg tcggcctacc tgctggccgt cggccagggc    5820
tacaaaatca cgggcgtcgt ggactatgag cacgtccgcg agctgcccg catcaatggc    5880 gacctgggcc gcctgggcgg cctgctgaaa ctctggctca ccgacgaccc gcgcacggcg    5940
cggttcggtg atgccacgat cctcgccctg ctggcgaaga tcgaagagaa gcaggacgag    6000
cttggcaagg tcatgatggg cgtggtccgc ccgagggcag agccatgact tttttagccg    6060
ctaaaacggc cggggggtgc gcgtgattgc caagcacgtc cccatgcgct ccatcaagaa    6120
gagcgacttc gcggagctgg tgaagtacat caccgacgag caaggcaaga ccgatcgggc    6180
cc                                                                   6182
```

<210> SEQ ID NO 23
<211> LENGTH: 913
<212> TYPE: DNA
<213> ORGANISM: Artificial Sequence
<220> FEATURE:
<223> OTHER INFORMATION: TetR cassette

<400> SEQUENCE: 23

```
gcggccgcgg cgccaagctt agaaaaatat aaataagaag tagctttaag agaattaaat      60
tattaagaaa agcaaaggtg tttaaaaaat aaattttaa acacctttgc ttttcttaaa     120
ttataaataa gataaaaaag aatcctgaat aaaataaaaa ggggtgtctc aaaattttat    180
tttgagacga ccccttttta ttctatatgt cgatgctata gctgagatcg tggaattctt    240
gttagctacc agattcacat ttaagttgtt tctctaaacc acagattatc aattcaagtc    300 caaaagaaa tgctggttct gcgccttgat gatcaaataa ctctattgct tgtcttaaca    360
atggaggcat tgaatctgtt gttggtgttt ctctttcctc ttttgcaact tgatgttctt    420
gatcctccaa tacgcaacct aaagtaaaat gtcctacagc acttagtgcg tataaggcat    480
tttctaaact aaaaccctgt tgacataaga atgctaattg attttctaat gtttcatatt    540
gtttttcagt tggtctagtt cctaaatgta ctttagcccc atctctatgt gataatagag    600
cacaacgaaa agatttagcg ttattcctaa gaaaatcttg ccatgattca ccttctaaag    660
gacaaaagtg agtgtgatgt ctatctaaca tttcaatagc taaggcgtca agtaaagctc    720
tcttattctt cacatgccaa tacaacgtag gttgttctac tccaagtttc tgagctaact    780
ttcttgtagt tagtccttct attccaactt catttagtaa ttccaatgca ctattgataa    840
```

-continued

```
ctttactttt atcaagtcta gacatcattt aatatcctcc tcttcaatat atttaagtcg    900
actgatcgga tcc                                                       913

<210> SEQ ID NO 24
<211> LENGTH: 7169
<212> TYPE: DNA
<213> ORGANISM: Artificial Sequence
<220> FEATURE:
<223> OTHER INFORMATION: pMTL-tet3nO

<400> SEQUENCE: 24
aagtaaggaa aaaaagaag taagtgttat atatgatgat tattttgtag atgtagatag      60
gataatagaa tccatagaaa ataggttta tacagttata taaaaattac tttaaaatct    120
atcattgata gggtaaaata taaatcgtat aaagttgtgt aattttttaag gaggtgtgtt   180 acagacgtcc gcgagagacc ttaaatatat tgaagaggag gaaatacata tggtatttga   240
aaaaattgat aaaaatagtt ggaacagaaa agagtatttt gaccactact ttgcaagtgt   300
accttgtacc tacagcatga ccgttaaagt ggatatcaca caaataaagg aaagggaat    360 gaaactatat cctgcaatgc tttattatat tgcaatgatt gtaaaccgcc attcagagtt   420
taggacggca atcaatcaag atggtgaatt ggggatatat gatgagatga taccaagcta   480
tacaatattt cacaatgata ctgaaacatt ttccagcctt tggactgagt gtaagtctga   540 cttttaaatca tttttagcag attatgaaag tgatacgcaa cggtatggaa acaatcatag   600
aatggaagga aagccaaatg ctccggaaaa catttttaat gtatctatga taccgtggtc   660
aaccttcgat ggctttaatc tgaatttgca gaaaggatat gattatttga ttcctatttt   720
tactatgggg aaatattata agaagataa caaaattata cttcctttgg caattcaagt   780
tcatcacgca gtatgtgacg gatttcacat ttgccgtttt gtaaacgaat tgcaggaatt   840
gataaatagt taaacgcgtc catggagatc tcgaggcctg cagacatgca agcttggcac   900
tggccgtcgt tttacaacgt cgtgactggg aaaaccctgg cgttacccaa cttaatcgcc   960
ttgcagcaca tcccccttttc gccagctggc gtaatagcga agaggcccgc accgatcgcc  1020
cttcccaaca gttgcgcagc ctgaatggcg aatggcgcta gcataaaaat aagaagcctg  1080
catttgcagg cttcttattt ttatggcgcg ccgttctgaa tccttagcta atggttcaac  1140
aggtaactat gacgaagata gcaccctgga taagtctgta atggattcta aggcattaa   1200 tgaagacgtg tatataaaat gtgctaatga aaagaaaat gcgttaaaag agcctaaaat  1260
gagttcaaat ggttttgaaa ttgattggta gtttaattta atatattttt tctattggct  1320
atctcgatac ctatagaatc ttctgttcac ttttgttttt gaaatataaa aaggggcttt  1380 ttagccccctt ttttttaaaa ctccggagga gtttcttcat tcttgatact atacgtaact  1440
attttcgatt tgacttcatt gtcaattaag ctagtaaaat caatggttaa aaaacaaaaa  1500
acttgcattt ttctacctag taatttataa tttaagtgt cgagtttaaa agtataattt  1560
accaggaaag gagcaagttt tttaataagg aaaaattttt cctttaaaa ttctatttcg  1620 ttatatgact aattataatc aaaaaaatga aaataaacaa gaggtaaaaa ctgctttaga  1680
gaaatgtact gataaaaaa gaaaaaatcc tagatttacg tcatacatag caccctttaac  1740 tactaagaaa aatattgaaa ggacttccac ttgtggagat tatttgttta tgttgagtga  1800
tgcagactta gaacatttta aattacataa aggtaatttt tgcggtaata gattttgtcc  1860
aatgtgtagt tggcgacttg cttgtaagga tagtttagaa atatctattc ttatggagca  1920
tttaagaaaa gaagaaaata aagagtttat attttttaact cttacaactc caaatgtaaa  1980
```

```
aagttatgat cttaattatt ctattaaaca atataataaa tcttttaaaa aattaatgga    2040
gcgtaaggaa gttaaggata taactaaagg ttatataaga aaattagaag taacttacca    2100
aaaggaaaaa tacataacaa aggatttatg gaaaataaaa aaagattatt atcaaaaaaa    2160
aggacttgaa attggtgatt tagaacctaa ttttgatact tataatcctc attttcatgt    2220
agttattgca gttaataaaa gttattttac agataaaaat tattatataa atcgagaaag    2280
atggttggaa ttatggaagt ttgctactaa ggatgattct ataactcaag ttgatgttag    2340
aaaagcaaaa attaatgatt ataagaggt ttacgaactt gcgaaatatt cagctaaaga    2400
cactgattat ttaatatcga ggccagtatt tgaaattttt tataaagcat aaaaggcaa    2460 gcaggtatta gttttagtg gattttttaa agatgcacac aaattgtaca agcaaggaaa    2520
acttgatgtt tataaaaaga aagatgaaat taaatatgtc tatatagttt attataattg    2580
gtgcaaaaaa caatatgaaa aaactagaat aagggaactt acggaagatg aaaaagaaga    2640
attaaatcaa gatttaatag atgaaataga aatagattaa agtgtaacta tactttatat    2700
atatatgatt aaaaaaataa aaaacaacag cctattaggt tgttgttttt tattttcttt    2760
attaattttt ttaattttta gttttagtt ctttttttaaa ataagtttca gcctcttttt    2820
caatattttt taaagaagga gtatttgcat gaattgcctt ttttctaaca gacttaggaa    2880
atattttaac agtatcttct tgcgccggtg attttggaac ttcataactt actaatttat    2940
aattattatt ttcttttta attgtaacag ttgcaaaaga agctgaacct gttccttcaa    3000
ctagtttatc atcttcaata taatattctt gacctatata gtataaatat attttattta    3060 tattttact ttttctgaa tctattattt tataatcata aaaagtttta ccaccaaaag    3120
aaggttgtac tccttctggt ccaacatatt ttttactat attatctaaa taattttgg    3180 gaactggtgt tgtaatttga ttaatcgaac aaccagttat acttaaagga attataacta    3240
taaaaatata taggattatc tttttaaatt tcattattgg cctccttttt attaaattta    3300
tgttaccata aaaaggacat aacgggaata tgtagaatat ttttaatgta gacaaaattt    3360
tacataaata taaagaaagg aagtgttttgt ttaaattta tagcaaacta tcaaaaatta    3420
gggggataaa aatttatgaa aaaaggttt tcgatgttat tttatgttt aactttaata    3480 gtttgtggtt tatttacaaa ttcggccggc cgaagcaaac ttaagagtgt gttgatagtg    3540
cagtatctta aaattttgta taataggaat tgaagttaaa ttagatgcta aaaatttgta    3600
attaagaagg agtgattaca tgaacaaaaa tataaaatat tctcaaaact ttttaacgag    3660
tgaaaaagta ctcaaccaaa taataaaaca attgaattta aaagaaaccg ataccgttta    3720
cgaaattgga acaggtaaag ggcatttaac gacgaaactg gctaaaataa gtaaacaggt    3780
aacgtctatt gaattagaca gtcatctatt caacttatcg tcagaaaaat taaaactgaa    3840
tactcgtgtc actttaattc accaagatat tctacagttt caattcccta caaacagag    3900 gtataaaatt gttgggagta ttccttacca tttaagcaca caaattatta aaaagtgg    3960 ttttgaaagc catgcgtctg acatctatct gattgttgaa gaaggattct acaagcgtac    4020
cttggatatt caccgaacac tagggttgct cttgcacact caagtctcga ttcagcaatt    4080
gcttaagctg ccagcggaat gctttcatcc taaaccaaaa gtaaacagtg tcttaataaa    4140
acttacccgc cataccacag atgttccaga taaatattgg aagctatata cgtactttgt    4200
ttcaaaatgg gtcaatcgag aatatcgtca actgttact aaaaatcagt ttcatcaagc    4260
aatgaaacac gccaaagtaa acaatttaag taccgttact tatgagcaag tattgtctat    4320
```

| | | | | | |
|---|---|---|---|---|---|
| ttttaatagt | tatctattat | ttaacgggag | gaaataattc | tatgagtcgc | ttttgtaaat | 4380 |
| ttggaaagtt | acacgttact | aaagggaatg | tgtttaaact | ccttttttgat | aatctcatga | 4440 |
| ccaaaatccc | ttaacgtgag | ttttcgttcc | actgagcgtc | agaccccgta | gaaaagatca | 4500 |
| aaggatcttc | ttgagatcct | ttttttctgc | gcgtaatctg | ctgcttgcaa | acaaaaaaac | 4560 |
| caccgctacc | agcggtggtt | tgtttgccgg | atcaagagct | accaactctt | tttccgaagg | 4620 |
| taactggctt | cagcagagcg | cagataccaa | atactgttct | tctagtgtag | ccgtagttag | 4680 |
| gccaccactt | caagaactct | gtagcaccgc | ctacatacct | cgctctgcta | atcctgttac | 4740 |
| cagtggctgc | tgccagtggc | gataagtcgt | gtcttaccgg | gttggactca | agacgatagt | 4800 |
| taccggataa | ggcgcagcgg | tcgggctgaa | cggggggttc | gtgcacacag | cccagcttgg | 4860 |
| agcgaacgac | ctacaccgaa | ctgagatacc | tacagcgtga | gctatgagaa | agcgccacgc | 4920 |
| ttcccgaagg | gagaaaggcg | gacaggtatc | cggtaagcgg | cagggtcgga | acaggagagc | 4980 |
| gcacgaggga | gcttccaggg | ggaaacgcct | ggtatcttta | tagtcctgtc | gggtttcgcc | 5040 |
| acctctgact | tgagcgtcga | tttttgtgat | gctcgtcagg | ggggcggagc | ctatggaaaa | 5100 |
| acgccagcaa | cgcggccttt | ttacggttcc | tggccttttg | ctggccttttt | gctcacatgt | 5160 |
| tctttcctgc | gttatcccct | gattctgtgg | ataaccgtat | taccgccttt | gagtgagctg | 5220 |
| ataccgctcg | ccgcagccga | acgaccgagc | gcagcgagtc | agtgagcgag | gaagcggaag | 5280 |
| agcgcccaat | acgcagggcc | ccctgcttcg | gggtcattat | agcgattttt | tcggtatatc | 5340 |
| catccttttt | cgcacgatat | acaggatttt | gccaagggt | tcgtgtagac | tttccttggt | 5400 |
| gtatccaacg | gcgtcagccg | ggcaggatag | gtgaagtagg | cccacccgcg | agcgggtgtt | 5460 |
| ccttcttcac | tgtcccttat | tcgcacctgg | cggtgctcaa | cgggaatcct | gctctgcgag | 5520 |
| gctggccggc | taccgccggc | gtaacagatg | agggcaagcg | gatggctgat | gaaaccaagc | 5580 |
| caaccaggaa | gggcagccca | cctatcaagg | tgtactgcct | tccagacgaa | cgaagagcga | 5640 |
| ttgaggaaaa | ggcggcggcg | gccggcatga | gcctgtcggc | ctacctgctg | gccgtcggcc | 5700 |
| agggctacaa | aatcacgggc | gtcgtggact | atgagcacgt | ccgcgagctg | gcccgcatca | 5760 |
| atggcgacct | gggccgcctg | gcggcctgc | tgaaactctg | gctcaccgac | gacccgcgca | 5820 |
| cggcgcggtt | cggtgatgcc | acgatcctcg | ccctgctggc | gaagatcgaa | gagaagcagg | 5880 |
| acgagcttgg | caaggtcatg | atgggcgtgg | tccgccgag | ggcagagcca | tgactttttt | 5940 |
| agccgctaaa | acggccgggg | ggtgcgcgtg | attgccaagc | acgtccccat | gcgctccatc | 6000 |
| aagaagagcg | acttcgcgga | gctggtgaag | tacatcaccg | acgagcaagg | caagaccgat | 6060 |
| cgggcccct | gcaggataaa | aaaattgtag | ataaattta | taaaatagtt | ttatctacaa | 6120 |
| ttttttttatc | aggaaacagc | tatgaccgcg | gccgcggcgc | caagcttaga | aaaatataaa | 6180 |
| taagaagtag | ctttaagaga | attaaattat | taagaaaagc | aaaggtgttt | aaaaaataaa | 6240 |
| tttttaaaca | cctttgctttt | tcttaaatta | taaataagat | aaaaaagaat | cctgaataaa | 6300 |
| ataaaaaggg | gtgtctcaaa | attttatttt | gagacgaccc | cttttttattc | tatatgtcga | 6360 |
| tgctatagct | gagatcgtgg | aattcttgtt | agctaccaga | ttcacattta | agttgtttct | 6420 |
| ctaaaccaca | gattatcaat | tcaagtccaa | aaagaaatgc | tggttctgcg | ccttgatgat | 6480 |
| caaataactc | tattgcttgt | cttaacaatg | gaggcattga | atctgttgtt | ggtgtttctc | 6540 |
| tttcctctttt | tgcaacttga | tgttcttgat | cctccaatac | gcaacctaaa | gtaaaatgtc | 6600 |
| ctacagcact | tagtgcgtat | aaggcatttt | ctaaactaaa | accctgttga | cataagaatg | 6660 |
| ctaattgatt | ttctaatgtt | tcatattgtt | tttcagttgg | tctagttcct | aaatgtactt | 6720 |

```
tagccccatc tctatgtgat aatagagcac aacgaaaaga tttagcgtta ttcctaagaa      6780
aatcttgcca tgattcacct tctaaaggac aaaagtgagt gtgatgtcta tctaacattt      6840
caatagctaa ggcgtcaagt aaagctctct tattcttcac atgccaatac aacgtaggtt      6900
gttctactcc aagtttctga gctaactttc ttgtagttag tccttctatt ccaacttcat      6960
ttagtaattc caatgcacta ttgataactt tacttttatc aagtctagac atcatttaat      7020
atcctcctct tcaatatatt taagtcgact gatcggatcc aatttatacg ttttctctaa      7080
caacttaatt atacccacta ttattatttt tatcaatata gagctcccat ggcggccggt      7140
cgatatcgat gtgtagtagc ctgtgaaat                                        7169

<210> SEQ ID NO 25
<211> LENGTH: 5770
<212> TYPE: DNA
<213> ORGANISM: Artificial Sequence
<220> FEATURE:
<223> OTHER INFORMATION: pMTL-YZ010

<400> SEQUENCE: 25
cctgcaggat aaaaaaattg tagataaatt ttataaaata gttttatcta caatttttt         60 atcaggaaac agctatgacc gcggccgcgg cgccaagctt agaaaatat aaataagaag        120 tagctttaag agaattaaat tattaagaaa agcaaaggtg tttaaaaaat aaattttaa        180 acacctttgc ttttcttaaa ttataaataa gataaaaaag aatcctgaat aaaataaaaa       240
ggggtgtctc aaaattttat tttgagacga ccccttttta ttctatatgt cgatgctata       300
gctgagatcg tggaattctt gttagctacc agattcacat ttaagttgtt tctctaaacc      360
acagattatc aattcaagtc caaaagaaa tgctggttct gcgccttgat gatcaaataa       420
ctctattgct tgtcttaaca atggaggcat tgaatctgtt gttggtgttt ctcttcctc       480 ttttgcaact tgatgttctt gatcctccaa tacgcaacct aaagtaaaat gtcctacagc      540
acttagtgcg tataaggcat tttctaaact aaaaccctgt tgacataaga atgctaattg      600
attttctaat gtttcatatt gttttttcagt tggtctagtt cctaaatgta cttagcccc      660 atctctatgt gataatagag cacaacgaaa agatttagcg ttattcctaa gaaaatcttg      720
ccatgattca ccttctaaag gacaaaagtg agtgtgatgt ctatctaaca tttcaatagc      780
taaggcgtca gtaaagctc tcttattctt cacatgccaa tacaacgtag gttgttctac      840
tccaagtttc tgagctaact ttcttgtagt tagtccttct attccaactt catttagtaa      900
ttccaatgca ctattgataa ctttactttt atcaagtcta gacatcattt aatatcctcc      960
tcttcaatat atttaagtcg actgatcgga tccaatttat acgttttctc taacaactta     1020
attatacccc ctattattat ttttatcaat atagagctcc catggcggcc ggtcgatatc     1080
gatgtgtagt agcctgtgaa ataagtaagg aaaaaaaaga agtaagtgtt atatatgatg     1140
attattttgt agatgtagat aggataatag aatccataga aaatataggt tatacagtta     1200
tataaaaatt actttaaaat ctatcattga tagggtaaaa tataaatcgt ataaagttgt     1260
gtaattttta aggaggtgtg ttacagacgt ccgcgagaga ccttaaatat attgaagagg     1320
aggaaataca tatgaccatg attacgaatt cgagctcggt acccggggat cagcttggca     1380
ctggccgtcg ttttacaacg tcgtgactgg gaaaaccctg gcgttaccca acttaatcgc     1440
cttgcagcac atccccctt cgccagctgg cgtaatagcg aagaggcccg caccgatcgc     1500
ccttcccaac agttgcgcag cctgaatggc gaatggcgct agcataaaaa taagaagcct     1560
```

```
gcatttgcag gcttcttatt tttatggcgc gccgccatta ttttttttgaa caattgacaa    1620 ttcatttctt attttttatt aagtgatagt caaaaggcat aacagtgctg aatagaaaga    1680
aatttacaga aaagaaaatt atagaattta gtatgattaa ttatactcat ttatgaatgt    1740
ttaattgaat acaaaaaaaa atacttgtta tgtattcaat tacgggttaa aatatagaca    1800
agttgaaaaa tttaataaaa aataagtcc tcagctctta tatattaagc taccaactta    1860
gtatataagc caaaacttaa atgtgctacc aacacatcaa gccgttagag aactctatct    1920
atagcaatat ttcaaatgta ccgacataca agagaaacat taactatata tattcaattt    1980
atgagattat cttaacagat ataaatgtaa attgcaataa gtaagattta gaagtttata    2040
gcctttgtgt attggaagca gtacgcaaag ctttttttat ttgataaaaa ttagaagtat    2100
atttattttt tcataattaa tttatgaaaa tgaaggggg tgagcaaagt gacagaggaa    2160
agcagtatct tatcaaataa caaggtatta gcaatatcat tattgacttt agcagtaaac    2220
attatgactt ttatagtgct tgtagctaag tagtacgaaa gggggagctt taaaaagctc    2280
cttggaatac atagaattca taaattaatt tatgaaaaga agggcgtata tgaaaacttg    2340
taaaaattgc aaagagttta ttaaagatac tgaaatatgc aaaatacatt cgttgatgat    2400
tcatgataaa acagtagcaa cctattgcag taaatacaat gagtcaagat gtttacataa    2460
agggaaagtc caatgtatta attgttcaaa gatgaaccga tatggatggt gtgccataaa    2520
aatgagatgt tttacagagg aagaacagaa aaagaacgt acatgcatta aatattatgc    2580
aaggagcttt aaaaaagctc atgtaaagaa gagtaaaaag aaaaaataat ttatttatta    2640
atttaatatt gagagtgccg acacagtatg cactaaaaaa tatatctgtg gtgtagtgag    2700
ccgatacaaa aggatagtca ctcgcatttt cataatacat cttatgttat gattatgtgt    2760
cggtgggact tcacgacgaa aacccacaat aaaaaaagag ttcggggtag ggttaagcat    2820
agttgaggca actaaacaat caagctagga tatgcagtag cagaccgtaa ggtcgttgtt    2880
taggtgtgtt gtaatacata cgctattaag atgtaaaaat acggatacca atgaagggaa    2940
aagtataatt tttggatgta gtttgtttgt tcatctatgg gcaaactacg tccaaagccg    3000
tttccaaatc tgctaaaaag tatatccttt ctaaaatcaa agtcaagtat gaaatcataa    3060
ataaagttta attttgaagt tattatgata ttatgttttt ctattaaaat aaattaagta    3120
tatagaatag tttaataata gtatatactt aatgtgataa gtgtctgaca gtgtcacaga    3180
aaggatgatt gttatggatt ataagcggcc ggccgaagca aacttaagag tgtgttgata    3240
gtgcagtatc ttaaaatttt gtataatagg aattgaagtt aaattagatg ctaaaaattt    3300
gtaattaaga aggagtgatt acatgaacaa aaatataaaa tattctcaaa acttttttaac    3360 gagtgaaaaa gtactcaacc aaataataaa acaattgaat ttaaaagaaa ccgataccgt    3420
ttacgaaatt ggaacaggta aagggcattt aacgacgaaa ctggctaaaa taagtaaaca    3480
ggtaacgtct attgaattag acagtcatct attcaactta tcgtcagaaa aattaaaact    3540
gaatactcgt gtcacttttaa ttcaccaaga tattctacag tttcaattcc ctaacaaaca    3600
gaggtataaa attgttggga gtattcctta ccatttaagc acacaaatta ttaaaaaagt    3660 ggttttgaa agccatgcgt ctgacatcta tctgattgtt gaagaaggat tctacaagcg    3720
taccttggat attcaccgaa cactagggtt gctcttgcac actcaagtct cgattcagca    3780
attgcttaag ctgccagcgg aatgctttca tcctaaacca aaagtaaaca gtgtcttaat    3840 aaacttacc cgccatacca cagatgttcc agataaatat tggaagctat atacgtactt    3900
tgtttcaaaa tgggtcaatc gagaatatcg tcaactgttt actaaaaatc agtttcatca    3960
```

```
agcaatgaaa cacgccaaag taaacaattt aagtaccgtt acttatgagc aagtattgtc   4020
tatttttaat agttatctat tatttaacgg gaggaaataa ttctatgagt cgcttttgta   4080
aatttggaaa gttacacgtt actaaaggga atgtgtttaa actccttttt gataatctca   4140
tgaccaaaat cccttaacgt gagttttcgt tccactgagc gtcagacccc gtagaaaaga   4200
tcaaaggatc ttcttgagat ccttttttc tgcgcgtaat ctgctgcttg caaacaaaaa    4260
aaccaccgct accagcggtg gtttgtttgc cggatcaaga gctaccaact cttttccga    4320 aggtaactgg cttcagcaga gcgcagatac caaatactgt tcttctagtg tagccgtagt   4380
taggccacca cttcaagaac tctgtagcac cgcctacata cctcgctctg ctaatcctgt   4440
taccagtggc tgctgccagt ggcgataagt cgtgtcttac cgggttggac tcaagacgat   4500
agttaccgga taaggcgcag cggtcgggct gaacgggggg ttcgtgcaca cagcccagct   4560
tggagcgaac gacctacacc gaactgagat acctacagcg tgagctatga gaaagcgcca   4620
cgcttcccga aggagaaag gcggacaggt atccggtaag cggcagggtc ggaacaggag    4680
agcgcacgag ggagcttcca ggggaaacg cctggtatct ttatagtcct gtcgggtttc    4740
gccacctctg acttgagcgt cgatttttgt gatgctcgtc aggggggcgg agcctatgga   4800
aaaacgccag caacgcggcc tttttacggt tcctggcctt ttgctggcct tttgctcaca   4860
tgttctttcc tgcgttatcc cctgattctg tggataaccg tattaccgcc tttgagtgag   4920
ctgataccgc tcgccgcagc cgaacgaccg agcgcagcga gtcagtgagc gaggaagcgg   4980
aagagcgccc aatacgcagg gccccctgct tcgggtcat tatagcgatt ttttcggtat    5040
atccatcctt tttcgcacga tatacaggat tttgccaaag ggttcgtgta acttttcctt   5100
ggtgtatcca acggcgtcag ccgggcagga taggtgaagt aggcccaccc gcgagcgggt   5160
gttccttctt cactgtccct tattcgcacc tggcggtgct caacgggaat cctgctctgc   5220
gaggctggcc ggctaccgcc ggcgtaacag atgagggcaa gcggatggct gatgaaacca   5280
agccaaccag gaagggcagc ccacctatca aggtgtactg ccttcagac gaacgaagag    5340 cgattgagga aaaggcggcg gcggccggca tgagcctgtc ggcctacctg ctggccgtcg   5400
gccagggcta caaaatcacg ggcgtcgtgg actatgagca cgtccgcgag ctggcccgca   5460
tcaatggcga cctgggccgc ctgggcggcc tgctgaaact ctggctcacc gacgacccgc   5520
gcacggcgcg gttcggtgat ccacgatcc tcgccctgct ggcgaagatc gaagagaagc    5580
aggacgagct tggcaaggtc atgatgggcg tggtccgccc gagggcagag ccatgacttt   5640
tttagccgct aaaacggccg gggggtgcgc gtgattgcca agcacgtccc catgcgctcc   5700
atcaagaaga gcgacttcgc ggagctggtg aagtacatca ccgacgagca aggcaagacc   5760
gatcgggccc                                                          5770
```

<210> SEQ ID NO 26
<211> LENGTH: 5553
<212> TYPE: DNA
<213> ORGANISM: Artificial Sequence
<220> FEATURE:
<223> OTHER INFORMATION: pMTL-YZ011

<400> SEQUENCE: 26

```
cctgcaggat aaaaaaattg tagataaatt ttataaaata gttttatcta caatttttt     60 atcaggaaac agctatgacc gcgccgcggc gccaagctta gaaaaatata aataagaagt   120
agctttaaga gaattaaatt attaagaaaa gcaaggtgt ttaaaaaata aattttaaa    180
```

```
caccttttgct tttcttaaat tataaataag ataaaaaaga atcctgaata aaataaaaag      240
gggtgtctca aaattttatt ttgagacgac ccctttttat tctatatgtc gatgctatag      300
ctgagatcgt ggaattcttg ttagctacca gattcacatt taagttgttt ctctaaacca      360
cagattatca attcaagtcc aaaaagaaat gctggttctg cgccttgatg atcaaataac      420
tctattgctt gtcttaacaa tggaggcatt gaatctgttg ttggtgtttc tctttcctct      480
tttgcaactt gatgttcttg atcctccaat acgcaaccta aagtaaaatg tcctacagca      540
cttagtgcgt ataaggcatt ttctaaacta aaaccctgtt gacataagaa tgctaattga      600
ttttctaatg tttcatattg tttttcagtt ggtctagttc ctaaatgtac tttagcccca      660
tctctatgtg ataatagagc acaacgaaaa gatttagcgt tattcctaag aaaatcttgc      720
catgattcac cttctaaagg acaaaagtga gtgtgatgtc tatctaacat ttcaatagct      780
aaggcgtcaa gtaaagctct cttattcttc acatgccaat acaacgtagg ttgttctact      840 ccaagttttct gagctaactt tcttgtagtt agtccttcta ttccaacttc atttagtaat      900
tccaatgcac tattgataac tttactttta tcaagtctag acatcattta atatcctcct      960
cttcaatata tttaagtcga ctgatcggat ccaatttata cgttttctct aacaacttaa     1020
ttatacccac tattattatt tttatcaata tagagctccc atggcggccg gtcgatatcg     1080
atgtgtagta gcctgtgaaa taagtaagga aaaaaagaa gtaagtgtta tatatgatga     1140
ttattttgta gatgtagata ggataataga atccatagaa aatataggtt atacagttat     1200
ataaaaatta ctttaaaatc tatcattgat agggtaaaat ataaatcgta taaagttgtg     1260 taattttttaa ggaggtgtgt tacagacgtc cgcgagagac cttaaatata ttgaagagga     1320
ggaaatacat atgaccatga ttacgaattc gagctcggta cccggggatc cgcgccgcca     1380
ttattttttt gaacaattga caattcattt cttatttttt attaagtgat agtcaaaagg     1440
cataacagtg ctgaatagaa agaaatttac agaaaagaaa attatagaat ttagtatgat     1500
taattatact catttatgaa tgtttaattg aatacaaaaa aaaatacttg ttatgtattc     1560
aattacgggt taaatatag acaagttgaa aaatttaata aaaaaataag tcctcagctc     1620
ttatatatta agctaccaac ttagtatata agccaaaact taaatgtgct accaacacat     1680
caagccgtta gagaactcta tctatagcaa tatttcaaat gtaccgacat acaagagaaa     1740
cattaactat atatattcaa tttatgagat tatcttaaca gatataaatg taaattgcaa     1800
taagtaagat ttagaagttt atagccttttg tgtattggaa gcagtacgca aaggctttttt     1860 tatttgataa aaattagaag tatattttatt ttttcataat taatttatga aaatgaaagg     1920
gggtgagcaa agtgacagag gaaagcagta tcttatcaaa taacaaggta ttagcaatat     1980
cattattgac tttagcagta acattatga cttttatagt gcttgtagct aagtagtacg     2040
aaggggggag ctttaaaaag ctccttggaa tacatagaat tcataaatta atttatgaaa     2100
agaagggcgt atatgaaaac ttgtaaaaat gcaaagagt ttattaaaga tactgaaata     2160
tgcaaaatac attcgttgat gattcatgat aaaacagtag caacctattg cagtaaatac     2220
aatgagtcaa gatgtttaca taaagggaaa gtccaatgta ttaattgttc aaagatgaac     2280
cgatatggat ggtgtgccat aaaaatgaga tgttttacag aggaagaaca gaaaaaagaa     2340
cgtacatgca ttaaatatta tgcaaggagc tttaaaaaag ctcatgtaaa gaagagtaaa     2400
aagaaaaaat aatttattta ttaatttaat attgagagtg ccgacacagt atgcactaaa     2460
aaatatatct gtggtgtagt gagccgatac aaaaggatag tcactcgcat tttcataata     2520
catcttatgt tatgattatg tgtcggtggg acttcacgac gaaaacccac aataaaaaaa     2580
```

```
gagttcgggg tagggttaag catagttgag gcaactaaac aatcaagcta ggatatgcag    2640
tagcagaccg taaggtcgtt gtttaggtgt gttgtaatac atacgctatt aagatgtaaa    2700
aatacggata ccaatgaagg gaaaagtata attttttggat gtagtttgtt tgttcatcta   2760
tgggcaaact acgtccaaag ccgttttccaa atctgctaaa aagtatatcc tttctaaaat   2820
caaagtcaag tatgaaatca taaataaagt ttaattttga agttattatg atattatgtt   2880
tttctattaa aataaattaa gtatatagaa tagtttaata atagtatata cttaatgtga    2940
taagtgtctg acagtgtcac agaaaggatg attgttatgg attataagcg gccggccgaa    3000
gcaaacttaa gagtgtgttg atagtgcagt atcttaaaat tttgtataat aggaattgaa    3060
gttaaattag atgctaaaaa tttgtaatta agaaggagtg attacatgaa caaaaatata    3120
aaatattctc aaaactttt aacgagtgaa aaagtactca accaaataat aaaacaattg    3180
aatttaaaag aaaccgatac cgtttacgaa attggaacag gtaaagggca tttaacgacg    3240
aaactggcta aaataagtaa acaggtaacg tctattgaat tagacagtca tctattcaac    3300
ttatcgtcag aaaaattaaa actgaatact cgtgtcactt taattcacca agatattcta    3360
cagtttcaat tccctaacaa acagaggtat aaaattgttg ggagtattcc ttaccattta    3420
agcacacaaa ttattaaaaa agtggttttt gaaagccatg cgtctgacat ctatctgatt    3480
gttgaagaag gattctacaa gcgtaccttg gatattcacc gaaacactagg gttgctcttg   3540 cacactcaag tctcgattca gcaattgctt aagctgccag cggaatgctt tcatcctaaa    3600
ccaaaagtaa acagtgtctt aataaaactt acccgccata ccacagatgt tccagataaa    3660
tattggaagc tatatacgta ctttgtttca aaatgggtca atcgagaata tcgtcaactg    3720
tttactaaaa atcagtttca tcaagcaatg aaacacgcca agtaaacaa tttaagtacc     3780 gttacttatg agcaagtatt gtctattttt aatagttatc tattatttaa cgggaggaaa    3840
taattctatg agtcgctttt gtaaatttgg aaagttacac gttactaaag ggaatgtgtt    3900
taaactcctt tttgataatc tcatgaccaa aatcccttaa cgtgagtttt cgttccactg    3960
agcgtcagac cccgtagaaa agatcaaagg atcttcttga atccttttt ttctgcgcgt     4020 aatctgctgc ttgcaaacaa aaaaaccacc gctaccagcg gtggtttgtt tgccggatca    4080
agagctacca actctttttc cgaaggtaac tggcttcagc agagcgcaga taccaaatac    4140
tgttcttcta gtgtagccgt agttaggcca ccacttcaag aactctgtag caccgcctac    4200
atacctcgct ctgctaatcc tgttaccagt ggctgctgcc agtggcgata agtcgtgtct    4260
taccgggttg gactcaagac gatagttacc ggataaggcg cagcggtcgg gctgaacggg    4320
gggttcgtgc acacagccca gcttggagcg aacgacctac accgaactga gatacctaca    4380
gcgtgagcta tgagaaagcg ccacgcttcc gaagggaga aaggcggaca ggtatccggt     4440
aagcggcagg gtcggaacag gagagcgcac gagggagctt ccaggggaa acgcctggta     4500 tctttatagt cctgtcgggt ttcgccacct ctgacttgag cgtcgatttt tgtgatgctc    4560
gtcagggggg cggagcctat ggaaaaacgc cagcaacgcg gcctttttac ggttcctggc    4620
cttttgctgg ccttttgctc acatgttctt tcctgcgtta tcccctgatt ctgtggataa    4680
ccgtattacc gcctttgagt gagctgatac cgctcgccgc agccgaacga ccgagcgcag    4740
cgagtcagtg agcgaggaag cggaagagcg cccaatacgc agggccccct gcttcgggt    4800 cattatagcg attttttcgg tatatccatc ctttttcgca cgatatacag gattttgcca    4860
aagggttcgt gtagactttc cttggtgtat ccaacggcgt cagccgggca ggataggtga    4920
```

| | |
|---|---|
| agtaggccca cccgcgagcg ggtgttcctt cttcactgtc ccttattcgc acctggcggt | 4980 |
| gctcaacggg aatcctgctc tgcgaggctg ccggctacc gccggcgtaa cagatgaggg | 5040 |
| caagcggatg gctgatgaaa ccaagccaac caggaagggc agcccaccta tcaaggtgta | 5100 |
| ctgccttcca gacgaacgaa gagcgattga ggaaaaggcg gcggcggccg gcatgagcct | 5160 |
| gtcggcctac ctgctggccg tcggccaggg ctacaaaatc acgggcgtcg tggactatga | 5220 |
| gcacgtccgc gagctggccc gcatcaatgg cgacctgggc cgcctgggcg gcctgctgaa | 5280 |
| actctggctc accgacgacc cgcgcacggc gcggttcggt gatgccacga tcctcgccct | 5340 |
| gctggcgaag atcgaagaga agcaggacga gcttggcaag gtcatgatgg gcgtggtccg | 5400 |
| cccgagggca gagccatgac tttttagcc gctaaaacgg ccggggggtg cgcgtgattg | 5460 |
| ccaagcacgt ccccatgcgc tccatcaaga gagcgactt cgcggagctg gtgaagtaca | 5520 |
| tcaccgacga gcaaggcaag accgatcggg ccc | 5553 |

<210> SEQ ID NO 27
<211> LENGTH: 6182
<212> TYPE: DNA
<213> ORGANISM: Artificial Sequence
<220> FEATURE:
<223> OTHER INFORMATION: pMTL-YZ012

<400> SEQUENCE: 27

| | |
|---|---|
| cctgcaggat aaaaaaattg tagataaatt ttataaaata gttttatcta caattttttt | 60 |
| atcaggaaac agctatgacc ggcgcgccgc tcactgcccg ctttccagtc gggaaacctg | 120 |
| tcgtgccagc tgcattaatg aatcggccaa cgcgcgggga gaggcggttt gcgtattggg | 180 |
| cgccagggtg gtttttcttt tcaccagtga gacgggcaac agctgattgc ccttcaccgc | 240 |
| ctggccctga gagagttgca gcaagcggtc cacgctggtt tgccccagca ggcgaaaatc | 300 |
| ctgtttgatg gtggttaacg gcgggatata acatgagctg tcttcggtat cgtcgtatcc | 360 |
| cactaccgag atatccgcac caacgcgcag cccggactcg gtaatggcgc gcattgcgcc | 420 |
| cagcgccatc tgatcgttgg caaccagcat cgcagtggga acgatgccct cattcagcat | 480 |
| ttgcatggtt tgttgaaaac cggacatggc actccagtcg ccttcccgtt ccgctatcgg | 540 |
| ctgaatttga ttgcgagtga gatatttatg ccagccagcc agacgcagac gcgccgagac | 600 |
| agaacttaat gggcccgcta acagcgcgat ttgctggtga cccaatgcga ccagatgctc | 660 |
| cacgcccagt cgcgtaccgt cttcatggga gaaaataata ctgttgatgg gtgtctggtc | 720 |
| agagacatca agaaataacg ccggaacatt agtgcaggca gcttccacag caatggcatc | 780 |
| ctggtcatcc agcggatagt taatgatcag cccactgacg cgttgcgcga agattgtg | 840 |
| caccgccgyt ttacaggctt cgacgccgct tcgttctacc atcgacacca ccacgctggc | 900 |
| acccagttga tcggcgcgag atttaatcgc cgcgacaatt tgcgacggcg cgtgcagggc | 960 |
| cagactggag gtggcaacgc caatcagcaa cgactgtttg cccgccagtt gttgtgccac | 1020 |
| gcggttggga atgtaattca gctccgccat cgccgcttcc acttttttcc cgcgttttcgc | 1080 |
| agaaacgtgg ctggcctggt tcaccacgcg ggaaacggtc tgataagaga caccggcata | 1140 |
| ctctgcgaca tcgtataacg ttactggttt catatgttgc acctctactt taataatttt | 1200 |
| taacttttat atatgattaa tttaattgtt tgttaaattt atatcaatca atgctatgaa | 1260 |
| tatttcttta taccttattg taacaaaaaa atattggaaa tgttgaattt tcagaatatt | 1320 |
| attttttatta tattattaat tttatatatt cattttttata agatttcaca acacgaacgt | 1380 |
| aatataatat atcttcctca tcttctgaaa agattatact aattctattc atgttactta | 1440 |

```
taatcttatt ttggtaaatc gaattttTca attatatgtt cggcaacctt tatcccatca    1500
acagccgctg atattatacc acctgcaaat cctgcccctt ctccagttgg ataaagtccg    1560
catacattta tactttcaag tgaagcattt ctattcaatc taactggtgc tgatgttctt    1620
gtctcaattc ccgttaaaat tgcatcttct cttgcatacc cttttatctt tttatcaaaa    1680
tttataattc cttctttaag agcctctaca acataatcag gtaaacattc ttttaattcc    1740
ctgaattatc tgcagagaat tccccggatc gagatagtat atgatgcata ttctttaaat    1800
atagataaag ttatagaagc aatagaagat ttaggattta ctgtaatata aattacactt    1860
ttaaaaagtt taaaaacatg atacaataag ttatggttgg aattgttatc cgctcacaat    1920
tccaacttat gattaaaatt ttaaggaggt gtatttcata tgaccatgat tacgaattcg    1980
agctcggtac ccggggatcc gcgccgccat tatttttttg aacaattgac aattcatttc    2040 ttattttta ttaagtgata gtcaaaaggc ataacagtgc tgaatagaaa gaaatttaca    2100
gaaaagaaaa ttatagaatt tagtatgatt aattatactc atttatgaat gtttaattga    2160
atacaaaaaa aaatacttgt tatgtattca attacgggtt aaaatataga caagttgaaa    2220
aatttaataa aaaataagt cctcagctct tatatattaa gctaccaact tagtatataa    2280
gccaaaactt aaatgtgcta ccaacacatc aagccgttag agaactctat ctatagcaat    2340
atttcaaatg taccgacata caagagaaac attaactata tatattcaat ttatgagatt    2400
atcttaacag atataaatgt aaattgcaat aagtaagatt tagaagttta tagcctttgt    2460
gtattggaag cagtacgcaa aggctttttt atttgataaa aattagaagt atatttattt    2520
tttcataatt aatttatgaa atgaaaggg ggtgagcaaa gtgacagagg aaagcagtat    2580
cttatcaaat aacaaggtat tagcaatatc attattgact ttagcagtaa acattatgac    2640
ttttatagtg cttgtagcta agtagtacga aaggggagc tttaaaaagc tccttggaat    2700
acatagaatt cataaattaa tttatgaaaa gaagggcgta tatgaaaact tgtaaaaatt    2760
gcaaagagtt tattaaagat actgaaatat gcaaaataca ttcgttgatg attcatgata    2820
aaacagtagc aacctattgc agtaaataca atgagtcaag atgtttacat aaagggaaag    2880
tccaatgtat taattgttca aagatgaacc gatatggatg gtgtgccata aaaatgagat    2940
gttttacaga ggaagaacag aaaaaagaac gtacatgcat taaatattat gcaaggagct    3000
ttaaaaaagc tcatgtaaag aagagtaaaa agaaaaaata atttatttat taatttaata    3060
ttgagagtgc cgacacagta tgcactaaaa aatatatctg tggtgtagtg agccgataca    3120
aaaggatagt cactcgcatt ttcataatac atcttatgtt atgattatgt gtcggtggga    3180
cttcacgacg aaaacccaca ataaaaaaag agttcggggt agggttaagc atagttgagg    3240
caactaaaca atcaagctag gatatgcagt agcagaccgt aaggtcgttg tttaggtgtg    3300
ttgtaataca tacgctatta agatgtaaaa atacggatac caatgaaggg aaaagtataa    3360
tttttggatg tagtttgttt gttcatctat gggcaaacta cgtccaaagc cgtttccaaa    3420
tctgctaaaa agtatatcct ttctaaaatc aaagtcaagt atgaaatcat aaataaagtt    3480
taattttgaa gttattatga tattatgttt ttctattaaa ataaattaag tatatagaat    3540
agtttaataa tagtatatac ttaatgtgat aagtgtctga cagtgtcaca gaaaggatga    3600
ttgttatgga ttataagcgg ccggccgaag caaacttaag agtgtgttga tagtgcagta    3660
tcttaaaatt ttgtataata ggaattgaag ttaaattaga tgctaaaaat ttgtaattaa    3720
gaaggagtga ttacatgaac aaaaatataa aatattctca aactttttta acgagtgaaa    3780
```

-continued

```
aagtactcaa ccaaataata aaacaattga atttaaaaga aaccgatacc gtttacgaaa    3840
ttggaacagg taaagggcat ttaacgacga aactggctaa aataagtaaa caggtaacgt    3900
ctattgaatt agacagtcat ctattcaact tatcgtcaga aaaattaaaa ctgaatactc    3960
gtgtcacttt aattcaccaa gatattctac agtttcaatt ccctaacaaa cagaggtata    4020
aaattgttgg gagtattcct taccatttaa gcacacaaat tattaaaaaa gtggtttttg    4080
aaagccatgc gtctgacatc tatctgattg ttgaagaagg attctacaag cgtaccttgg    4140
atattcaccg aacactaggg ttgctcttgc acactcaagt ctcgattcag caattgctta    4200
agctgccagc ggaatgcttt catcctaaac caaaagtaaa cagtgtctta ataaaactta    4260
cccgccatac cacagatgtt ccagataaat attggaagct atatacgtac tttgtttcaa    4320
aatgggtcaa tcgagaatat cgtcaactgt ttactaaaaa tcagtttcat caagcaatga    4380
aacacgccaa agtaaacaat ttaagtaccg ttacttatga gcaagtattg tctattttta    4440
atagttatct attatttaac gggaggaaat aattctatga gtcgcttttg taaatttgga    4500
aagttacacg ttactaaagg gaatgtgttt aaactccttt ttgataatct catgaccaaa    4560
atcccttaac gtgagttttc gttccactga gcgtcagacc ccgtagaaaa gatcaaagga    4620
tcttcttgag atccttttttt tctgcgcgta atctgctgct tgcaaacaaa aaaaccaccg    4680
ctaccagcgg tggtttgttt gccggatcaa gagctaccaa ctcttttttcc gaaggtaact    4740
ggcttcagca gagcgcagat accaaatact gttcttctag tgtagccgta gttaggccac    4800
cacttcaaga actctgtagc accgcctaca tacctcgctc tgctaatcct gttaccagtg    4860
gctgctgcca gtggcgataa gtcgtgtctt accgggttgg actcaagacg atagttaccg    4920
gataaggcgc agcggtcggg ctgaacgggg ggttcgtgca cacagcccag cttggagcga    4980
acgacctaca ccgaactgag atacctacag cgtgagctat gagaaagcgc cacgcttccc    5040
gaagggagaa aggcggacag gtatccggta agcggcaggg tcggaacagg agagcgcacg    5100
agggagcttc caggggggaaa cgcctggtat ctttatagtc ctgtcgggtt tcgccacctc    5160
tgacttgagc gtcgattttt gtgatgctcg tcagggggggc ggagcctatg gaaaaacgcc    5220
agcaacgcgg cctttttacg gttcctggcc ttttgctggc cttttgctca catgttcttt    5280
cctgcgttat cccctgattc tgtggataac cgtattaccg cctttgagtg agctgatacc    5340
gctcgccgca gccgaacgac cgagcgcagc gagtcagtga gcgaggaagc ggaagagcgc    5400
ccaatacgca gggccccctg cttcggggtc attatagcga ttttttcggt atatccatcc    5460
tttttcgcac gatatacagg attttgccaa agggttcgtg tagactttcc ttggtgtatc    5520
caacggcgtc agccgggcag gataggtgaa gtaggcccac ccgcgagcgg gtgttccttc    5580
ttcactgtcc cttattcgca cctggcggtg ctcaacggga atcctgctct gcgaggctgg    5640
ccggctaccg ccggcgtaac agatgagggc aagcggatgg ctgatgaaac caagccaacc    5700
aggaagggca gcccacctat caaggtgtac tgccttccag acgaacgaag agcgattgag    5760
gaaaaggcgg cggcggccgg catgagcctg tcggcctacc tgctggccgt cggccagggc    5820
tacaaaatca cgggcgtcgt ggactatgag cacgtccgcg agctggcccg catcaatggc    5880
gacctggggcc gctgggcgg cctgctgaaa ctctggctca ccgacgaccc gcgcacggcg    5940
cggttcggtg atgccacgat cctcgccctg ctggcgaaga tcgaagagaa gcaggacgag    6000
cttggcaagg tcatgatggg cgtggtccgc ccgagggcag agccatgact ttttagccg     6060
ctaaaacggc cggggggtgc gcgtgattgc caagcacgtc cccatgcgct ccatcaagaa    6120
gagcgacttc gcggagctgg tgaagtacat caccgacgag caaggcaaga ccgatcgggc    6180
```

| | |
|---|---|
| cc | 6182 |

<210> SEQ ID NO 28
<211> LENGTH: 34
<212> TYPE: DNA
<213> ORGANISM: Artificial Sequence
<220> FEATURE:
<223> OTHER INFORMATION: Primer NotI/AscI sense

<400> SEQUENCE: 28

| | |
|---|---|
| aacagctatg accggcgcgc cgctcactgc ccgc | 34 |

<210> SEQ ID NO 29
<211> LENGTH: 34
<212> TYPE: DNA
<213> ORGANISM: Artificial Sequence
<220> FEATURE:
<223> OTHER INFORMATION: Primer NotI/AscI antisense

<400> SEQUENCE: 29

| | |
|---|---|
| gcgggcagtg agcggcgcgc cggtcatagc tgtt | 34 |

<210> SEQ ID NO 30
<211> LENGTH: 8554
<212> TYPE: DNA
<213> ORGANISM: Artificial Sequence
<220> FEATURE:
<223> OTHER INFORMATION: pMTL-YZ013

<400> SEQUENCE: 30

| | |
|---|---|
| gcggtcatag ctgtttcctg ataaaaaaat tgtagataaa actatttat aaaatttatc | 60 |
| tacaattttt ttatcctgca ggcagtcggc gcgccgctca ctgcccgctt tccagtcggg | 120 |
| aaacctgtcg tgccagctgc attaatgaat cggccaacgc gcggggagag gcggtttgcg | 180 |
| tattgggcgc cagggtggtt tttcttttca ccagtgagac gggcaacagc tgattgccct | 240 |
| tcaccgcctg gccctgagag agttgcagca agcggtccac gctggtttgc cccagcaggc | 300 |
| gaaaatcctg tttgatggtg gttaacggcg ggatataaca tgagctgtct tcggtatcgt | 360 |
| cgtatcccac taccgagata tccgcaccaa cgcgcagccc ggactcggta atggcgcgca | 420 |
| ttgcgcccag cgccatctga tcgttggcaa ccagcatcgc agtgggaacg atgccctcat | 480 |
| tcagcatttg catggtttgt tgaaaaccgg acatggcact ccagtcgcct tcccgttccg | 540 |
| ctatcggctg aatttgattg cgagtgagat atttatgcca gccagccaga cgcagacgcg | 600 |
| ccgagacaga acttaatggg cccgctaaca gcgcgatttg ctggtgaccc aatgcgacca | 660 |
| gatgctccac gcccagtcgc gtaccgtctt catgggagaa aataatactg ttgatgggtg | 720 |
| tctggtcaga gacatcaaga aataacgccg gaacattagt gcaggcagct tccacagcaa | 780 |
| tggcatcctg gtcatccagc ggatagttaa tgatcagccc actgacgcgt tgcgcgagaa | 840 |
| gattgtgcac cgccgyttta caggcttcga cgccgcttcg ttctaccatc gacaccacca | 900 |
| cgctggcacc cagttgatcg gcgcgagatt taatcgccgc gacaatttgc gacggcgcgt | 960 |
| gcagggccag actggaggtg gcaacgccaa tcagcaacga ctgtttgccc gccagttgtt | 1020 |
| gtgccacgcg gttgggaatg taattcagct ccgccatcgc cgcttccact tttcccgcg | 1080 |
| ttttcgcaga aacgtggctg gcctggttca ccacgcggga aacggtctga taagagacac | 1140 |
| cggcatactc tgcgacatcg tataacgtta ctggtttcat atgttgcacc tctactttaa | 1200 |
| taatttttaa cttttatata tgattaattt aattgtttgt taaatttata tcaatcaatg | 1260 |

```
ctatgaatat ttctttatac cttattgtaa caaaaaaata ttggaaatgt tgaatttca      1320 gaatattatt tttattatat tattaatttt atatattcat ttttataaga tttcacaaca     1380
cgaacgtaat ataatatatc ttcctcatct tctgaaaaga ttatactaat tctattcatg    1440
ttacttataa tcttattttg gtaaatcgaa tttttcaatt atatgttcgg caacctttat    1500
cccatcaaca gccgctgata ttataccacc tgcaaatcct gccccttctc cagttggata    1560
aagtccgcat acatttatac tttcaagtga agcatttcta ttcaatctaa ctggtgctga    1620
tgttcttgtc tcaattcccg ttaaaattgc atcttctctt gcataccctt ttatcttttt    1680
atcaaaattt ataattcctt ctttaagagc ctctacaaca taatcaggta aacattcttt    1740
taattccctg aattatctgc agagaattcc ccggatcgag atagtatatg atgcatattc    1800
tttaaatata gataaagtta tagaagcaat agaagattta ggatttactg taatataaat    1860 tacacttta aaaagtttaa aaacatgata caataagtta tggttggaat tgttatccgc     1920
tcacaattcc aacttatgat taaaatttta aggaggtgta tttcatatga ccatgattac    1980
gaattcgagc tcggtacccg ggcgccgcc attattttt tgaacaattg acaattcatt      2040 tcttatttt tattaagtga tagtcaaaag gcataacagt gctgaataga aagaaattta     2100
cagaaaagaa aattatagaa tttagtatga ttaattatac tcatttatga atgtttaatt    2160
gaatacaaaa aaaatactt gttatgtatt caattacggg ttaaaatata gacaagttga     2220
aaaatttaat aaaaaaataa gtcctcagct cttatatatt aagctaccaa cttagtatat    2280
aagccaaaac ttaaatgtgc taccaacaca tcaagccgtt agagaactct atctatagca    2340
atatttcaaa tgtaccgaca tacaagagaa acattaacta tatatattca atttatgaga    2400
ttatcttaac agatataaat gtaaattgca ataagtaaga tttagaagtt tatagccttt    2460
gtgtattgga agcagtacgc aaaggctttt ttatttgata aaaattagaa gtatatttat    2520
tttttcataa ttaatttatg aaaatgaaag ggggtgagca aagtgacaga ggaaagcagt    2580
atcttatcaa ataacaaggt attagcaata tcattattga ctttagcagt aaacattatg    2640
acttttatag tgcttgtagc taagtagtac gaaagggga gctttaaaaa gctccttgga    2700
atacatagaa ttcataaatt aatttatgaa aagaagggcg tatatgaaaa cttgtaaaaa    2760
ttgcaaagag tttattaaag atactgaaat atgcaaaata cattcgttga tgattcatga    2820
taaaacagta gcaacctatt gcagtaaata caatgagtca agatgtttac ataaagggaa    2880
agtccaatgt attaattgtt caaagatgaa ccgatatgga tggtgtgcca taaaaatgag    2940
atgttttaca gaggaagaac agaaaaaaga acgtacatgc attaaatatt atgcaaggag    3000
ctttaaaaaa gctcatgtaa agaagagtaa aaagaaaaaa taatttattt attaatttaa    3060
tattgagagt gccgacacag tatgcactaa aaaatatatc tgtggtgtag tgagccgata    3120
caaaaggata gtcactcgca ttttcataat acatcttatg ttatgattat gtgtcggtgg    3180
gacttcacga cgaaaaccca caataaaaaa agagttcggg gtagggttaa gcatagttga    3240
ggcaactaaa caatcaagct aggatatgca gtagcagacc gtaaggtcgt tgtttaggtg    3300
tgttgtaata catacgctat taagatgtaa aaatacggat accaatgaag ggaaaagtat    3360 aattttgga tgtagtttgt ttgttcatct atgggcaaac tacgtccaaa gccgtttcca    3420
aatctgctaa aaagtatatc ctttctaaaa tcaaagtcaa gtatgaaatc ataaataaag    3480
tttaattttg aagttattat gatattatgt ttttctatta aaataaatta agtatataga    3540
atagtttaat aatagtatat acttaatgtg ataagtgtct gacagtgtca cagaaaggat    3600
gattgttatg gattataagc ggccggccga agcaaactta agagtgtgtt gatagtgcag    3660
```

```
tatcttaaaa ttttgtataa taggaattga agttaaatta gatgctaaaa atttgtaatt    3720
aagaaggagt gattacatga acaaaaatat aaaatattct caaaactttt taacgagtga    3780
aaaagtactc aaccaaataa taaaacaatt gaatttaaaa gaaaccgata ccgtttacga    3840
aattggaaca ggtaaagggc atttaacgac gaaactggct aaaataagta aacaggtaac    3900
gtctattgaa ttagacagtc atctattcaa cttatcgtca gaaaaattaa aactgaatac    3960
tcgtgtcact ttaattcacc aagatattct acagtttcaa ttccctaaca aacagaggta    4020
taaaattgtt gggagtattc cttaccattt aagcacacaa attattaaaa agtggtttt    4080 tgaaagccat gcgtctgaca tctatctgat tgttgaagaa ggattctaca agcgtacctt    4140
ggatattcac cgaacactag ggttgctctt gcacactcaa gtctcgattc agcaattgct    4200
taagctgcca gcggaatgct ttcatcctaa accaaaagta aacagtgtct taataaaact    4260
tacccgccat accacagatg ttccagataa atattggaag ctatatacgt actttgtttc    4320
aaaatgggtc aatcgagaat atcgtcaact gtttactaaa aatcagtttc atcaagcaat    4380
gaaacacgcc aaagtaaaca atttaagtac cgttacttat gagcaagtat tgtctatttt    4440
taatagttat ctattattta acgggaggaa ataattctat gagtcgcttt tgtaaatttg    4500
gaaagttaca cgttactaaa gggaatgtgt ttaaactcct ttttgataat ctcatgacca    4560
aaatccctta acgtgagttt tcgttccact gagcgtcaga ccccgtagaa aagatcaaag    4620
gatcttcttg agatcctttt tttctgcgcg taatctgctg cttgcaaaca aaaaaaccac    4680
cgctaccagc ggtggtttgt ttgccggatc aagagctacc aactcttttt ccgaaggtaa    4740
ctggcttcag cagagcgcag ataccaaata ctgtccttct agtgtagccg tagttaggcc    4800
accacttcaa gaactctgta gcaccgccta catacctcgc tctgctaatc ctgttaccag    4860
tggctgctgc cagtggcgat aagtcgtgtc ttaccgggtt ggactcaaga cgatagttac    4920
cggataaggc gcagcggtcg ggctgaacgg ggggttcgtg cacacagccc agcttggagc    4980
gaacgaccta caccgaactg agatacctac agcgtgagca ttgagaaagc gccacgcttc    5040
ccgaagggag aaaggcggac aggtatccgg taagcggcag ggtcggaaca ggagagcgca    5100
cgagggagct ccaggggga aacgcctggt atctttatag tcctgtcggg tttcgccacc    5160
tctgacttga gcgtcgattt ttgtgatgct cgtcaggggg gcggagccta tggaaaaacg    5220
ccagcaacgc ggccttttta cggttcctgg ccttttgctg ccttttgct cacatgttct    5280 ttcctgcgtt atcccctgat tctgtggata accgtattac cgcctttgag tgagctgata    5340
ccgctcgccg cagccgaacg accgagcgca gcgagtcagt gagcgaggaa gcggaagagc    5400
gcccaatacg cagggccccc tgcttcgggg tcattatagc gattttttcg gtatatccat    5460
cctttttcgc acgatataca ggattttgcc aaagggttcg tgtagacttt ccttggtgta    5520
tccaacggcg tcagccgggc aggataggtg aagtaggccc acccgcgagc gggtgttcct    5580
tcttcactgt cccttattcg cacctggcgg tgctcaacgg aatcctgct ctgcgaggct    5640 ggccggctac cgccggcgta acagatgagg gcaagcggat ggctgatgaa accaagccaa    5700
ccaggaaggg cagcccacct atcaaggtgt actgccttcc agacgaacga agagcgattg    5760
aggaaaaggc ggcggcggcc ggcatgagcc tgtcggccta cctgctggcc gtcggccagg    5820
gctacaaaat cacgggcgtc gtggactatg agcacgtccg cgagctggcc cgcatcaatg    5880
gcgacctggg ccgcctgggc ggcctgctga actctggct caccgacgac ccgcgcacgg    5940
cgcggttcgg tgatgccacg atcctcgccc tgctggcgaa gatcgaagag aagcaggacg    6000
```

```
agcttggcaa ggtcatgatg ggcgtggtcc gcccgagggc agagccatga cttttttagc    6060
cgctaaaacg gccgggggt gcgcgtgatt gccaagcacg tccccatgcg ctccatcaag     6120
aagagcgact tcgcggagct ggtgaagtac atcaccgacg agcaaggcaa gaccgatcgg    6180
gccccctgca ggcctcgaga tctccatgga cgcgtgacgt cgactctaga ggatccccgg    6240
gtaccgagaa actaacaggt tggctgataa gtccccggtc taacaaaaaa taagaagcct    6300
gcatttgcag gcttcttatt tttaagctta gacaaacctg aagttaacta tttatcaatt    6360
cctgcaattc gtttacaaaa cggcaaatgt gaaatccgtc acatactgcg tgatgaactt    6420
gaattgccaa aggaagtata attttgttat cttctttata atatttcccc atagtaaaaa    6480
taggaatcaa ataatcatat cctttctgca aattcagatt aaagccatcg aaggttgacc    6540
acggtatcat agatacatta aaaatgtttt ccggagcatt tggctttcct tccattctat    6600
gattgtttcc ataccgttgc gtatcacttt cataatctgc taaaaatgat ttaaagtcag    6660
acttacactc agtccaaagg ctggaaaatg tttcagtatc attgtgaaat attgtatagc    6720
ttggtatcat ctcatcatat atccccaatt caccatcttg attgattgcc gtcctaaact    6780
ctgaatggcg gtttacaatc attgcaatat aataaagcat tgcaggatat agtttcattc    6840
ccttttcctt tatttgtgtg atatccactt taacggtcat gctgtaggta caaggtacac    6900
ttgcaaagta gtggtcaaaa tactcttttc tgttccaact attttttatca attttttcaa    6960
ataccatcta agttccctct caaattcaag tttatcgctc taatgaacaa agatattata    7020
ccacattttt gtgaattttt caacttgccc acttcgactg cactcccgac ttaataactt    7080
cttgaacact tgccgaaaaa caattgtgtc agaccgggga cttatcagcc aacctgttat    7140
acctcgaatt cgtaatcatg gtcataattt attcaacata gttcccttca agagcgatac    7200
aacgattata acgaccttcc aattttttga taccattttg gtagtactcc ttcggttttg    7260
cctcaaaata ggcctcagtt tcggcgatca cctcttcatt gcagccaaat tttttccctg    7320
cgagcatcct tttgaggtct gagaacaaga aaaagtcgct gggggccaga tctggagaat    7380
acggcgggtg gggaagcaat tcgaagccca attcatgaat ttttgccatc gttctcaatg    7440
acttgtggca cggtgcgttg tcttggtgga acaacacttt tttcttcttc atgtggggcc    7500
gttttgccgc gatttcgacc ttcaaacgct ccaataacgc catataatag tcactgttga    7560
tggttttttcc cttctcaaga taatcgataa aaattattcc atgcgcatcc caaaaaacag    7620
aggccattac tttgccagcg gacttttgag tctttccacg cttcggagac ggttcaccgg    7680
tcgctgtcca ctcagccgac tgtcgattgg actcaggagt gtagtgatgg agccatgttt    7740
catccattgt cacatatcga cggaaaaact cgggtgtatt acgagttaac agctgcaaac    7800
accgcttaga atcatcaaca cgtcgttgtt tttggtcaaa tgtgagctcg cgcggcaccc    7860
atttcgcaca gagcttccgc atatccaaat attgatgaat gatatgacca acacgttcct    7920
ttgatatctt taaggcctct gctatctcga tcaacttcat tttacggtca ttcaaaatca    7980
ttttgtggat ttttttgatg ttttcgtcgg taaccacctc tttcgggcgt ccactgcgtt    8040
caccgtcctc cgtgctcatt tcaccacgct tgaattttgc ataccaatca attattgttg    8100
atttccctgg ggcagagtcc ggaaactcat tatcaagcca agttttttgct tccactgtat    8160
tttttccctt cagaaaacag tattttatca aaacacgaaa ttcctttttt tccatcatat    8220
gattttctcc tttactataa tatttttatt gaatattttt acatctaaat gctaaaactc    8280
ttttatatat cctcctttct atttataaaa tatactaata tctacttagg ttttcatata    8340
cattcacttc ctaacatttt aaattgaaga cactcagttg attaatttgc tcttcgattg    8400
```

```
aataaagacg ttgtctgaaa taaatatgta aactttgttc tatataaaat ataaaaatta    8460
agatattctt agattaagtt attgatttta caataaagtt aattctaaaa tttgatttct    8520
attgtaaata tttctttaaa ttcattaagc ggcc                                8554
```

<210> SEQ ID NO 31
<211> LENGTH: 4736
<212> TYPE: DNA
<213> ORGANISM: Artificial Sequence
<220> FEATURE:
<223> OTHER INFORMATION: pMTL-ME6c

<400> SEQUENCE: 31

```
agtaatgtac ttacctttgg ggatttcata actaaaagcg gcagaagaac accatttttt     60
ataaatacag gtaactacaa gacaggtaat caattaaata agttggctaa gttttatgct    120
aaagcaatat atgataattt tggagatgat tttgatattt tatttgggcc tgcatataaa    180
ggaataccct taagtgtttc agtagctatg gcacttgata atatttatgg aattaatgca    240
gcttattgtt caaatagaaa agaagttaaa gatcacggtg ataagggaat acttcttgga    300
gcaaagcttg aagaaggaga cagagttata attgtagaag atgtcacaac agctggtaca    360
tcagtatacg aaacaatgcc tatacttaaa tcacaggctg aggttgatgt aaagggaatc    420
ataatatcag tggatagaat ggaaagaggt aagggagata gagtgccctt aactgaactt    480
aaagaaaagt ttggatttaa acatgttcct attgttacta tggaagaggt agtagaatat    540
ttgtataaga aaaatatcaa tggcaaagta atcatagatg ataaaatgaa agatagaatt    600
aatgagtact ataaagagta tggagtaaaa tagtaagcgg ccgctgtatc catatgacca    660
tgattacgaa ttcgagctcg gtacccgggg atcctctaga gtcgacgtca cgcgtccatg    720
gagatctcga ggcctgcaga catgcaagct tggcactggc cgtcgtttta caacgtcgtg    780
actgggaaaa ccctggcgtt acccaactta atcgccttgc agcacatccc cctttcgcca    840
gctggcgtaa tagcgaagag gcccgcaccg atcgcccttc ccaacagttg cgcagcctga    900
atggcgaatg cgctagtat aaaaataaga agcctgcatt tgcaggcttc ttattttat     960 gctagctaaa ataaatgtgc ctcaacttag atgttaaggc acatttattt tatatattat   1020
tcatgttttg aaacattttt atcttttgtg tattttacgt gtagtaattt gtgagcaagt   1080
ccttcacctg gttttccaaa gtagctatca tacattttaa taatagctgg attatcatgt   1140
gactttctct ttgaaagaac attttttatct tggttgtata atactgatgc tcttagtttt   1200
ctgtaatcaa cattttctct atcaagagca tttacgtgag gttgacctcc accatttata   1260
catccaccag ggcaagccat tacttctata aagtgatatt gttttttcgtt cattttttcca  1320 gatttcataa actcgaagaa gttagaagca ccatttataa cagcaacgtt tagtttattt   1380
ccagcaattt caacttccgc ttctttttatg cctttaaagc ctcttacttc agtgtaatca   1440
acattttcaa gttctttatt ttcagcaaag tctttagctg atcttattgc agcttccata   1500
acgccaccgg ttgcaccaaa gatagctcca gcaccactgt aagtacccat agcaggatca   1560
acttcaccat cttcaagatc tgcaaattta attttttgcat ctttaatcat ttttgcaagc   1620
tctcttgtag ttaaggatgc atcaatatct cttaagctgt tagtttccat gaaaggaata   1680
tctgcttcat atttttttatc attacaaggc atgatagtaa ctgtataaac atcttctgga   1740
gctattcctg aaattgaagg atagtaagtt tttgatgcag taccaaatat ttgttgtggt   1800
gattttgctg atgaaagatt atctaataat tcaggatgat aattttgagc taatcttacc   1860
```

```
catgcaggac agcaagatgt aaacataggg aatgggccat tatttttaac tctgcctaaa    1920
agttcagtag cttcttccat tatagtcata tctgcaccaa agtttatatc aaatacttta    1980
tcaaagccta acattctaag tgcagtatat agttttcctg ttacatcttt tccatatccc    2040
attttgaata attcgcccat agcagttctt actgatggag ccattgcaac aatgacatgt    2100
tttttagggt cattaagagc ttcttgaact ttttctatat gggattttc ttttaaagca     2160 gcaacaggcg cgccgcattc acttcttttc tatataaata tgagcgaagc gaataagcgt    2220
cggaaaagca gcaaaaagtt ccttttttgc tgttggagca tgggggttca ggggtgcag     2280 tatctgacgt caatgccgag cgaaagcgag ccgaagggta gcatttacgt tagataaccc    2340
cctgatatgc tccgacgctt tatatagaaa agaagattca actaggtaaa atcttaatat    2400
aggttgagat gataaggttt ataaggaatt tgtttgttct aattttcac tcattttgtt     2460 ctaatttctt ttaacaaatg ttcttttttt tttagaacag ttatgatata gttagaatag    2520
tttaaaataa ggagtgagaa aaagatgaaa gaaagatatg gaacagtcta taaggctct     2580 cagaggctca tagacgaaga aagtggagaa gtcatagagg tagacaagtt ataccgtaaa    2640
caaacgtctg gtaacttcgt aaaggcatat atagtgcaat taataagtat gttagatatg    2700
attggcggaa aaaacttaa aatcgttaac tatatcctag ataatgtcca cttaagtaac      2760
aatacaatga tagctacaac aagagaaata gcaaaagcta caggaacaag tctacaaaca    2820
gtaataacaa cacttaaaat cttagaagaa ggaaatatta taaaagaaa aactggagta     2880 ttaatgttaa accctgaact actaatgaga ggcgacgacc aaaaacaaaa atacctctta    2940
ctcgaatttg ggaactttga gcaagaggca aatgaaatag attgacctcc caataacacc    3000
acgtagttat tgggaggtca atctatgaaa tgcgattaag ggccggccaa gtgggcaagt    3060
tgaaaaattc acaaaaatgt ggtataatat ctttgttcat tagagcgata aacttgaatt    3120
tgagagggaa cttagatggt attttgaaaaa attgataaaa atagttggaa cagaaaagag    3180
tattttgacc actactttgc aagtgtacct tgtacctaca gcatgaccgt taaagtggat    3240
atcacacaaa taaggaaaa gggaatgaaa ctatatcctg caatgcttta ttatattgca     3300
atgattgtaa accgccattc agagtttagg acggcaatca atcaagatgg tgaattgggg    3360
atatatgatg agatgatacc aagctataca atatttcaca atgatactga acattttcc     3420 agcctttgga ctgagtgtaa gtctgacttt aaatcatttt tagcagatta tgaaagtgat    3480
acgcaacggt atggaaacaa tcatagaatg gaaggaaagc caaatgctcc ggaaaacatt    3540
tttaatgtat ctatgatacc gtggtcaacc ttcgatggct ttaatctgaa tttgcagaaa    3600
ggatatgatt atttgattcc tatttttact atggggaaat attataaaga agataacaaa    3660
attatacttc ctttggcaat tcaagttcat cacgcagtat gtgacggatt tcacatttgc    3720
cgttttgtaa acgaattgca ggaattgata aatagttaac ttcaggtttg tctgtaacta    3780
aaaacaagta tttaagcaaa aacatcgtag aaatacggtg ttttttgtta ccctaagttt    3840
aaactccttt ttgataatct catgaccaaa atcccttaac gtgagtttc gttccactga     3900 gcgtcagacc ccgtagaaaa gatcaaagga tcttcttgag atcctttttt tctgcgcgta    3960
atctgctgct tgcaaacaaa aaaaccaccg ctaccagcgg tggtttgttt gccggatcaa    4020
gagctaccaa ctctttttcc gaaggtaact ggcttcagca gagcgcagat accaaatact    4080
gtccttctag tgtagccgta gttaggccac cacttcaaga actctgtagc accgcctaca    4140
tacctcgctc tgctaatcct gttaccagtg gctgctgcca gtggcgataa gtcgtgtctt    4200
accgggttgg actcaagacg atagttaccg gataaggcgc agcggtcggg ctgaacgggg    4260
```

```
ggttcgtgca cacagcccag cttggagcga acgacctaca ccgaactgag atacctacag    4320
cgtgagctat gagaaagcgc cacgcttccc gaagggagaa aggcggacag gtatccggta    4380
agcggcaggg tcggaacagg agagcgcacg agggagcttc caggggggaaa cgcctggtat    4440 ctttatagtc ctgtcgggtt tcgccacctc tgacttgagc gtcgattttt gtgatgctcg    4500
tcaggggggc ggagcctatg gaaaaacgcc agcaacgcgg ccttttttacg gttcctggcc    4560 ttttgctggc cttttgctca catgttcttt cctgcgttat cccctgattc tgtggataac    4620
cgtattaccg cctttgagtg agctgatacc gctcgccgca gccgaacgac cgagcgcagc    4680
gagtcagtga gcgaggaagc ggaagagcgc ccaatacgca gggcccctg caggag         4736

<210> SEQ ID NO 32
<211> LENGTH: 45
<212> TYPE: DNA
<213> ORGANISM: Artificial Sequence
<220> FEATURE:
<223> OTHER INFORMATION: Primer catP-INV-F1

<400> SEQUENCE: 32
taaatcattt ttagcagatt atgaaagtga tacgcaacgg tatgg                    45

<210> SEQ ID NO 33
<211> LENGTH: 45
<212> TYPE: DNA
<213> ORGANISM: Artificial Sequence
<220> FEATURE:
<223> OTHER INFORMATION: Primer cat-INV-R1

<400> SEQUENCE: 33
tattgtatag cttggtatca tctcatcata tatccccaat tcacc                    45

<210> SEQ ID NO 34
<211> LENGTH: 45
<212> TYPE: DNA
<213> ORGANISM: Artificial Sequence
<220> FEATURE:
<223> OTHER INFORMATION: Primer catP-INV-R2

<400> SEQUENCE: 34
tatttgtgtg atatccactt taacggtcat gctgtaggta caagg                    45
```

CONDITIONAL VECTORS AND USES THEREOF

CROSS-REFERENCE TO RELATED APPLICATION

The present application is the U.S. 371 National Stage Application of PCT International Application No. PCT/GB2013/050843, with an international filing date of Mar. 28, 2013, which claims the benefit of and priority to United Kingdom Application No. 1205795.6, filed Mar. 30, 2012, the contents of which are incorporated herein by reference in their entireties.

SEQUENCE LISTING

The instant application contains a Sequence Listing which has been submitted in ASCII format via EFS-WEB and is hereby incorporated by reference in its entirety. Said ASCII copy, is named final_sequence_listing_JA62132P_USP_ST25 and is 97.1 KB.

The present invention relates to a novel vector useful in the field of recombinant DNA technology, in particular the vector may be a conditional vector.

Conditional vectors are a pivotal tool in the genetic manipulation of bacterial strains, such vectors only replicate and are maintained during cell growth under a permissive condition. Under a non-permissive condition, their replicative maintenance in the cell is curtailed. This facility makes them ideal vehicles for a number of purposes.

Conditional vectors may be used in the delivery of transposable elements. Thus, a conditional vector carrying a transposable element is first introduced into a bacterial cell by either conjugation or transformation and the transconjugants/transformants selected under the permissive condition. The cells are then grown under the non-permissive condition during which selection is imposed for the presence of the transposon, typically where the transposon carries a gene encoding for antibiotic resistance, and the media is supplemented with an appropriate antibiotic. As the plasmid can no longer replicate, antibiotic resistant progeny can only arise if the transposon has inserted into a non-essential region of the host bacterial genome.

One of the most common forms of a conditional vector is a vector that is only stably maintained under a permissive temperature e.g., 30° C. and is not able to replicate at a higher, non-permissive temperature, e.g., 42° C. This can be a consequence of the temperature instability of a key component of the replication machinery, such as the replication protein or an essential RNA component that does not fold appropriately at the non-permissive temperature.

There are no known temperature sensitive vectors that function in members of the class Clostridia. Indeed, there are no known conditional vectors of any description for use in these bacteria.

To date, no effective transposon has been developed for use in any Clostridia, other than *Clostridium difficile* (Cartman S T and Minton N P, 2010, *Applied Environmental Microbiology*, 76: 1103-9). The transposon system developed for *Clostridium difficile* is based on Himar1C9 mariner, and the plasmid made designated pMTL-SC1 (Cartman S T and Minton N P, 2010, *Applied Environmental Microbiology*, 76: 1103-1109). It consists of a mini-transposon in which the selectable marker catP (resistance to thiamphenicol/chloramphenicol) is flanked by inverted repeat regions (ITR1 & ITR2), proceeded by the transposase gene. Transposition is by a 'cut and paste' mechanism—the transposase 'cuts' out the mini-transposon at ITR1/ITR2, and then 'pastes' it into the genome at random at any 'TA' dinucleotide.

The present invention now provides a conditional vector for use in a Clostridial host in which plasmid replication is effected by transcription from an inducible promoter. The inducible promoter system may be any system that functions in a Clostridial host. The system has been exemplified using two such promoters. In the first, a synthetic lac operator is incorporated into the promoter region of the *C. pasteurianum* ferredoxin gene (to create the $P_{fac}$ promoter), and the expression of lacI placed under the control of a constitutive clostridial promoter, in this case the $P_{ptb}$ promoter of the *Clostridium beijerincjkii* phosphotransbutyrylase gene, ptb promoter. Transcription from $P_{fac}$ is induced by the addition of IPTG. In the second, the $P_{fdx}$ promoter of the *Clostridium sporogenes* ferredoxin fdx gene has been derivatised to include a synthetic operator of the tet gene promoter (creating the $P_{fet}$ promoter), and the gene encoding the TetR repressor placed under the transcriptional control of a constitutive clostridial promoter, in this case the $P_{thl}$ promoter of the *Clostridium acetobutylicum* thiolase gene, thl. Induction from $P_{fet}$ is induced by the addition of anhydrotetracycline (ATc).

In both examples, the induction of the promoter leads to transcription into the plasmid replication region. The positioning of either the $P_{fac}$ or $P_{fet}$ promoter upstream of the plasmid replication region, which may be the pCB102 replication region, results in plasmids that effectively replicate in the desired clostridial host in the absence of inducer. Following addition of inducer, and growth of the cells containing the plasmid in the absence of antibiotic selection, the plasmids are rapidly lost from the population. If a transcriptional terminator is positioned between either the $P_{fac}$ or $P_{fet}$ promoter and the plasmid replication region, then the addition of inducer has no affect on maintenance of the plasmid. This observation established that interference with replication is a direct result of transcription into the plasmid replication region.

In a specific embodiment, when a plasmid carrying the $P_{fac}$ promoter positioned upstream of the pCB102 plasmid replication region is introduced into *Clostridium acetobutylicum* ATCC 824 in the absence of IPTG subsequent growth of the transformants in the presence of IPTG, and then plating on agar containing this inducer, results in almost complete plasmid loss after just 12 hours growth.

Similarly, in an alternative embodiment, when a plasmid carrying the $P_{fet}$ promoter positioned upstream of the pCB102 plasmid replication region is introduced into *Clostridium difficile* in the absence of aTet subsequent growth of the transformants in the presence of aTet, and then plating on agar containing this inducer, results in almost complete plasmid loss after just 12 hours growth.

According to a first aspect, the invention provides a conditional vector comprising DNA encoding for:
(i) an inducible expression cassette comprising an inducible promoter operably linked to a plasmid replication region; and
(ii) a selectable marker.

The conditional vector may also contain a transposable element. The transposable element may be any transposon or sequence of DNA that can move around to different positions within the genome of a single cell, a process called transposition. The transposon may be a Class I or Class II transposon.

The transposon may be selected from Himar1 C9', Tn-3, γδ, Tn10, Tn5, Tnpho903, Tn917, Bacteriophage Mu and related viruses.

'Himar1 C9' refers to a mini-transposon in which the selectable marker, such as catP (encoding chloramphenicol acetyltransferase and responsible for resistance to thiamphenicol or chloramphenicol), is flanked by inverted repeat regions (ITR1 and ITR2), proceeded by the transposase gene.

The conditional vector may also contain a transposase. Preferably, the conditional vector contains a transposase and a transposon which may be a mini-transposon comprising a marker gene flanked by the invert repeat target sites of the transposase. Preferably, the conditional vector contains a transposase and the mini-transposon, Himar1 C9.

According to another aspect of the invention, there is provided a method of delivering a transposon into a bacterial host genome comprising:
(a) introducing a conditional vector into the bacterial cell wherein the conditional vector comprises DNA encoding for:
(i) an inducible expression cassette comprising an inducible promoter operably linked to a plasmid replication region;
(ii) a transposable element;
(iii) a selectable marker; and optionally
(iv) a transposase operably linked to a promoter.

According to the method above, induction of the inducible promoter leads to transcription into the plasmid replication region. The positioning of the inducible promoter upstream of the plasmid replication region results in plasmids that effectively replicate in the bacterial host in the absence of an inducer. When an inducer is added, the growth of bacterial cells containing the plasmid in the absence of antibiotic selection result in plasmids bring rapidly lost from the population.

A conditional vector may be a plasmid.

An inducible expression cassette may comprise DNA encoding for an inducible promoter which includes any promoter which is activated only in the presence of a particular molecule, an inducer. The inducible promoter may be $P_{fac}$, $P_{fet}$ or $P_{xylA}$.

The $P_{fac}$ promoter is from plasmid pMTL5401Fcat (Heap J T et al., *Journal of Microbiological Methods*, 2007, 703: 452-64). In this plasmid, the promoter of the *Clostridium pasteurianum* ferredoxin had been modified to include a lac operator sequence, SEQ ID NO: 1

(AATTGTTATCCGCTCACAATT), inserted immediately downstream of the +1 transcriptional initiation site. The inclusion of a lac operator sequence allows the promoter to be inducible. The $P_{fac}$ promoter may comprise the following sequence, SEQ ID NO: 2:

ACACTTTTAAAAAGTTTAAAAACATGATACAATAAGTTATGGTTGG<u>AAT</u>

<u>TGTTATCCGCTCACAATT</u>CCAAC wherein the bold highlights represent the −35 (TTTAAA) and −10 (TACAAT) sequences, respectively; underlined bases represent the lac operator sequence (AATTGTTATCCGCTCACAATT).

The $P_{fet}$ promoter is derived from the $P_{fdx}$ promoter of the *Clostridium sporogenes* ferredoxin gene (Takamizawa et al., 2004, *Protein Expression and Purification* 36: 70-75) through the incorporation of the requisite Tet operator sequence, SEQ ID NO: 3 (TCTATCATTGATAGG) between the −35 (TTTAAA) and −10 (TAAAAT) sequence of $P_{fdx}$. The $P_{fet}$ promoter may comprise the following sequence, SEQ ID NO: 4:

AAATTACTTTAAA<u>ATCTATCATTGATAGG</u>GTAAAATATAAATCGTATAA

AGTTGT wherein the bold highlighted bases represent the −35 (TTTAAA) and −10 (TAAAAT) sequences, respectively; underlined bases represent the tet operator sequence (TCTATCATTGATAGG).

The $P_{xylA}$ promoter is from the *Staphylococcus xylosus* xylose operon promoter-repressor regulatory system (Girbal et al., *Applied and Environmental Microbiology* 2003, 69(8): 4985-4988) as defined in SEQ ID NO:5. TTTACAAAAAATGAACAATGTGCTATATT (GenBank Accession X57599.1).

An inducible expression cassette may also comprise a regulatory gene which is placed under the control of a constitutive promoter. A regulatory gene is a gene that produces a repressor substance that inhibits an operator gene. The regulatory gene may be LacI or TetR (AAB17268.1 and NP_058294.1, respectively).

LacI is translated to produce a Lac repressor protein, which can bind to the operator of the lac operon (the lac operator) and prevent transcription.

TetR refers to the tetracycline resistance regulatory gene (TetR) of transposon Tn10. This gene is located on a 695-base pair HincII DNA fragment near the centre of Tn10. Expression of the TetR gene is preferably under the control of a constitutive promoter, in this instance the promoter ($P_{thl}$) of the thiolase gene of *Clostridium acetobutylicum*. Production of the TetR protein turns off transcription from the $P_{fet}$ promoter due to interaction with the Tet operator. Addition of the inducer, tetracycline prevents TetR binding to the Tet operator and thereby allows expression from the $P_{fet}$ promoter.

The term 'promoter' as used herein refers to a sequence of DNA, usually upstream (5') to the coding sequence of a structural gene, which controls the expression of the coding region by providing the recognition for RNA polymerase and/or other factors preferably required for transcription to initiate at the correct site.

A 'constitutive' promoter refers to an unregulated promoter that allows for continual transcription of its associated gene. The constitutive promoter may be $P_{ptb}$ or $P_{thl}$.

The $P_{ptb}$ promoter is from the phosphotransbutyrlase gene ptb of *Clostridium beijerinckii* NCIMB 8052 (GenBank Accession L04468.1).

The $P_m$, promoter is based on the promoter of the thiolase gene of *Clostridium acetobutylicum* ATCC 824 (GenBank Accession NC_003030.1). The synthesised fragment may comprise the following sequence, SEQ ID NO: 6:

TATATTGATAAAAATAATAATAGTGGGTATAATTAAGTTGTTAGAGAAA

ACGTATAAATT wherein the highlighted bases represent the −35 (TTGATA) and −10 (TATAAT) sequences, respectively.

The inducible promoter is operably linked to the plasmid replication region. The plasmid replication region refers to a plasmid-derived segment of DNA that mediates the autonomous replication of the plasmid.

The plasmid replication region may be pCB102. pCB102 refers to the pCB102 plasmid replication region from *Clostridium butyricum* as described in (Minton N P and Morris J G, 1981, *Journal of General Microbiology*, 127: 325-331). The pCB102 plasmid replication region may comprise the following sequence, SEQ ID NO: 7:

```
GCCATTATTTTTTTGAACAATTGACAATTCATTTCTTATTTTTTATTAAGTGATA

GTCAAAAGGCATAACAGTGCTGAATAGAAAGAAATTTACAGAAAAGAAAATTA

TAGAATTTAGTATGATTAATTATACTCATTTATGAATGTTTAATTGAATACAAA

AAAAAATACTTGTTATGTATTCAATTACGGGTTAAAATATAGACAAGTTGAAAA

ATTTAATAAAAAAATAAGTCCTCAGCTCTTATATATTAAGCTACCAACTTAGTA

TATAAGCCAAAACTTAAATGTGCTACCAACACATCAAGCCGTTAGAGAACTCT

ATCTATAGCAATATTTCAAATGTACCGACATACAAGAGAAACATTAACTATAT

ATATTCAATTTATGAGATTATCTTAACAGATATAAATGTAAATTGCAATAAGTA

AGATTTAGAAGTTTATAGCCTTTGTGTATTGGAAGCAGTACGCAAAGGCTTTT

TTATTTGATAAAAATTAGAAGTATATTTATTTTTTCATAATTAATTTATGAAAAT

GAAAGGGGGTGAGCAAAGTGACAGAGGAAAGCAGTATCTTATCAAATAACAA

GGTATTAGCAATATCATTATTGACTTTAGCAGTAAACATTATGACTTTTATAGT

GCTTGTAGCTAAGTAGTACGAAAGGGGGAGCTTTAAAAAGCTCCTTGGAATA

CATAGAATTCATAAATTAATTTATGAAAAGAAGGGCGTATATGAAAACTTGTA

AAAATTGCAAAGAGTTTATTAAAGATACTGAAATATGCAAAATACATTCGTTG

ATGATTCATGATAAAACAGTAGCAACCTATTGCAGTAAATACAATGAGTCAAG

ATGTTTACATAAAGGGAAAGTCCAATGTATTAATTGTTCAAAGATGAACCGAT

ATGGATGGTGTGCCATAAAAATGAGATGTTTTACAGAGGAAGAACAGAAAAA

AGAACGTACATGCATTAAATATTATGCAAGGAGCTTTAAAAAAGCTCATGTAA

AGAAGAGTAAAAAGAAAAAATAATTTATTTATTAATTTAATATTGAGAGTGCCG

ACACAGTATGCACTAAAAAATATATCTGTGGTGTAGTGAGCCGATACAAAAG

GATAGTCACTCGCATTTTCATAATACATCTTATGTTATGATTATGTGTCGGTG

GGACTTCACGACGAAAACCCACAATAAAAAAAGAGTTCGGGGTAGGGTTAAG

CATAGTTGAGGCAACTAAACAATCAAGCTAGGATATGCAGTAGCAGACCGTA

AGGTCGTTGTTTAGGTGTGTTGTAATACATACGCTATTAAGATGTAAAAATAC

GGATACCAATGAAGGGAAAAGTATAATTTTTGGATGTAGTTTGTTTGTTCATC

TATGGGCAAACTACGTCCAAAGCCGTTTCCAAATCTGCTAAAAAGTATATCCT

TTCTAAAATCAAAGTCAAGTATGAAATCATAAATAAAGTTTAATTTTGAAGTTA

TTATGATATTATGTTTTTCTATTAAAATAAATTAAGTATATAGAATAGTTTAATA

ATAGTATATACTTAATGTGATAAGTGTCTGACAGTGTCACAGAAAGGATGATT

GTTATGGATTATAAGC
```

The plasmid replication region may have a sequence identity or sequence homology of at least 60%, 65%, 70%, 75%, 80%, 85%, 90%, 95%, 98%, 99% or 100% to pCB102 (SEQ ID NO: 7).

A nucleic acid has 'identity', 'homology' or is 'homologous' to a second nucleic acid if the first nucleic acid sequence has a similar sequence to the second nucleic acid sequence. In a preferred embodiment, a homologous nucleic acid is one that exhibits at least 65% sequence homology to the plasmid replication region, more preferred is at least 70% sequence homology. Even more preferred are homologous nucleic acids that exhibit at least 75%, 80%, 85%, or 90% sequence homology to the plasmid replication region. In a yet more preferred embodiment a homologous nucleic acid exhibits at least 95%, 98%, 99% or 99.9% sequence identity. As used herein, homology between two regions of nucleic acid sequence (especially with respect to related structural similarities) is interpreted as implying similarity in function. The term 'homology' is synonymous with the term 'identity.'

The pCB102 plasmid replication region may comprise DNA encoding the putative RepH protein which may comprise the following sequence, SEQ ID NO: 8:

MKRRAYMKTCKNCKEFIKDTEICKIHSLMIHDKTVATYCSKYNESRCLH

KGKVQCINCSKMNRYGWCAIKMRCFTEEEQKKERTCIKYYARSFKKAHV

KKSKKKK

The nucleic acid sequence of RepH is underlined in SEQ ID NO:7.

The selectable marker may be a gene which allows for the selection of transformed host cells. Selectable marker genes are well known in the art and will vary with the host cell used. Preferred selectable marker genes are those specifying resistance to antibiotics, nucleoside and amino acid analogues and heavy metals, as well as markers complementing auxotrophic phenotypes. Antibiotic resistance markers include those specifying resistance to tetracycline (such as tetM and tetA), erythromycin and lincomyin (such as ermB) ampicillin (such as bla), penicillin (such as penP) chloramphenicol and thiamphenicol (such as catP), kanamycin (such as kan), spectinomycin (such as aad9) and streptomycin. Nucleoside analogues include fluoroorotic acid and 5'-fluorocytosine. Auxotrophic markers include leuB, proC, pyre, purE and pyrF.

According to another aspect of the invention, there is provided use of a conditional vector for transposon delivery in Clostridia wherein the conditional vector comprises DNA encoding:
(i) an inducible expression cassette comprising an inducible promoter operably linked to a plasmid replication region;
(ii) a transposable element; and
(iii) a selectable marker; and optionally
(iv) a transposase operably linked to a promoter.

A 'transposase' is an enzyme that binds to the ends of a transposon and catalyzes the movement of the transposon to another part of the genome by a variety of mechanisms, including a cut and paste mechanism or a replicative transposition mechanism.

The transposase may be expressed in the bacterial host genome. The transposase may be located on the conditional vector of the present invention or on a separate vector or integrated into the host chromosomal DNA.

The transposase may be operably linked to a promoter. The promoter may be a constitutive promoter. Alternatively, the transposase may be operably linked to a promoter recognised by the group 5 polymerase sigma factor. Preferably, the transposase is operably linked to a tcdA or tcdB promoter.

The conditional vector may also contain additional elements. An additional element may be a group 5 RNA polymerase sigma factor which includes BotR (GenBank Accession Number YP_001253340), TetR (GenBank Accession Number NP_780796), TcdR (Genbank Accession Number AM180355) and UviA (GenBank Accession Number ABG87874) as described in (Dupuy et al., 2006, *Molecular Microbiology*, 60(4): 1044-1057; Dupuy and Matamouros, 2006, *Research Microbiology*, 157: 201-205).

Expression of the transposase may be driven by a group 5 RNA polymerase sigma factor and its associated promoter.

Accordingly, in a preferred embodiment, the conditional vector of the present invention utilises the *Clostridium difficile* TcdR sigma factor (TcdR encoded by tcdR) responsible for the expression of the two toxins, TcdA and TcdB, encoded by tcdA and tcdB, respectively.

The TcdR sigma factor may be from any toxinogenic strain of *Clostridium difficile*, such as strain 630 (Genbank Accession Number AM180355). TcdR (formerly called TxeR, Mani and Dupuy, 2001, Proc Natl Acad Sci USA. 98: 5844-5849 or TcdD, Rupnik M, et al., 2005, Journal of Medical Microbiology 54: 113-117) comprises 184 amino acids which may comprise the following sequence, SEQ ID NO:9. A typical representative is that of GenBank Accession Number CAJ67491 as defined in SEQ ID NO: 9 below:

MQKSFYELIVLARNNSVDDLQEILFMFKPLVKKLSRVLHYEEGETDLII

FFIELIKNIKLSSFSEKSDAIIVKYIHKSLLNKTFELSRRYSKMKFNFV

EFDENILNMKNNYQSKSVFEEDICFFEYILKELSGIQRKVIFYKYLKGY

SDREISVKLKISRQAVNKAKNRAFKKIKKDYENYFNL

The TcdR sigma factor is approximately 22-kDa in size and contains a potential C-terminal helix-turn-helix DNA-binding motif. The TcdR sigma factor shows sequence similarities to TetR, a positive regulator of the tetanus toxin gene in *Clostridium tetani*, BotR, a positive regulator of the botulism toxin genes in *Clostridium botulinum* and UviA, a putative positive regulator of the UV-inducible bacteriocin (bcn) gene of *Clostridium perfringens*.

The tcdA promoter may be from any toxinogenic strain of *Clostridium difficile*, such as strain 630. The promoter may comprise the following sequence, SEQ ID NO: 10: tataagatatgtttacaaattactatcagacaatctccttatctaataGaagagtcaattaactaat. The bold sequences tttaca and ctcctt represent the promoter −35 and −10 regions, respectively.

The tcdB promoter may be from any toxinogenic strain of *Clostridium difficile*, such as strain 630. The promoter may comprise the following sequence, SEQ ID NO:11: atctaagaatatcttaattttatattttatatagaacaaagtttacatatttatttcagacaacgtctttattcaatcga aga, which contains two overlapping promoter sequences comprising ptcdB1 ptcdB2.

ptcdB1 (SEQ ID NO: 12):
gaacaaagtttacatatttatttcagacaacgtctttattcaatcGaaga ptcdB22 (SEQ ID NO: 13):
atctaagaatatcttaatttttatattttatatagaacaaagtttAcata The bold sequences tctaag and tatttt represent the promoter −35 and −10 regions, respectively.

The conditional vector of the present invention is preferably for use in a bacterial cell, such as a bacterial cell from the class Clostridia, including the genus *Clostridium*. Preferably, the conditional vector is for use in the species *Clostridium acetobutylicum*.

The bacterial cell may be any bacterial species, but preferably members of the bacterial phylum Firmicutes composed of the class Clostridia (orders Clostridiales, Halanaerobiales, Natranaerobiales and Thermoanaerobacterales), the class Bacilli (orders Bacillales and Lactobacillales) and the class Mollicutes (orders Acholeplasmatales, Anaeroplasmatales, Entomoplasmatales, Haloplasmatales and Mycoplasmatales). Within the order Clostridiales is the genus, *Clostridium*. Preferred species are *C. acetobutylicum, C. aerotolerans, C. baratii, C. beijerinckii, C. bifermentans, C. botulinum, C. butyricum, C. cadaveris, C. cellulolyticum, C. chauvoei, C. clostridioforme, C. colicanis, C. difficile, C. estertheticum, C. fallax, C. feseri, C. formicaceticum, C. histolyticum, C. innocuum, C. kluyveri, C. ljungdahlii, C. lavalense, C. novyi, C. oedematiens, C. paraputrificum, C. pasteurianum, C. perfringens, C. phytofermentans, C. piliforme, C. ragsdalei, C. ramosum, C. scatologenes, C. septicum, C. sordellii, C. sporogenes, C. sticklandii, C. tertium, C. tetani, C. thermocellum, C. thermosaccharolyticum, C. tyrobutyricum, C. paprosolvens, C. saccharobutylicum, C. carboxidovorans, C. scindens*, and *C. autoethanogenum*. Within the order Bacillales are Bacillaceae which include the genera *Bacillus* and *Geobacillus*, and Staphylococcaceae, which include the genus *Staphylococcus*. Preferred *Bacillus* species are: *B. alcalophilus, B. aminovorans, B. amyloliquefaciens, B. anthracis, B. caldolyticus, B. circu-* lans, B. coagulans, Bglobigii, B. licheniformis, B. natto, B. polymyxa, B. phaericus, B. stearothermophilus, B. subtilis, B. thermoglucosidasius, B. thuringiensis and B. vulgatis. Preferred Geobacillus species are: G. debilis, G. stearothermophilus, G. thermocatenulatus, G. thermoleovorans, G. kaustophilus, G. thermoglucosidasius, G. thermodenitrificans, G. gargensis, G. jurassicus, G. lituanicus, G. pallidus, G. subterraneus, G. tepidamans, G. thermodenitrificans, G. thermoglucosidasius, G. thermoleovorans, G. toebii, G. uzenensis and G. vulcani. Preferred Staphylococcus species include: S. arlettae, S. aureus, S. auricularis, S. capitis, S. caprae, S. carnosus, S. chromogenes, S. cohnii, S. condimenti, S. delphini, S. devriesei, S. epidermidis, S. equorum, S. felis, S. fleurettii, S. gallinarum, S. haemolyticus, S. hominis, S. hyicus, S. intermedius, S. kloosii, S. leei, S. lentus, S. lugdunensis, S. lutrae, S. lyticans, S. massiliensis, S. microti, S. muscae, S. nepalensis, S. pasteuri, S. pettenkoferi, S. piscifermentans, S. pseudintermedius, S. pulvereri, S. rostri, S. saccharolyticus, S. saprophyticus, S. schleiferi, S. sciuri, S. simiae, S. simulans, S. stepanovicii, S. succinus, S. vitulinus, S. warneri and S. xylosus.

Preferably, the bacterial cell is C. acetobutylicum, C. difficile, C. beijerinckii, C. ljungdahlii, C. kluyveri, C. botulinum, C. autoethanogenum, C. pasteurianum, C. saccharobutylicum, C. carboxidovorans, C. sporogenes, C. phytofermentans, C. ragsdalei, C. tyrobutyricum, C. perfringens, C. butyricum, C. cellulolyticum, C. formicaceticum, C. novyi, C. scatologenes, C. septicum, C. sordellii, C. sticklandii, C. tetani, C. thermocellum, C. thermosaccharolyticum, C. paprosolvens, C. scindens, or C. bifermentans.

Preferably the bacterial cell is C. ljungdahlii. Preferably, the bacterial cell is C. acetobutylicum. Preferably the bacterial cell is C. autoethanogenum. Preferably, the bacterial cell is C. carboxidovorans. Preferably, the bacterial cell is C. ragsdalei. Preferably, the bacterial cell is C. scatologenes. Preferably, the bacterial cell is C. scindens. Preferably, the bacterial cell is C. pasteuranium. Preferably, the bacterial cell is C. phytofermentans. Preferably, the bacterial cell is C. beijerinckii.

Another aspect of the invention further provides a conditional vector comprising DNA encoding for:
(i) an inducible expression cassette comprising an inducible promoter operably linked to a plasmid replication region;
(ii) a regulatory protein placed under the control of a constitutive promoter;
(iii) a transposable element;
(iv) a transposase; and
(v) a selectable marker.

Another aspect of the invention provides a conditional vector comprising DNA encoding for:
(i) an inducible expression cassette comprising an inducible promoter operably linked to a plasmid replication region;
(ii) a regulatory protein placed under the control of a constitutive promoter;
(iii) a transposable element;
(iv) a selectable marker; and optionally
(v) a transposase wherein the transposase is operably linked to a promoter recognised by the group 5 polymerase sigma factor; and optionally
(vi) a group 5 RNA polymerase sigma factor.

Another aspect of the invention further provides a bacterial cell comprising a conditional vector according to the invention. The group 5 RNA polymerase sigma factor is either located on the conditional vector, a separate vector or in the bacterial host genome.

According to yet another aspect of the invention, there is provided a method of delivering a transposon into a bacterial host genome comprising:
(a) introducing an expression vector comprising DNA encoding a group 5 RNA polymerase sigma factor into the bacteria; and
(b) introducing a conditional vector according to the invention into the bacterial cell.

In step (a) the DNA may be located on the conditional vector of (b), on a separate vector or in the bacterial host genome.

DNA may be introduced by transfection, conjugation or any other suitable method.

The conditional vector may comprise DNA encoding for:
(i) an inducible expression cassette comprising an inducible promoter operably linked to a plasmid replication region;
(ii) a transposable element;
(iii) a selectable marker; and optionally
(iv) a transposase operably linked to a promoter recognised by the group 5 RNA polymerase sigma factor.

According to another further aspect of the invention, there is provided use of a conditional vector for transposon delivery in Clostridia wherein the conditional vector comprises DNA encoding for:
(i) an inducible expression cassette comprising an inducible promoter operably linked to a plasmid replication region;
(iii) a regulatory protein placed under the control of a constitutive promoter;
(iv) a transposable element;
(v) a selectable marker; and optionally
(vi) a transposase operably linked to a constitutive promoter.

According to yet another aspect of the invention, there is provided a method of delivering a transposon into a bacterial cell comprising:
(i) introducing an conditional vector according to the invention;
(ii) adding an inducer, wherein the inducer activates the inducible expression cassette;
(iii) adding a selection agent; and
(iv) selecting for the occurrence of transposon events The inducer may be IPTG or tetracycline.

The selection agent may be tetracycline, erythromycin, lincomycin, ampicillin, penicillin, chloramphenicol, thiamphenicol, kanamycin, spectinomycin fluoroorotic acid, 5-fluorocytosine or streptomycin.

Use of the Conditional Vector in Generating Transposon Libraries and Screening for Mutants of a Bacterial Strain Affected in Solvent Production, Tolerance or Substrate Utilisation.

The conditional vector of the invention may be used to generate transposon libraries. Such libraries may be screened for mutants affected in solvent production, solvent tolerance, or in substrate utilisation. Two fundamentally different approaches could be adopted:—
(i) a pool of transposon mutants could be generated to allow both the direct selection of mutants able to tolerate higher concentrations of solvent and to determine the identity of non-essential genes
(ii) a library could be created of specific transposon mutants in all non-essential genes that can subsequently be tested using BioLog approaches that are affected in solvent production and substrate utilisation Accordingly, in another preferred embodiment of the invention, there is provided a method of selecting a mutant of a bacterial strain affected in solvent production, tolerance or substrate utilisation, comprising:

(i) providing a library of transposon mutants of the bacterial strain generated through the use of a conditional vector according to the invention; and (ii) selecting for mutants that have altered solvent production, tolerance or substrate utilisation.

Increased solvent tolerance may be selected by selecting individual clones on media containing the solvent of interest.

In a preferred embodiment of the invention, expression of the transposase, if present, is driven by a group 5 RNA polymerase sigma factor and its associated promoter. Preferably, the group 5 RNA polymerase sigma factor is TcdR and its associated promoter is tcdA or tcdB.

The solvent may be acetone, butanol, ethanol, isopropanol, ethylene, butadiene, butanediol or isoprene.

In a further preferred embodiment of the invention, there is provided a mutant bacterial strain affected in solvent production, tolerance or substrate utilisation identified by the method described above.

In another preferred embodiment of the invention, the conditional vector can be used in conjunction with a recently described high throughput random approach, transposon directed insertion-site sequencing (TraDIS), which utilizes nucleotide sequencing to prime from the transposon and sequence into the adjacent target DNA, simultaneously mapping the site of insertion of every transposon in a mutant pool (Langridge et al., 2009. *Genome Res.* 19: 2308-16). TraDIS has previously been used to map 370,000 unique transposon insertion sites to the *Salmonella Typhi* chromosome. The density and resolution of mapped insertion sites (one every 13 bp) has allowed the identification of every essential gene in the genome. Moreover, following growth of the mutant pool in the presence or absence of ox bile, the semi-quantitative nature of the assay led to the identification of genes that contributed to bile tolerance, a trait required for carriage of *S. Typhi*. Thus, the method can be used to simultaneously assay every gene in the genome to identify niche-specific essential genes. One such niche-specific condition is growth in the presence of butanol.

According to another preferred embodiment of the invention, ABI SOLiD 3+ sequencing libraries could be prepared from DNA flanking transposon insertion sites from a solventogenic *Clostridium* species, such as *C. acetobutylicum*, grown in different selective conditions (eg. standard media as well as media supplemented with butanol). Sequence reads could then be matched back to the *Clostridium* genome to identify genes that are non-essential. Genes that are not represented or highly under-represented in each sample of sequences may be candidate essential genes. A total of 20 million mapped sequence tags of 40-50 bp may be generated, representing approximately 15 bp of transposon sequence and 25-35 bp DNA flanking Himar1 C9 insertion sites. The observed distribution and frequency of insertion sites across the genome may be used to identify a list of potentially essential genes and sites under each condition.

The outcome may be two-fold. In the first instance it may allow the identification of genes that cannot be inactivated. This is extremely important as it may identify those genes for which time and effort using directed methods (TargeTron and ClosTron) would be wasted. Secondly, it may identify genes which contribute to solvent tolerance, providing valuable information on the mechanisms currently employed to confer resistance and may provide the basis of rational approaches in enhancing solvent resistance. To identify solvent resistance, the high density library generated through the use of the conditional vector of the present invention may be employed to directly select for mutants that have become more tolerant to solvents (for example, acetone, butanol, ethanol, isopropanol, ethylene, butadiene, butanediol or isoprenel), an important goal in the drive to improve solvent production. Sequencing of the site of insertion of the transposon may further provide valuable information on the mechanisms currently employed to confer resistance and again may provide the basis of rational approaches in enhance solvent resistance.

Another valuable resource is the acquisition of a library of individual mutants comprising individual clones inactivated in every possible gene. Such a library may be generated using the conditional vector of the present invention to express a transposase-encoding nucleic acid. The generated library may then be screened, in a BioLog microtitre format, for those mutations that are affected in such properties as solvent production, solvent tolerance, and substrate utilization. Such information may be extremely valuable in considerably increasing the understanding of the metabolic processes responsible for solvent formation and sugar utilization, particularly in terms of regulation.

The skilled person in the art would appreciate that any of the preferred features according to any aspect of the invention may be applied to any other aspect of the invention described.

Preferred embodiments of the present invention will now be described, merely by way of example, with reference to the following drawings and examples.

FIG. 1—shows a schematic view, and the nucleotide sequence (SEQ ID NO: 16), of the IPTG inducible expression vector pMTL-YZ006.

Key: ermB, the macrolide-lincosamide-streptogramin B antibiotic resistance gene of plasmid pAMβ1; repH, replication region of the *Clostridium butyricum* plasmid pCB102; catP, encoding chloramphenicol acetyltransferase, isolated from plasmid pC194; Pfac, the promoter of the *Clostridium pasteurianum* ferredoxin gene derivatised to include an *E. coli* lac operator; traJ, transfer function of the RP4 oriT region; Pptb, the promoter of the *Clostridium beijerinckii* gene encoding phosphotransbutyrylase; LacI, the *E. coli* gene encoding LacI repressor; ColE1, the replication origin of plasmid ColE1, and; bla, the pBR322 gene encoding beta-lactamase FIG. 2—shows a schematic view, and the nucleotide sequence (SEQ ID NO: 19), of the IPTG inducible expression vector pMTL-YZ007.

Key: T2, a transcriptional terminator isolated from downstream of the *Clostridium difficile* strain 630 CD0164 gene; LacI, the *E. coli* gene encoding LacI repressor; Pptb, the promoter of the *Clostridium beijerinckii* gene encoding phosphotransbutyrylase; Pfac, the promoter of the *Clostridium pasteurianum* ferredoxin gene derivatised to include an *E. coli* lac operator; catP, encoding chloramphenicol acetyltransferase, isolated from plasmid pC194; T1, transcriptional terminator of the ferredoxin gene of *Clostridium pasteurianum*; repH, replication region of the *Clostridium butyricum* plasmid pCB102; ermB, the macrolide-lincosamide-streptogramin B antibiotic resistance gene of plasmid pAMβ1; ColE1, the replication origin of plasmid ColE1, and; traJ, transfer function of the RP4 oriT region.

FIG. 3—shows a schematic view, and the nucleotide sequence (SEQ ID NO: 20), of the lac-based, IPTG inducible expression cassette.

Key: LacI is the LacI repressor protein gene. LacI binds to the indicated lacO region, blocking transcription from the $P_{fac}$ promoter. The −35 and −10 regions of the $P_{fac}$ promoter are underlined in the illustrated sequence. The P$_{ptb}$ promoter (derived from the *Clostridium beijerinckii* gene encoding phosphotransbutyrylase) directs the transcription of the LacI gene.

FIG. 4—shows IPTG induction of CAT production in cells harbouring pMTL-YZ007. Triangles equate to cells which received no IPTG, squares represents samples from cells that were induced with IPTG. Activity is expressed as units of CAT activity per mg or soluble protein.

FIG. 5—shows a schematic view, and the nucleotide sequence (SEQ ID NO: 21), of the Non-Conditional vector pMTL-YZ008.

Key: LacI, the *E. coli* gene encoding LacI repressor; Pptb, the promoter of the *Clostridium beijerinckii* gene encoding phosphotransbutyrylase; Pfac, the promoter of the *Clostridium pasteurianum* ferredoxin gene derivatised to include an *E. coli* lac operator; T1, transcriptional terminator of the ferredoxin gene of *Clostridium pasteurianum*; repH, replication region of the *Clostridium butyricum* plasmid pCB102; ermB, the macrolide-lincosamide-streptogramin B antibiotic resistance gene of plasmid pAMβ1; ColE1, the replication orig replication origin of plasmid ColE1, and; traJ, transfer function of the RP4 oriT region.

FIG. 16—shows a schematic view, and the nucleotide sequence (SEQ ID NO: 30), of the Conditional mariner Transposon Vector pMTL-YZ013.

Key: LacI, the *E. coli* gene encoding LacI repressor; Pptb, the promoter of the *Clostridium beijerinckii* gene encoding phosphotransbutyrylase; Pfac, the promoter of the *Clostridium pasteurianum* ferredoxin gene derivatised to include an *E. coli* lac operator; T1, transcriptional terminator of the ferredoxin gene of *Clostridium pasteurianum*; repH, replication region of the *Clostridium butyricum* plasmid pCB102; ermB, the macrolide-lincosamide-streptogramin B antibiotic resistance gene of plasmid pAMβ1; ColE1, the replication origin of plasmid ColE1; traJ, transfer function of the RP4 oriT region; IR1 & IR2, inverted repeat regions flanking the mini-transposon element; T1, transcriptional terminator of the *Clostridium pasteurianum* ferredoxin gene; catP, a *Clostridium perfringens*-derived gene encoding chloramphenicol acetyltransferase, Himar1 C9, mariner transposase gene, and; po, the promoter region of the *Clostridium difficile* tcdB gene.

FIG. 17—shows a schematic view, and the nucleotide sequence (SEQ ID NO: 31), of the plasmid pMTL-ME6c Key: LHA, left hand homology arm encompassing a foreshortened *Clostridium acetobutylicum* pyrE gene lacking its first 13 codons; LacZ', incorporating multiple cloning sites; T1, transcriptional terminator of the *Clostridium pasteurianum* ferredoxin gene; RHA, right hand homology arm composed of 1200 bp from immediately downstream of the *Clostridium acetobutylicum* pyrE gene, encompassing the hydA gene, CAC0028; RepL, the replication protein of plasmid pIM13; catP, a *Clostridium perfringens*-derived gene encoding chloramphenicol acetyltransferase, and; ColE1, the replication origin of plasmid ColE1.

FIG. 18—shows a schematic representation of the genome of *Clostridium acetobutylicum* strain CRG3011. A promoter-less copy of the tcdR gene (including its ribosome binding site, RBS) of *Clostridium difficile* strain 630 has been inserted into the genome using ACE technology immediately downstream of the pyrE gene (CAC0027). Illustrated are the surrounding genes, and the position of the promoter responsible for expression of tcdR, and the position of the tcdR RBS. The illustrated terminator is the T1 transcriptional terminator of the *Clostridium pasteurianum* ferredoxin gene.

FIG. 19—shows agarose gel electrophoresis of the inverse PCR DNA fragments generated from the chromosome of 31 randomly selected putative transposon mutants. Genomic DNA from 31 individual transposon mutants was isolated and digested with HindIII restriction endonuclease and the resultant DNA circularised by subsequent incubation with T4 DNA ligase. Lane M, Molecular Weight marker; lane C, wild-type *C. acetobutylicum* CRG3011, and; lanes 1 to 31, pMTL-YZ013-derived Thiamphenicol resistant clones 1 to 31.

FIG. 20—shows the location of the different transposon insertions around the *Clostridium acetobutylicum* ATCC 824 genome. Twenty-five independent transposon insertions were sequenced. Insertions in the plus orientation are marked on the circle exterior. Insertions in the minus orientation are marked on the circle interior. Numbers indicate the precise point of insertion according to genome sequence data for *C. acetobutylicum* ATCC 824 (GenBank Accession Number AE001437.1)

FIG. 21—shows the stability of pMTL-YZ008 and pMTL-YZ009 in the presence of IPTG. Transformed cells of *Clostridium sporogenes* NCIMB 10696 containing either pMTL-YZ008 or pMTL-YZ009 were plated at serial dilutions onto TYG agar with and without IPTG (1 mM) and the Colony Forming Units (CFU) estimated.

FIG. 22—shows the stability of pMTL-YZ008 and pMTL-YZ009 in the presence of IPTG. Transformed cells of *Clostridium botulinum* ATCC 3502 containing either pMTL-YZ008 or pMTL-YZ009 were plated at serial dilutions onto TYG agar with and without IPTG (1 mM) and the Colony Forming Units (CFU) estimated.

FIG. 23—shows agarose gel electrophoresis of the inverse PCR DNA fragments generated from the chromosome of 16 randomly selected putative transposon mutants in *Clostridium sporogenes* strain CRG3844. Genomic DNA from 16 individual transposon mutants was isolated and digested with HindIII restriction endonuclease and the resultant DNA circularised by subsequent incubation with T4 DNA ligase. Lane M, Molecular Weight marker; lanes 1 to 16, pMTL-YZ013-derived Thiamphenicol resistant transposon mutant clones 1 to 16.

CONSTRUCTION OF AN INDUCIBLE EXPRESSION CASSETTE BASED ON A LAC OPERATOR

An IPTG-inducible expression system has previously been described (Heap J T et al., *Journal of Microbiological Methods,* 2007, 703: 452-64), and forms part of the plasmid pMTL5401Fcat as described therein. Plasmid pMTL5401Fcat was modified so that the promoter of the *Clostridium pasteurianum* ferredoxin included a lac operator sequence, inserted immediately downstream of the +1 transcriptional initiation site. Transcription from this promoter (termed the $P_{fac}$ promoter) could be repressed by the presence of the LacI protein, which was produced from a vector-borne copy of the lacI gene, which had been placed under the transcriptional control of the $P_{ptb}$ promoter of the *Clostridium beijerinckii* phosphotransbutyrylase gene (ptb). In vector pMTL5401Fcat, a promoter-less copy of the pC194 cat gene encoding chloramphenicol acetyltransferase (CAT) was placed downstream of the $P_{fac}$ promoter. Production of CAT was therefore induced in cells harbouring pMTL5401Fcat when IPTG was added.

In order to test the ability of this inducible promoter system to control the replication of a plasmid, the control of the expression of the plasmid replication region was tested. That is replication would be dependent on the presence of IPTG (the permissive condition) and then transference of the cells to media lacking inducer (the non-permissive condition) would result in a cessation of plasmid replication and therefore plasmid loss.

To test this hypothesis, it was desirable to locate the inducible system to a portable cassette which may be an inducible expression cassette comprising an inducible promoter that could be subsequently positioned 5' to the plasmid replication region of any particular plasmid replication region. In vector pMTL5401Fcat, the ptb::lacI element and the $P_{fac}$ promoter were physically separated by a gene encoding the transfer function traJ and oriT sequence. As the presence of this gene and oriT region was not necessary, a strategy was devised whereby traJ was removed. Accordingly, a deletion was made between position 4058 bp and 5040 bp of pMTL5041Fcat using QuikChange II Site-Directed Mutagenesis Kit (Stratagene).

Primers del (5'-CTCGATCCGGGGAATTCTCTGCA-GATAATTCAGGG-3') (SEQ ID NO: 14) and del-antisense (5'-CCCTGAATTATCTGCAGAGAATTCCCCGGATC- GAG-3') (SEQ ID NO:15) were designed, and PCR reactions were carried out according to manufacturer's instructions. PCR products were digested by enzyme DpnI to eliminate template plasmids at 37° C. for an hour, and then transformed into E. coli XL-1 Blue. Plasmids extracted from E. coli XL-1 Blue were confirmed via Sanger Sequencing. The resulting plasmid was designated pMTL-YZ006 as shown in FIG. 1 (SEQ ID NO:16).

Following deletion of the traJ region, the lac inducible promoter cassette ($P_{ptb}$::lacI element and the $P_{fac}$ promoter) was then PCR amplified using primers YZ4 (5'-TT-TATATAGCGGCCGCGCTCACTGCCCGCTTT-3') (SEQ ID NO:17) and YZ35 (5'-GTGCCAAGCTTGCATGC-CATGGTA-3') (SEQ ID NO: 18) (which included the emboldened restriction enzyme recognition sites 5'-GCG-GCCGC-3' and 5'-AAGCTT-3', respectively). The amplified DNA fragment was cleaved with Not I and Hind III and the sticky-end fragment generated cloned into pMTL83251 as described in (Heap et al., Journal of Microbiological Methods, 2009, 78: 79-85) between the NotI and HindIII sites. The plasmid created was designated pMTL-YZ007 as shown in FIG. 2 (SEQ ID NO:19). A schematic diagram of the inducible expression cassette is shown in FIG. 3, and its complete nucleotide sequence corresponds to SEQ ID NO:20.

In order to test that the inducible system was still functioning as expected, plasmid pMTL-YZ007 was transformed into Clostridium acetobutylicum ATCC 824 and cells anaerobically cultivated at 37° C. in 25 ml of CGM medium (Hartmanis M G N and Gatenbeck S, 1984, Applied Environmental Microbiology, 47: 1277-1283) supplemented with erythromycin (40 μg per ml). Two duplicate cultures were set up. Cells were grown to an $OD_{600}$ of 0.6 at which point IPTG was added to one culture (final concentration 1 mM), whereas the duplicate culture received no inducer. Cultivation of the culture continued, and 2 ml samples were withdrawn at regular intervals followed by centrifugation and resuspension of cell pellet in 1 ml 100 mM Tris-HCl (pH 7.8). Cell lysate was achieved by sonication, and the level of expression of CAT determined according to the method of Shaw (Shaw, W. V., 1975, Methods in Enzymology, 43:737-755). The assay mixture contained 100 mM Tris-HCl (pH 7.8), 0.1 mM acetyl-coenzyme A and 0.4 mg 5,5'-dithiobis-2-nitrobenzoic acid (DTNB)/ml, and was equilibrated to 37° C. before use. Cell lysate (10 μl) and 5 mM chloramphenicol in 100% ethanol (10 μl) were added to 980 μl assay mixture in a plastic cuvette and the Absorption at 412 nm was measured for 1 min using an AnalytikJena Specord 250 spectrophotometer. Protein concentration of cell lysate was determined by Thermo Scientific NanoDrop 2000 Spectrophotometer.

The level of CAT expression achieved in the two cultures is shown in FIG. 4. These data clearly show that IPTG induction of CAT production is occurring in cells carrying plasmid pMTL-YZ007.

Derivation of a pCB102-Based Conditional Vector, pMTL-YZ009, Using the $P_{fac}$-Based Inducible Promoter Having established the functionality of the $P_{fac}$ inducible promoter, the catP gene was deleted from plasmid pMTL-YZ007, in order to bring the pCB102 plasmid replication region under the transcriptional control of $P_{fac}$. Two plasmids were created. In the one (pMTL-YZ008 as shown in FIG. 5, SEQ ID NO:21), pMTL-YZ007 was cleaved with BamHI and HindIII, the sticky-ends created blunt-ended by treatment with T4 polymerase, and the resultant linear fragment subjected to self-ligation. In a second plasmid (pMTL-YZ009, as shown in FIG. 6, SEQ ID NO: 22) pMTL-YZ007 was digested with BamHI and AscI, the sticky-ends created blunt-ended by treatment with T4 polymerase, and the resultant linear fragment subjected to self-ligation.

The essential difference between the two plasmids is that pMTL-YZ008 carries a transcriptional terminator (that of the ferredoxin gene of Clostridium pasteurianum) between the $P_{fac}$ promoter and the repH replication gene of the pCB102 plasmid replication region. This terminator was deleted in pMTL-YZ009.

Figure 7:
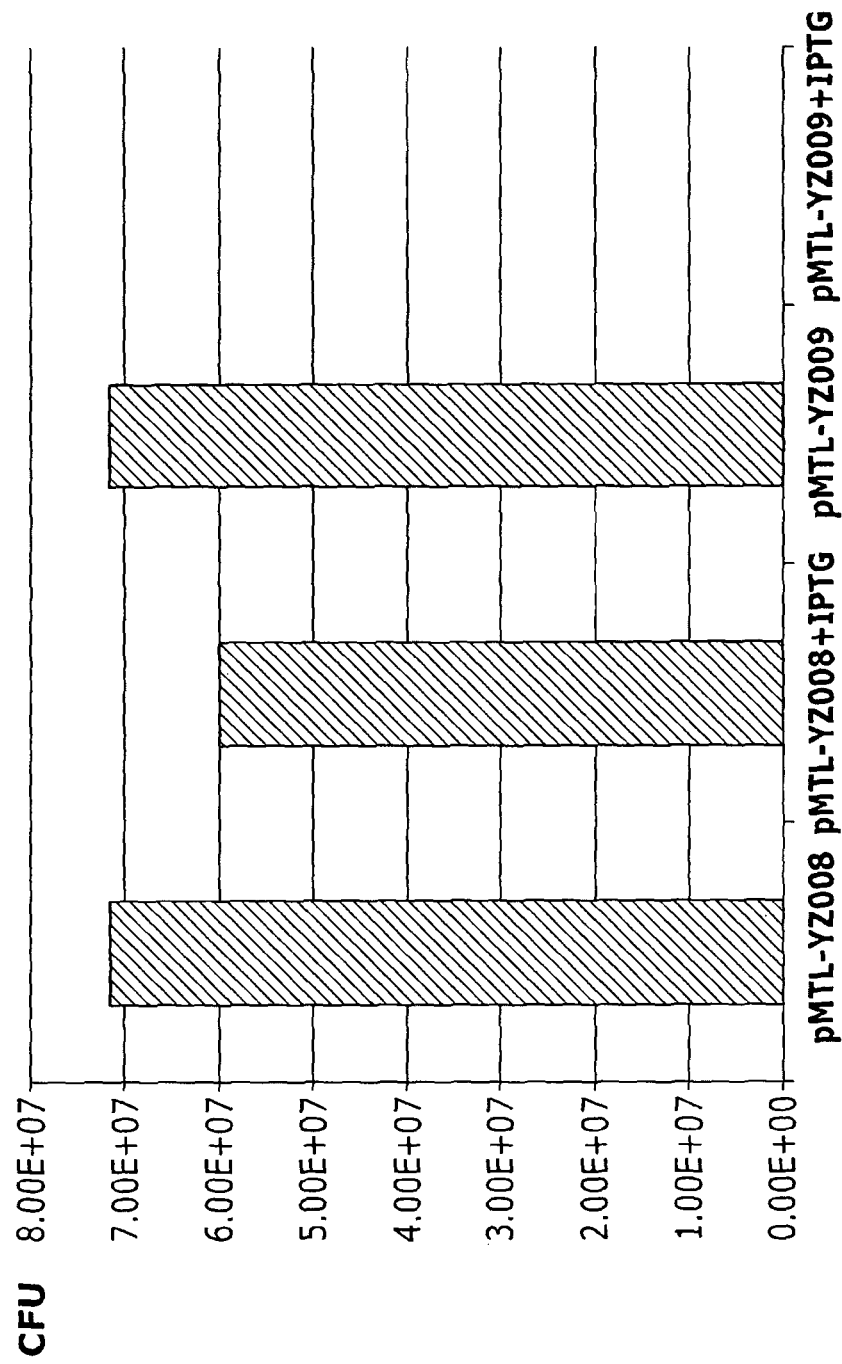
Figure 8:
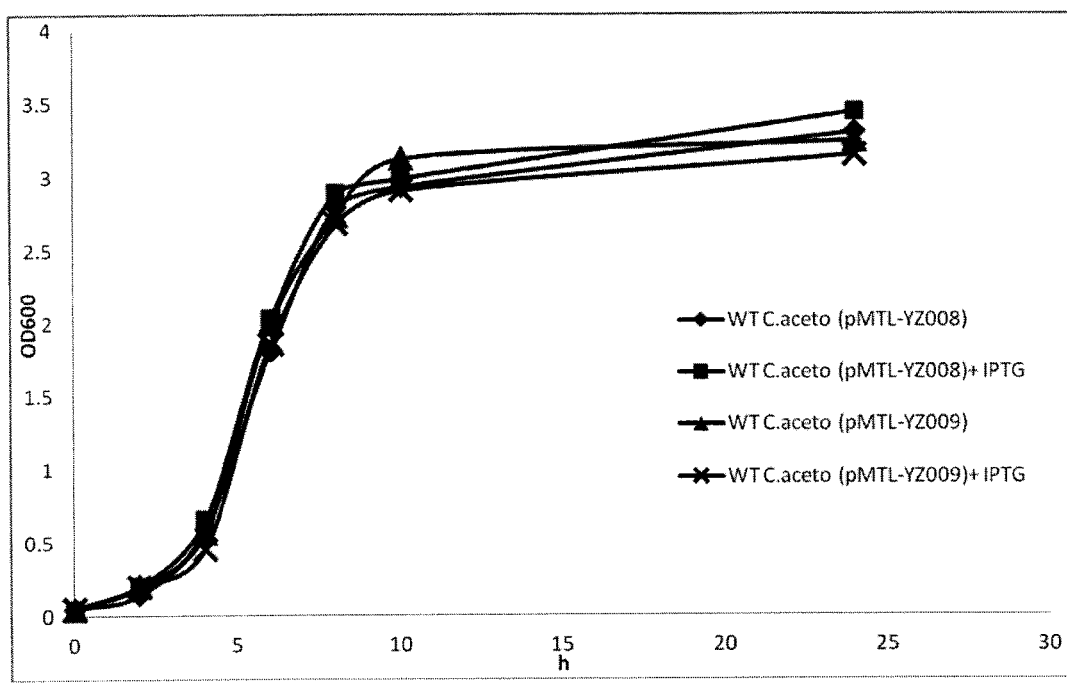

The two plasmids were introduced by electroporation into Clostridium acetobutylicum ATCC 824 and their ability to replicate tested in the presence or absence of the inducer IPTG in CGM media lacking any antibiotic supplementation. Unexpectedly, plasmid pMTL-YZ009 was found to only be stably maintained in the absence of IPTG as shown in FIG. 7. In the presence of IPTG (1 mM), the plasmid was rapidly lost as shown in FIG. 7, as evidenced by an almost complete loss of Colony Forming Units (CFU) on plates supplemented with erythromycin (40 μg per ml). A similar loss was not evident in cells harbouring pMTL-YZ008 (FIG. 13). It was concluded that transcriptional readthrough into the pCB102 plasmid replication region was interfering with plasmid replication/maintenance.

Construction of an Inducible Expression Cassette Based on a Tet Operator

In parallel, an equivalent system was constructed based on the Tet system. The system is broadly equivalent to the lac system. Thus the promoter of the tetA gene contains an operator sequence to which the TetR (equivalent to LacI) repressor protein binds. Repression is lifted through binding of tetracycline antibiotic (Tc) to TetR, which causes a conformational change, releasing it from the operator sequence. As Tc can inhibit growth, the Tc analogue anhydrotetracycline (aTc) is commonly used as a replacement. It has higher affinity for TetR compared to Tc, but has a decreased toxicity.

This system has been used in a number of bacteria, including mycobacteria and staphylococcus (Corrigan, R. M. & Foster, T. J. 2009 Plasmid 61, 126-129; Ehrt, S. et al., 2005 Nucleic Acids Res 33, e21, doi:10.1093/nar/gni013). To develop an equivalent system for Clostridia, it was elected to derivatise the $P_{fdx}$ promoter of the Clostridium sporogenes ferredoxin gene through the incorporation of the requisite Tet operator sequence. Accordingly, we designed and had synthesised a prototype system, based loosely on the system described previously Corrigan, R. M. & Foster, T. J. 2009. Plasmid 61, 126-129. A schematic of the cassette constructed is shown in FIG. 9 (SEQ ID NO: 23). It comprises a TetR gene under the control of the $P_{thl}$ promoter of the Clostridium acetobutylicum thiolase gene (thl), a derivatised $P_{fdx}$ promoter of the Clostridium sporogenes ferredoxin gene and a TetR gene that encodes the same TetR protein as that carried by the E. coli plasmid R100 (GenBank Accession NC_002134.1), but the codons have been altered to match those generally found in Clostridium difficile.

The 1249 bp synthetic sequence was introduced into the modular vector pMTL82254 (Heap et al., Journal of Microbiological Methods, 2009, 78: 79-85) as an NdeI—NotI restriction fragment between the equivalent sites of pMTL82254 to yield the plasmid pMTL-tet3nO (FIG. 10, SEQ ID NO: 24). Plasmid pMTL82254 carries a promoter-less copy of the catP gene isolated from Clostridium perfringens. Accordingly, the inducible cassette was inserted such that the $P_{fet}$ promoter was positioned immediately upstream of this gene. To test the functionality of the inducible system, plasmid pMTL-tet3nO was transformed into *Clostridium difficile* strain 630 and cells anaerobically cultivated at 37° C. in 100 ml of BHIS medium (brain heart infusion media supplemented with yeast extract [5 mg/ml, Oxoid]) supplemented with erythromycin (10 µg per ml). Two duplicate cultures were set up. Cells were grown to an $OD_{600}$ of 0.6 at which point aTc was added to one culture (final concentration 316 ng per ml), whereas the duplicate culture received no inducer. Cultivation of the culture continued, and samples were withdrawn at regular intervals. At each time point, sample culture was normalized to a 10 ml equivalent of $OD_{600}$ 1.0, followed by centrifugation and resuspension of cell pellet in 1 ml 100 mM Tris-HCl (pH 7.8). Cell lysate was achieved by sonication, and the level of expression of CAT determined according to the method of Shaw (Shaw, W. V. 1975, *Methods in Enzymology*, 43:737-755.). The assay mixture contained 100 mM Tris-HCl (pH 7.8), 0.1 mM acetyl-coenzyme A and 0.4 mg 5,5'-dithiobis-2-nitrobenzoic acid (DTNB)/ml, and was equilibrated to 37° C. before use. Cell lysate (10 µl) and 5 mM chloramphenicol in 100% ethanol (10 µl) were added to 980 µl assay mixture in a plastic cuvette and the Absorption at 412 nm was measured for 1 min using an AnalytikJena Specord 250 spectrophotometer.

Figure 11:
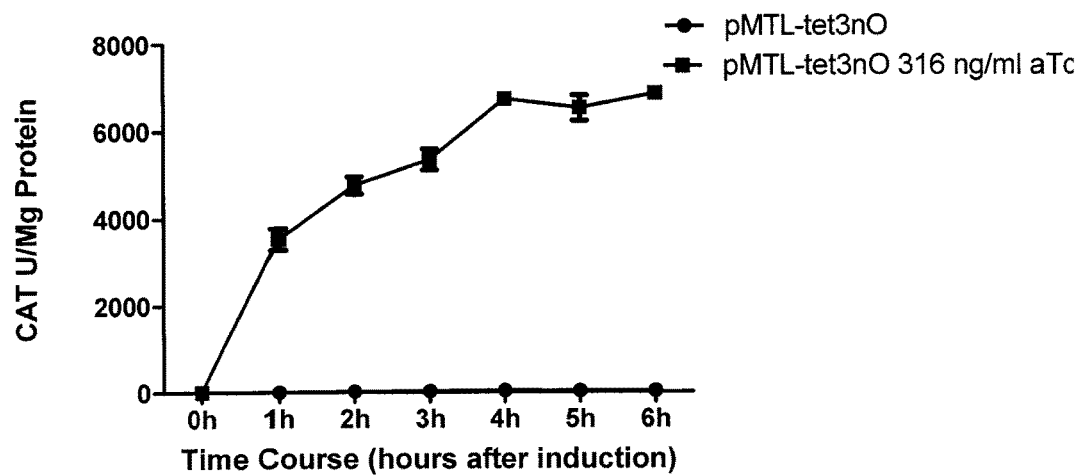

The level of CAT expression achieved in the two cultures is shown in FIG. 11. The data show that aTc induction of CAT production is occurring in cells carrying plasmid pMTL-tet3nO, and establishes that the system is functional.

Derivation of a pCB102-Based Conditional Vector, pMTL-YZ011, Using the $P_{fet}$-Based Inducible Promoter Having demonstrated that the $P_{fac}$ promoter could be used to control plasmid replication based on the pCB102 plasmid replication region, it was determined whether the $P_{fet}$ promoter could be similarly employed. This is important, because the $P_{fac}$ promoter might not be applicable to all members of the Class Clostridia. Indeed, the lac system does not function in *Clostridium difficile*, most likely due to failure of the IPTG inducer to enter the cell.

An equivalent plasmid to pMTL-YZ008 was therefore made in which the $P_{fac}$-based inducible expression cassette was replaced with the $P_m$-based inducible expression cassette. This was accomplished by isolating the $P_{fet}$ promoter/$P_{thl}$::tetR cassette as a 1249 bp fragment from plasmid pMTL-tet3nO following cleavage with NotI and NdeI. Plasmid pMTL-YZ008 was then cleaved with the same enzymes, excising the $P_{fac}/P_{ptb}$::lacI cassette, allowing the $P_{fet}$ promoter/$P_{thl}$::tetR cassette to be inserted in its place. The plasmid created was designated pMTL-YZ010 (FIG. 12, SEQ ID NO: 25). In common with pMTL-YZ008, the *Clostridium pasteurianum* Fd terminator is positioned between the inducible promoter and the pCB102 plasmid replication region. In parallel, and equivalent vector to pMTL-YZ009 was made (plasmid pMTL-YZ011, FIG. 13, SEQ ID NO: 26) in which the same cloning strategy was used to replace the $P_{fac}/P_{ptb}$::lacI cassette with the $P_{fet}/P_{thl}$::tetR using the NotI and NdeI restriction sites. It follows that in pMTL-YZ011, there is no transcriptional terminator between the $P_{fet}$ promoter and the pCB102 plasmid replication region.

Figure 14:
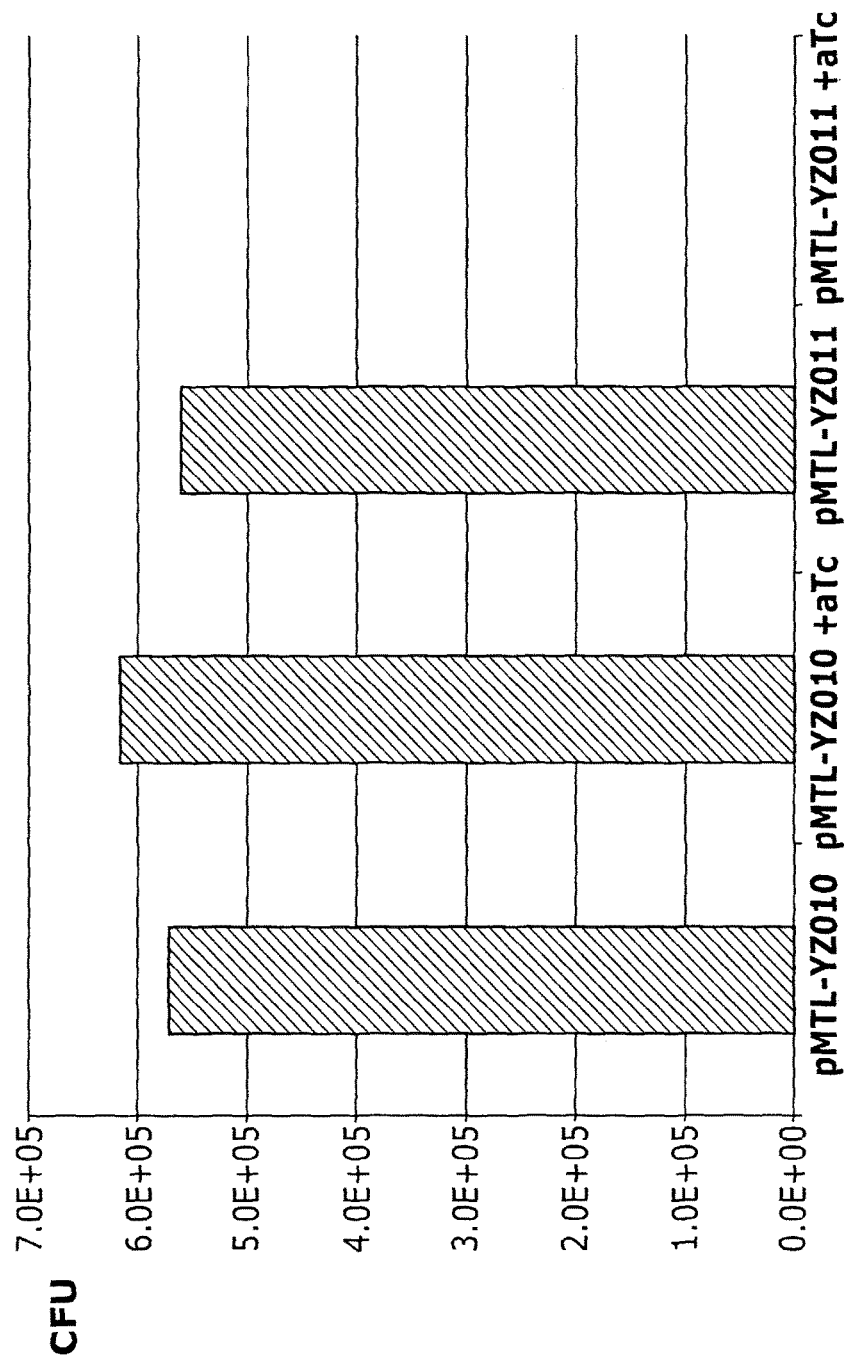

The two plasmids were introduced by conjugation (Purdy D et al., 2002, *Molecular Microbiology*, 46: 439-52) into *Clostridium difficile* strain 630 and their ability to replicate tested in the presence or absence of the inducer aTc in BHIS medium (brain heart infusion media supplemented with yeast extract [5 mg/ml, Oxoid]). In keeping with the result with pMTL-YZ009, plasmid pMTL-YZ011 was found to only be stably maintained in the absence of aTc. In the presence of aTc (200 ng per ml), the plasmid was rapidly lost, as evidenced by an almost complete loss of CFU on plates supplemented with erythromycin (10 µg per ml). A similar loss was not evident in cells harbouring pMTL-YZ010. As demonstrated in FIG. 14, the data confirmed that transcriptional readthrough into the pCB102 plasmid replication region interferes with plasmid replication/maintenance.

Use of the Conditional Vector, pMTL-YZ013, for Transposon Delivery

The inducer-mediated loss of plasmids such as pMTL-YZ009 and pMTL-YZ011 from Clostridial cells could potentially allow the conditional delivery of a transposon element. To test this possibility, a derivative of the mariner transposon vector pMTL-SC1 (Cartman S T and Minton N P, 2010, *Applied Environmental Microbiology*, 76: 1103-1109) was constructed. To achieve this, a conditional replicon cassette was constructed, essentially by locating the $P_{fac}/P_{ptb}$::lacI cassette plus the pCB102 plasmid replication region to a portable AscI-FseI fragment suitable for incorporation into the pMTL80000 modular format (Heap J. T. et al, 2009, *Journal of Microbiological Methods*, 78: 79-85). To achieve this, the NotI site of pMTL-YZ008 was changed to an AscI site using QuikChange II Site-Directed Mutagenesis Kit (Stratagene), to yield the plasmid pMTL-YZ012 (FIG. 15, SEQ ID NO: 27). Briefly, primers NotI/AscI, SEQ ID NO: 28 (5'-aacagctatgaccggcgcgccgctcactgcccgc-3') and NotI/AscI antisense, SEQ ID NO:29 (5'-gcgggcagtgagcg-gcgcgccggtcatagctgtt-3') were designed, and PCR reactions were carried out according to manufacturer's instructions. PCR products were digested by enzyme DpnI to eliminate template plasmids at 37° C. for an hour, and then transformed into *E. coli* XL-1 Blue. Plasmids extracted from *E. coli* XL-1 Blue were confirmed via Sanger Sequencing. Thereafter, a 3543 bp AscI-FseI fragment was isolated from pMTL-YZ012 and inserted between the equivalent sites of pMTL-SC1. This essentially replaced the pBP1-based replicon of pMTL-SC1 with the new conditional replicon cassette. The plasmid generated was designated pMTL-YZ013 (FIG. 16, SEQ ID NO: 30).

Figure 18:
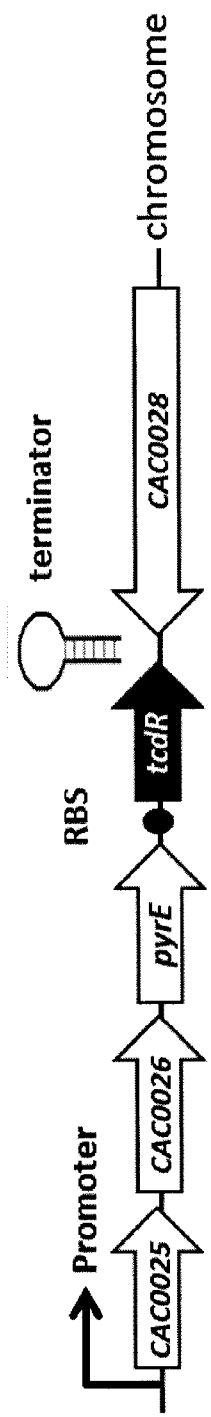

The mariner transposon system carried by pMTL-SC1 was specifically adapted to function in the pathogen *C. difficile*. Thus, the transposase gene is expressed by the promoter of the Toxin B (tcdB) gene. One benefit of the use of this promoter is that it does not function in the donor *E. coli* host, as it is only recognised by a specific *C. difficile* sigma factor. However, for the transposon to work in a clostridial host other than *C. difficile*, the TcdR sigma factor needs to be present. In order to achieve this a strain of *Clostridium acetobutylicum* ATCC 824 was generated in which a promoter-less copy of the tcdR gene of *Clostridium difficile* 630 was inserted into the genome immediately downstream of the pyrE gene using Allele-Couple Exchange (ACE) Technology. This was accomplished using the described procedures (Heap et al, *Nucleic Acids Research*, 2012 40(8): e59) and the vector pMTL-ME6c (FIG. 17, SEQ ID NO: 31). The strain generated was designated *Clostridium acetobutylicum* CRG3011 (FIG. 18).

Plasmid pMTL-YZ013 was transformed into strain CRG3011, and the transformed cells plated on CGM agar (Hartmanis M G N and Gatenbeck S, 1984, *Applied Environmental Microbiology*, 47: 1277-1283) containing erythromycin (40 µg per ml). Cells were harvested and plated on CGM agar containing thiamphenicol (15 µg per ml) and IPTG (1 mM). In total, 80% of colonies were thiamphenicol resistant and erythromycin sensitive, indicative of successful insertion of the catP mini-transposon into chromosome and plasmid loss.

Figure 19:
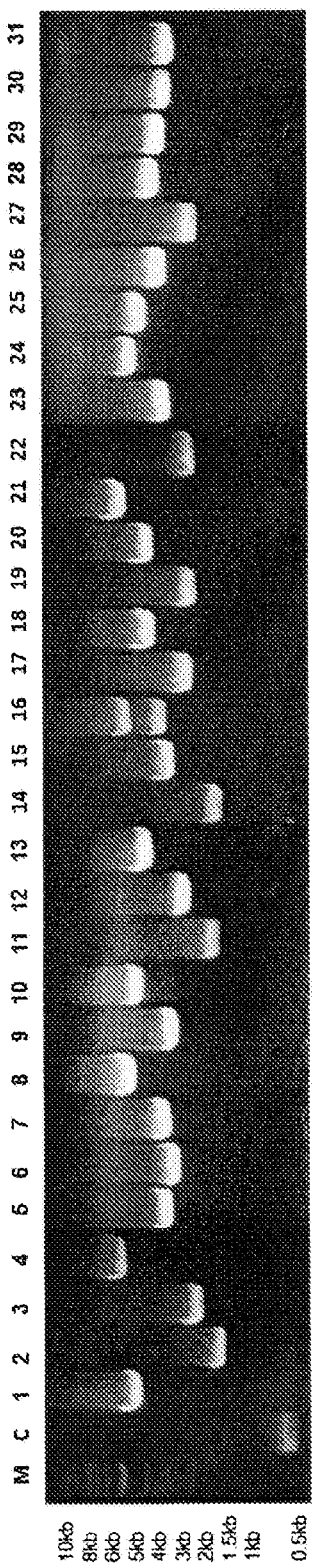
Figure 20:
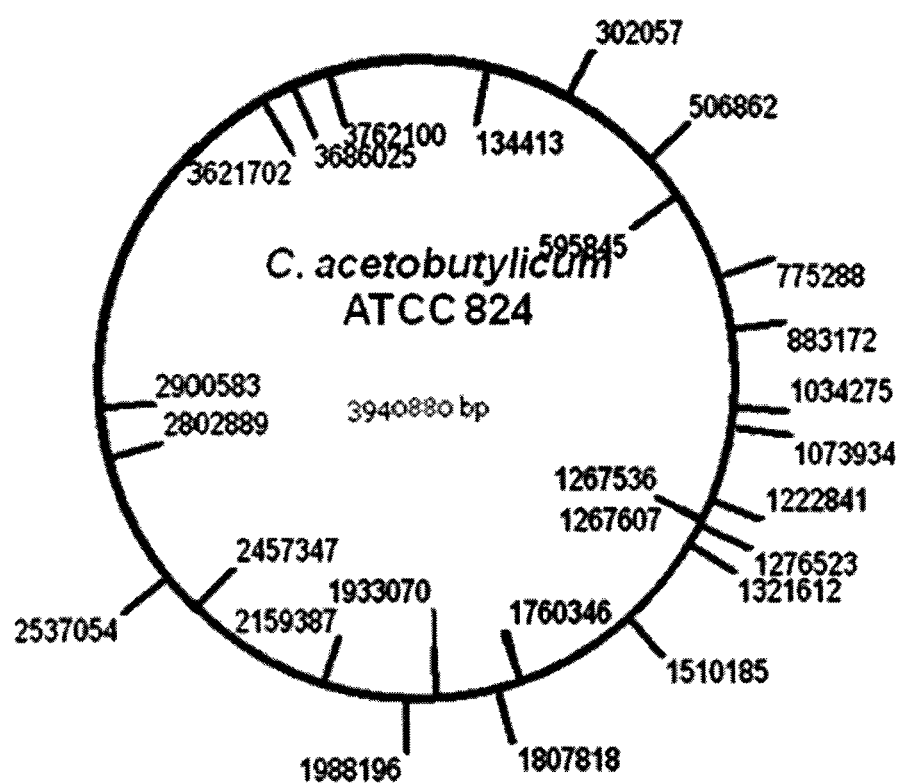

To establish whether transposition had occurred, inverse PCR was performed according to the procedure of Cartman and Minton (Cartman S T and Minton N P, 2010, *Applied Environmental Microbiology*, 76: 1103-1109). Genomic DNA was isolated from individual transposon mutants and digested overnight with HindIII at a concentration of 200 ng/µl. The HindIII restriction endonuclease was heat inactivated (65° C. for 30 min), and DNA was diluted to a concentration of 5 ng/µl in a reaction with T4 DNA ligase to favor self-ligation (and thus circularization) of restriction fragments. Ligation reaction mixtures were incubated at ambient temperature for 1 h, and then the T4 ligase was heat inactivated (65° C. for 30 min). Inverse PCRs were carried out in 50-µl volumes using the KOD Hot Start DNA polymerase Master Mix kit (Novagen), with 100 ng of ligated DNA and primers catP-INV-F1 (5'-TAAATCATTTT-TAGCAGATTATGAAAGTGATACGCAACGGTATGG-3') (SEQ ID NO:32) and catP-INV-R1 (5'-TATTG-TATAGCTTGGTATCATCTCATCATATATCCCCAATTC ACC-3') (SEQ ID NO: 33), which face out from the transposon-based catP sequence. Inverse PCR products were run out on a 0.8% (wt/vol) agarose gel as shown in FIG. 19), purified with the QIAquick gel purification kit (Qiagen), and sequenced using the primer catP-INV-R2 (5'-TATTTGTGT-GATATCCACTTTAACGGTCATGCTGTAGGTA-CAAGG-3') (SEQ ID NO: 34). To identify the genomic location of transposon insertions, sequence data were analyzed using GENtle open source software. The data revealed that each transposon insertion had taken place at a different position around the genome as illustrated in FIG. 20.

In parallel, CRG3011 cells were also transformed with unadulterated pMTL-SC1, and selected transformants selected on rich media containing erythromycin (40 µg per ml). Cells were harvested and plated on CGM agar containing thiamphenicol (15 µg per ml). A total of 24 thiamphenicol resistant colonies were picked and re-streaked 3 times, only 2 of them became erythromycin sensitive, indicative of plasmid loss. These results suggested that the plasmid replication region of pMTL-SC1 is very stable in *C. acetobutylicum* host, which is not ideal for transposon mutagenesis.

Demonstration of Conditional Vector, pMTL-YZ009, in *Clostridium sporogenes*

Figure 21:
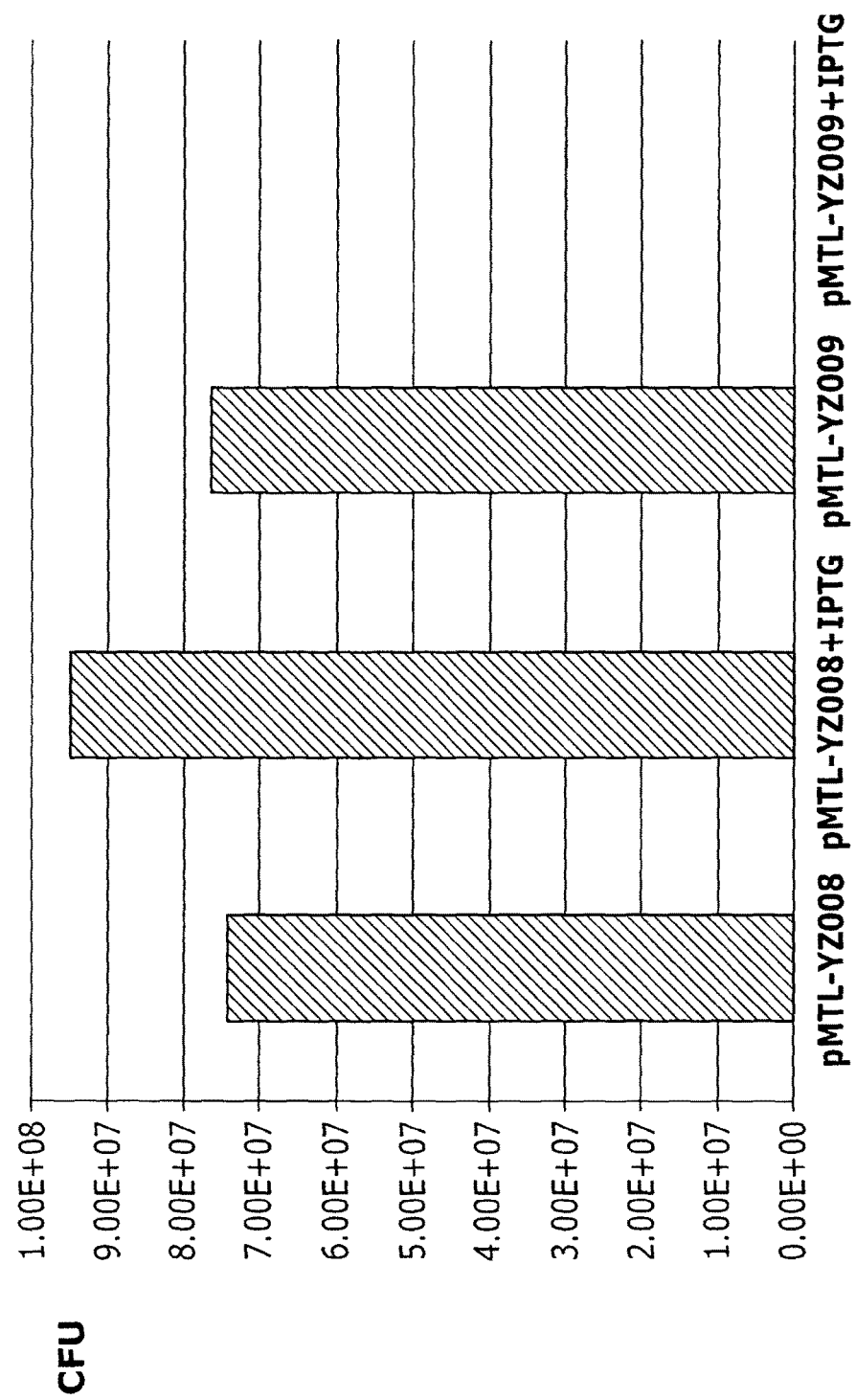

To test the conditionality of plasmid pMTL-YZ009 (FIG. 6, SEQ ID NO: 22), plasmids pMTL-YZ008 (FIG. 5, SEQ ID NO: 21) and pMTL-YZ009 were introduced by electroporation into *Clostridium sporogenes* NCIMB 10696. Their ability to replicate tested in the presence or absence of the inducer IPTG in TYG media lacking any antibiotic supplementation. As expected, plasmid pMTL-YZ009 was found to only be stably maintained in the absence of IPTG as shown in FIG. 21. In the presence of IPTG (1 mM), the plasmid was rapidly lost as shown in FIG. 21, as evidenced by an almost complete loss of Colony Forming Units (CFU) on plates supplemented with erythromycin (20 µg per ml). A similar loss was not evident in cells harbouring pMTL-YZ008 (FIG. 21). It was concluded that transcriptional readthrough into the pCB102 plasmid replication region was interfering with plasmid replication/maintenance.

Demonstration of Conditional Vector, pMTL-YZ009, in *Clostridium botulinum*

Figure 22:
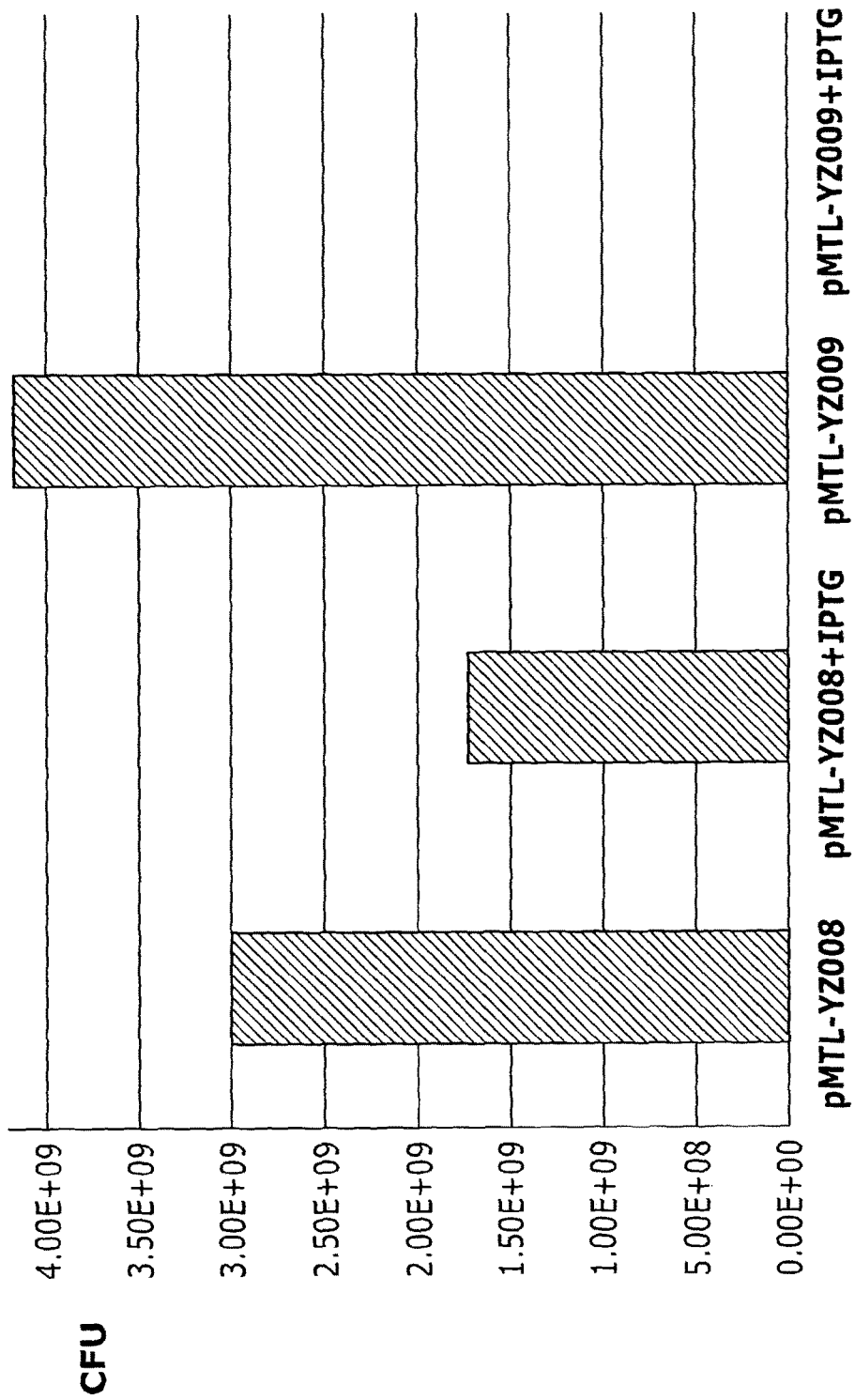

To test the conditionality of plasmid pMTL-YZ009 (FIG. 6, SEQ ID NO: 22), plasmids pMTL-YZ008 (FIG. 5, SEQ ID NO: 21) and pMTL-YZ009 were introduced by electroporation into *Clostridium botulinum* ATCC 3502. Their ability to replicate tested in the presence or absence of the inducer IPTG in TYG media lacking any antibiotic supplementation. As expected, plasmid pMTL-YZ009 was found to only be stably maintained in the absence of IPTG as shown in FIG. 22. In the presence of IPTG (1 mM), the plasmid was rapidly lost as shown in FIG. 22, as evidenced by an almost complete loss of Colony Forming Units (CFU) on plates supplemented with erythromycin (20 µg per ml). A similar loss was not evident in cells harbouring pMTL-YZ008 (FIG. 22). It was concluded that transcriptional readthrough into the pCB102 plasmid replication region was interfering with plasmid replication/maintenance.

Use of the Expression System for Expression of the Transposase Himar1 C9 in *Clostridium sporogenes*

Transposon mutagenesis using the mariner transposon-based transposon vector pMTL-YZ013 (FIG. 16, SEQ ID NO: 30), is reliant on TcdR-mediated expression of the mariner transposase. Accordingly, the introduction of this vector into the *Clostridium sporogenes* strain CRG3817 should result in transposition of the mini-transposon carrying the catP gene and conditional plasmid loss.

To determine whether transposition would occur in strain CGR3817, plasmid pMTL-YZ013 was transformed into *Clostridium sporogenes* strain CRG3817 and transformants selected on TYG plates containing 40 µg/ml erythromycin. Plates carrying greater than 10 isolated, transformant colonies were then incubated at 37° C. for 48 hours. All of the colony growth was scraped from the plate using a sterile loop and the cells resuspended in TYG media containing +20% Glycerol. The cell suspension was then plated at serial dilutions onto TYG agar plates containing 15 µg/ml thiamphenicol and 1 mM IPTG. A total of 100 colonies were then patch plated onto TYG plates containing 15 µg/ml thiamphenicol and TYG plates containing 40 µg/ml erythromycin as a simple test to ascertain whether the plasmid pMTL-YZ013 was still present. All 100 colonies render sensitivity to erythromycin and resistance to thiamphenicol, indicating that under the conditions employed, the plasmids had all been lost and transposition occurred from the population.

Figure 23:
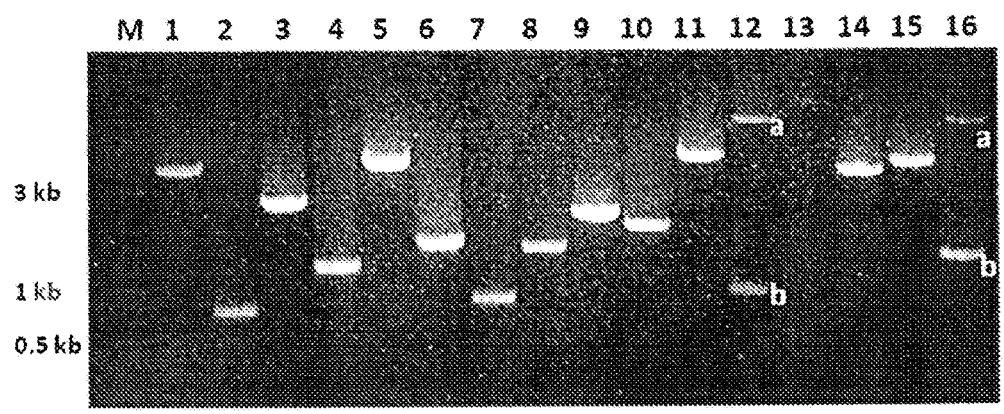

To establish whether transposition had occurred, inverse PCR was performed according to the procedure of Cartman and Minton (Cartman S T and Minton N P *Applied Environmental Microbiology* 2010, 76:1103-9). Genomic DNA was isolated from 16 individual thiamphenicol resistant clones and digested overnight with HindIII at a concentration of 200 ng/µl. The HindIII restriction endonuclease was heat inactivated (65° C. for 30 min), and DNA was diluted to a concentration of 5 ng/µl in a reaction with T4 DNA ligase to favor self-ligation (and thus circularization) of restriction fragments. Ligation reaction mixtures were incubated at ambient temperature for 1 h, and then the T4 ligase was heat inactivated (65° C. for 30 min). Inverse PCRs were carried out in 50-µl volumes using the KOD Hot Start DNA polymerase Master Mix kit (Novagen), with 100 ng of ligated DNA and primers catP-INV-F1, SEQ ID NO: 32 (5'-TAAATCATTTTTAGCAGATTATGAAAGTGATACG-CAACGGTATGG-3') and catP-INV-R1, SEQ ID NO: 33 (5'-TATTGTATAGCTTGGTATCATCTCATCATATATC-CCCAATTCACC-3'), which face out from the transposon-based catP sequence. Inverse PCR products were run out on a 0.8% (wt/vol) agarose gel (FIG. 23), purified with the QIAquick gel purification kit (Qiagen), and sequenced using primer catP-INV-R2 SEQ ID NO: 34 TATTTGTGTGA-TATCCACTTTAACGGTCATGCTGTAGGTACAAGG-3'). To identify the genomic location of transposon insertions, sequence data were analyzed using GENtle.

These data revealed that in all of the colonies tested, the transposon had inserted into 18 different locations within the *Clostridium sporogenes* genome (Table 1.) Two of the 16 clones possess double insertions. These data provide proof of principle that the presence of tcdR in the genome of CRG3817 allows transposition of the mariner transposon in *Clostridium sporogenes*.

TABLE 1

Sequence analysis of the Inverse PCR products from eight randomly selected thiamphenicol resistant colonies carrying pMTL-YZ013.

| Colony Number | Position of Insertion in *C. sporogenes* NCIMB 10696 genome | Gene affected | Gene function |
|---|---|---|---|
| 1 | 2440051 (reverse strand) | CS1546 | pyridine nucleotide-disulfide oxidoreductase family protein |
| 2 | 1827633 (forward strand) | CS1723 | DEAD/DEAH box helicase family protein |
| 3 | 2319672 (forward strand) | CS2157 | KWG leptospira repeat protein |
| 4 | 2960953 (forward strand) | CS2817 | heparinase II/III-like family protein |
| 5 | 3527420 (forward strand) | CS3350 | putative CoA-substrate-specific enzyme activase domain protein |
| 6 | 1682076 (forward strand) | CS1592 | HAD ATPase, P-type, IC family protein |
| 7 | | prfC | found in botulinum not in sporogenes |
| 8 | 1454638 (forward strand) | CS1379 | 4Fe-4S binding domain protein |
| 9 | 842007 (reverse strand) | CS3053 | putative membrane protein |
| 10 | 897474 (reverse strand) | CS3008 | HNH endonuclease family protein |
| 11 | 1028948 (forward strand) | CS0978 and 0979 | conserved hypothetical protein and putative membrane protein |
| 12a | 3297392 (reverse strand) | CS0721 | conserved hypothetical protein |
| 12b | 3065003 (forward strand) | CS2912 | polysaccharide deacetylase family protein |
| 13 | 879201 (forward strand) | CS0821 | 2-amino-4-hydroxy-6-hydroxymethyldihydropteridine pyrophosphokinase |
| 14 | 3443288 (forward strand) | CS3275 | dihydrodipicolinate reductase, family protein |
| 15 | 2768400 (forward strand) | CS1233 and 1234 | L-serine dehydratase, iron-sulfur-dependent, beta subunit and L-serine dehydratase, iron-sulfur-dependent, alpha subunit |
| 16a | 3213733 (reverse strand) | CS0806 | branched-chain amino acid transport system II carrier protein |
| 16b | 1643917 (forward strand) | CS1552 | ftsX-like permease family protein |

The invention claimed is:

1. A conditional vector comprising DNA encoding for:
   (i) a genetically engineered inducible expression cassette comprising an inducible promoter operably linked to a plasmid replication region, wherein the inducible promoter and expression cassette are heterologous, and wherein the plasmid replication region consists of a sequence of SEQ ID NO: 7; and
   (ii) a selectable marker.

2. The conditional vector of claim 1, further comprising a transposable element.

3. The conditional vector of claim 2, wherein the transposable element is the mini-transposon, Himar1C9.

4. The conditional vector of claim 1, further comprising a transposase operably linked to a promoter.

5. The conditional vector of claim 1, wherein the inducible promoter is selected from a $P_{fac}$, $P_{fet}$ or $P_{xylA}$ promoter.

6. The conditional vector of claim 1, wherein the selectable marker encodes resistance to erythromycin, tetracycline, spectinomycin or thiamphenicol.

7. The conditional vector of claim 1, further comprising a group 5 RNA polymerase sigma factor.

8. The conditional vector of claim 7, further comprising a promoter recognised by the group 5 RNA polymerase sigma factor.

9. The conditional vector of claim 7, wherein the group 5 RNA polymerase sigma factor is TcdR.

10. The conditional vector of claim 8, wherein the promoter recognised by the group 5 RNA polymerase sigma factor is tcdA or tcdB.

11. A method of delivering a transposon into a bacterial host genome comprising introducing the conditional vector of claim 1 into a bacterial cell.

12. A method of delivering a transposon into Clostridia comprising contacting the conditional vector of claim 1 to Clostridia.

13. A bacterial cell comprising a conditional vector of claim 1.

14. The bacterial cell of claim 13, wherein the bacterial cell is selected from *C. acetobutylicum, C. difficile, C. beijerinckii, C. ljungdahlii, C. kluyveri, C. botulinum, C. autoethanogenum, C. saccharobutylicum, C. carboxidovorans, C. sporogenes, C. phytofermentans, C. ragsdalei, C.

*tyrobutyricum, C. perfringens, C. butyricum, C. cellulolyticum, C. formicaceticum, C. novyi, C. scatologenes, C. septicum, C. sordellii, C. sticklandii, C. tetani, C. thermocellum, C. thermosaccharolyticum, C. paprosolvens, C. scindens, C. pasteuranium* or *C. bifermentans*.

15. The bacterial cell of 14, wherein the bacterial cell is *C. acetobutylicum*.

* * * * *